(12) United States Patent
Muni et al.

(10) Patent No.: US 9,308,361 B2
(45) Date of Patent: Apr. 12, 2016

(54) IMPLANTABLE DEVICES AND METHODS FOR TREATING SINUSITIS AND OTHER DISORDERS

(71) Applicant: Acclarent, Inc., Menlo Park, CA (US)

(72) Inventors: Ketan P. Muni, San Jose, CA (US); Hung V. Ha, San Jose, CA (US); John H. Morriss, San Francisco, CA (US); William E. Bolger, Bethesda, MD (US); Joshua Makower, Los Altos, CA (US); John Y. Chang, Los Altos, CA (US); Randy S. Chan, San Jose, CA (US); Nga K. Van, San Jose, CA (US); Anton G. Clifford, Mountain View, CA (US); William M. Facteau, Atherton, CA (US)

(73) Assignee: Acclarent, Inc., Irvine, CA (US)

( * ) Notice: Subject to any disclaimer, the term of this patent is extended or adjusted under 35 U.S.C. 154(b) by 44 days.

(21) Appl. No.: 13/784,293

(22) Filed: Mar. 4, 2013

(65) Prior Publication Data

US 2013/0245608 A1 Sep. 19, 2013

Related U.S. Application Data

(63) Continuation of application No. 12/202,102, filed on Aug. 29, 2008, now Pat. No. 8,388,642, which is a continuation of application No. 11/544,009, filed on Oct. 4, 2006, now Pat. No. 7,419,497, which is a (Continued)

(51) Int. Cl.
*A61M 29/02* (2006.01)
*A61B 17/24* (2006.01)

(Continued)

(52) U.S. Cl.
CPC ............... *A61M 29/02* (2013.01); *A61B 17/24* (2013.01); *A61B 17/3417* (2013.01);

(Continued)

(58) Field of Classification Search
CPC ............... A61B 17/24; A61B 17/3417; A61B 17/3421; A61B 17/1204; A61B 17/12104; A61B 17/12136; A61B 17/3478; A61F 11/004; A61M 25/0075; A61M 25/0084; A61M 25/04; A61M 29/02; A61M 2025/105; A61M 2025/1052; A61M 2025/1086; A61M 2210/0618; A61M 25/10
USPC ................. 604/285, 500, 508–510, 514, 516; 606/196, 199
See application file for complete search history.

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CA | 2013323 | 9/1990 |
| CH | 668188 | 12/1988 |

(Continued)

OTHER PUBLICATIONS

Argon Medical. Maxxim Medical. Ad for Sniper EliteTM Hydrophilic Ni—Ti Alloy Guidewire (2001).

(Continued)

*Primary Examiner* — Imani Hayman
(74) *Attorney, Agent, or Firm* — Frost Brown Todd LLC

(57) ABSTRACT

A method for treating ethmoid disease in human or non-human animal subjects includes inserting a sheath containing an implantable device having an expandable member. The sheath is removed from the implantable device causing the expandable member to expand, allowing for stability of the implantable device in the subject. Stenting, spacing, draining, ventilating and/or delivering drugs and other therapeutic or diagnostic substances to desired locations within the bodies of human or non-human animal subjects may also be involved.

15 Claims, 26 Drawing Sheets

Related U.S. Application Data continuation-in-part of application No. 11/234,395, filed on Sep. 23, 2005, now Pat. No. 7,410,480, which is a continuation-in-part of application No. 11/037,548, filed on Jan. 18, 2005, now Pat. No. 7,462,175.

(51) Int. Cl.
*A61B 17/34* (2006.01)
*A61F 11/00* (2006.01)
*A61M 25/10* (2013.01)
*A61M 25/00* (2006.01)
*A61M 25/04* (2006.01)
*A61B 17/12* (2006.01)

(52) U.S. Cl.
CPC .......... *A61B 17/3421* (2013.01); *A61F 11/004* (2013.01); *A61M 25/10* (2013.01); *A61B 17/1204* (2013.01); *A61B 17/12104* (2013.01); *A61B 17/12136* (2013.01); *A61B 17/3478* (2013.01); *A61M 25/0075* (2013.01); *A61M 25/0084* (2013.01); *A61M 25/04* (2013.01); *A61M 2025/105* (2013.01); *A61M 2025/1052* (2013.01); *A61M 2025/1086* (2013.01); *A61M 2210/0618* (2013.01)

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandergrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |

(56) References Cited

U.S. PATENT DOCUMENTS

| | | |
|---|---|---|
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |

(56) References Cited

U.S. PATENT DOCUMENTS

| | | |
|---|---|---|
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |

(56) References Cited

U.S. PATENT DOCUMENTS

| | | | |
|---|---|---|---|
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim et al. |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedeelmayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |

(56) References Cited

U.S. PATENT DOCUMENTS

| | | |
|---|---|---|
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey et al. |
| 7,044,964 B2 | 5/2006 | Jang et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer et al. |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |

(56) References Cited

U.S. PATENT DOCUMENTS

| | | | |
|---|---|---|---|
| 8,142,422 B2 | 3/2012 | Makower et al. | |
| 8,146,400 B2 | 4/2012 | Goldfarb et al. | |
| 8,147,545 B2 | 4/2012 | Avior | |
| 8,167,821 B2 | 5/2012 | Sharrow | |
| 8,172,828 B2 | 5/2012 | Chang et al. | |
| 8,190,389 B2 | 5/2012 | Kim et al. | |
| 8,197,433 B2 | 6/2012 | Cohen | |
| 8,197,552 B2 | 6/2012 | Mandpe | |
| 8,249,700 B2 | 8/2012 | Clifford et al. | |
| 8,277,386 B2 | 10/2012 | Ahmed et al. | |
| 8,317,816 B2 | 11/2012 | Becker | |
| 8,337,454 B2 | 12/2012 | Eaton et al. | |
| 8,388,642 B2 | 3/2013 | Muni et al. | |
| 8,403,954 B2 | 3/2013 | Santin et al. | |
| 8,414,473 B2 | 4/2013 | Jenkins et al. | |
| 8,425,457 B2 | 4/2013 | John et al. | |
| 8,439,687 B1 | 5/2013 | Morriss et al. | |
| 8,535,707 B2 | 9/2013 | Arensdorf et al. | |
| 8,740,839 B2 * | 6/2014 | Eaton et al. | 604/94.01 |
| 8,802,131 B2 * | 8/2014 | Arensdorf et al. | 424/434 |
| 2001/0004644 A1 | 6/2001 | Levin | |
| 2001/0005785 A1 | 6/2001 | Sachse | |
| 2001/0034530 A1 | 10/2001 | Malackowski et al. | |
| 2002/0006961 A1 | 1/2002 | Katz et al. | |
| 2002/0055746 A1 | 5/2002 | Burke et al. | |
| 2002/0077593 A1 | 6/2002 | Perkins et al. | |
| 2002/0090388 A1 | 7/2002 | Humes et al. | |
| 2003/0013985 A1 | 1/2003 | Saadat | |
| 2003/0017111 A1 | 1/2003 | Rabito | |
| 2003/0018291 A1 | 1/2003 | Hill et al. | |
| 2003/0040697 A1 | 2/2003 | Pass et al. | |
| 2003/0073900 A1 | 4/2003 | Senarith et al. | |
| 2003/0083608 A1 | 5/2003 | Evans et al. | |
| 2003/0114732 A1 | 6/2003 | Webler et al. | |
| 2003/0163154 A1 | 8/2003 | Miyata et al. | |
| 2003/0220551 A1 | 11/2003 | Kimball et al. | |
| 2004/0015150 A1 | 1/2004 | Zadno-Azizi | |
| 2004/0018980 A1 | 1/2004 | Gurney et al. | |
| 2004/0020492 A1 | 2/2004 | Dubrul et al. | |
| 2004/0034311 A1 | 2/2004 | Mihakcik | |
| 2004/0043052 A1 | 3/2004 | Hunter et al. | |
| 2004/0058992 A1 | 3/2004 | Marinello et al. | |
| 2004/0064105 A1 | 4/2004 | Capes et al. | |
| 2004/0116958 A1 | 6/2004 | Gopferich et al. | |
| 2004/0127820 A1 | 7/2004 | Clayman et al. | |
| 2004/0158229 A1 | 8/2004 | Quinn | |
| 2004/0181175 A1 | 9/2004 | Clayman et al. | |
| 2004/0193073 A1 | 9/2004 | DeMello et al. | |
| 2004/0220516 A1 | 11/2004 | Solomon et al. | |
| 2004/0230156 A1 | 11/2004 | Schreck et al. | |
| 2004/0236231 A1 | 11/2004 | Knighton et al. | |
| 2004/0249243 A1 | 12/2004 | Kleiner | |
| 2004/0267347 A1 | 12/2004 | Cervantes | |
| 2005/0027249 A1 | 2/2005 | Reifart et al. | |
| 2005/0055077 A1 | 3/2005 | Marco | |
| 2005/0059930 A1 | 3/2005 | Garrison et al. | |
| 2005/0059931 A1 | 3/2005 | Garrison et al. | |
| 2005/0089670 A1 | 4/2005 | Large | |
| 2005/0107738 A1 | 5/2005 | Slater et al. | |
| 2005/0113687 A1 | 5/2005 | Herweck et al. | |
| 2005/0113850 A1 | 5/2005 | Tagge | |
| 2005/0119590 A1 | 6/2005 | Burmeister et al. | |
| 2005/0131316 A1 | 6/2005 | Flagle et al. | |
| 2005/0143687 A1 | 6/2005 | Rosenblatt et al. | |
| 2005/0182319 A1 | 8/2005 | Glossop | |
| 2005/0234507 A1 | 10/2005 | Geske et al. | |
| 2005/0244472 A1 | 11/2005 | Hughes et al. | |
| 2005/0283221 A1 | 12/2005 | Mann et al. | |
| 2006/0004323 A1 | 1/2006 | Chang et al. | |
| 2006/0047261 A1 | 3/2006 | Joshi | |
| 2006/0063973 A1 | 3/2006 | Makower et al. | |
| 2006/0095066 A1 * | 5/2006 | Chang et al. | 606/199 |
| 2006/0173382 A1 | 8/2006 | Schreiner | |
| 2006/0189844 A1 | 8/2006 | Tien | |
| 2006/0190022 A1 | 8/2006 | Beyar et al. | |
| 2006/0211752 A1 | 9/2006 | Kohn et al. | |
| 2006/0271024 A1 | 11/2006 | Gertner et al. | |
| 2006/0284428 A1 | 12/2006 | Beadle et al. | |
| 2007/0020196 A1 | 1/2007 | Pipkin et al. | |
| 2007/0112358 A1 | 5/2007 | Abbott | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0207186 A1 | 9/2007 | Scanlon et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0269385 A1 | 11/2007 | Yun et al. | |
| 2007/0282305 A1 | 12/2007 | Goldfarb et al. | |
| 2007/0293727 A1 | 12/2007 | Goldfarb et al. | |
| 2007/0293946 A1 | 12/2007 | Gonzales et al. | |
| 2008/0015544 A1 | 1/2008 | Keith et al. | |
| 2008/0033519 A1 | 2/2008 | Burwell et al. | |
| 2008/0051804 A1 | 2/2008 | Cottler et al. | |
| 2008/0097516 A1 | 4/2008 | Chang et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0132938 A1 | 6/2008 | Chang et al. | |
| 2008/0172033 A1 | 7/2008 | Keith et al. | |
| 2008/0183128 A1 | 7/2008 | Morriss et al. | |
| 2008/0188803 A1 | 8/2008 | Jang | |
| 2008/0188870 A1 | 8/2008 | Andre et al. | |
| 2008/0195041 A1 | 8/2008 | Goldfarb et al. | |
| 2008/0228085 A1 | 9/2008 | Jenkins et al. | |
| 2008/0262508 A1 | 10/2008 | Clifford et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0319424 A1 | 12/2008 | Muni et al. | |
| 2009/0030274 A1 | 1/2009 | Goldfarb et al. | |
| 2009/0088728 A1 | 4/2009 | Dollar et al. | |
| 2009/0156980 A1 | 6/2009 | Eaton et al. | |
| 2009/0163890 A1 | 6/2009 | Clifford et al. | |
| 2009/0187089 A1 | 7/2009 | Say et al. | |
| 2009/0187098 A1 | 7/2009 | Makower et al. | |
| 2009/0198216 A1 | 8/2009 | Muni et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2010/0030031 A1 | 2/2010 | Goldfarb et al. | |
| 2010/0042046 A1 | 2/2010 | Chang et al. | |
| 2010/0087811 A1 | 4/2010 | Herrin et al. | |
| 2010/0114066 A1 | 5/2010 | Makower et al. | |
| 2010/0174138 A1 | 7/2010 | Chang et al. | |
| 2010/0174308 A1 | 7/2010 | Chang et al. | |
| 2010/0198191 A1 | 8/2010 | Clifford et al. | |
| 2010/0198247 A1 | 8/2010 | Chang et al. | |
| 2010/0198302 A1 | 8/2010 | Shalev | |
| 2010/0210901 A1 | 8/2010 | Makower et al. | |
| 2010/0268245 A1 | 10/2010 | Chang et al. | |
| 2010/0274188 A1 | 10/2010 | Chang et al. | |
| 2010/0290244 A1 | 11/2010 | Nath | |
| 2010/0298862 A1 | 11/2010 | Chang et al. | |
| 2011/0004057 A1 | 1/2011 | Goldfarb et al. | |
| 2011/0015482 A1 | 1/2011 | Carrillo, Jr. | |
| 2011/0060214 A1 | 3/2011 | Makower | |
| 2011/0112512 A1 | 5/2011 | Muni et al. | |
| 2011/0166190 A1 | 7/2011 | Anderson et al. | |
| 2012/0071710 A1 | 3/2012 | Gazdzinski | |
| 2012/0071824 A1 | 3/2012 | Chang et al. | |
| 2012/0136207 A1 | 5/2012 | Goldfarb et al. | |
| 2012/0184983 A1 | 7/2012 | Chang et al. | |
| 2012/0245419 A1 | 9/2012 | Makower et al. | |
| 2012/0265094 A1 | 10/2012 | Goldfarb et al. | |
| 2013/0231529 A1 | 9/2013 | John et al. | |
| 2013/0245608 A1 | 9/2013 | Muni et al. | |
| 2013/0261388 A1 | 10/2013 | Jenkins et al. | |

FOREIGN PATENT DOCUMENTS

| | | |
|---|---|---|
| CN | 2151720 | 1/1994 |
| CN | 2352818 | 12/1999 |
| DE | 3202878 | 8/1983 |

(56) References Cited

FOREIGN PATENT DOCUMENTS

| | | |
|---|---|---|
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 4-224766 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 5-503650 | 6/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 94/21320 | 9/1994 |
| WO | WO 95/02430 | 1/1995 |
| WO | WO 96/29071 | 9/1996 |
| WO | WO 97/21461 | 6/1997 |
| WO | WO 98/55174 | 12/1998 |
| WO | WO 99/00064 | 1/1999 |
| WO | WO 99/24106 | 5/1999 |
| WO | WO 99/26692 | 6/1999 |
| WO | WO 99/30655 | 6/1999 |
| WO | WO 99/32041 | 7/1999 |
| WO | WO 99/59649 | 11/1999 |
| WO | WO 00/09190 | 2/2000 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/05462 | 1/2001 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/035204 | 3/2007 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal, N. 'An Improved stent for Use in the Surgical Management of Congenital Posterior Choanal Atresia' J. Laryngol. Otol. (1988) vol. 102 pp. 146-147.

Becker, A.E. 'Restenosis After Angioplasty' The Lancet (1988) vol. 331, No. 8584 p. 532.

Benninger et al.; Adult Chronic Rhinosinusitis: Defintions, Diagnosis, Epidemiology, and Pathophysilogy' Arch Otolaryngol Head and Neck Surg. vol. 129 (Sep. 2003) pp. A1-S32.

Bent et al. 'The Frontal Cell as a Cause of Frontal Sinus Obstruction' American Journal of Rhinology, vol. 8, No. 4 (1994) pp. 185-191.

Binner et al. 'Fibre-Optic Transillunination of the Sinuses: A Comparison of the Value of Radiography and Transillumination in Antral Disease' Clinical Otolaryngology. vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115 No. 4 pp. 293-299.

Casiano et al. 'Endoscopic Lothrop Procedure: the University of Miami Experience' American Journal of Rhinology, vol. 12, No. 5 (1998) pp. 335-339.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacetylated Enol Ethers-General Synthetic Procedure and Heterocyclic Ring Closure Reactions with Hydroxylamine' Synthesis, (Jun. 1991) pp. 483-486

(56) References Cited

OTHER PUBLICATIONS

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
Eremychev, V.A. 'Needles for Puncture and Drainage of the Maxillary Sinus' Meditsinskaya Tekhnika, No. 5 (1974) pp. 54-55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg.(1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al. 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketone—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' i CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus' OASIS—Online Abstract Submission and Invitation System, 1996-2006, Coe Truman Technologies, Inc.
Gottmann, et al. 'Successful Treatment of Recurrent Post-Operative Frontal Sinus Stenoses by Banoon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefmic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss and medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39.1 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375-378.
Ingals, E.F. 'New Operation and Instruments for Draining the Frontal Sinus' Ann. Otol. Rhino. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik and Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vase. Interv. Radiol. (1995) vol. 6, No. 5 pp. 711-713.

(56) References Cited

OTHER PUBLICATIONS

Lanza, D.C. 'Postoperative Care and Avoiding Frontal Recess Stenosis' Internatinal Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser.Www.xomcat.com/xomfrance/index.php?zone=both&cat=18&sub=58&prodline=1272.(Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron—Rich Olefins' J. Org. Chem. vol. 60, No. 11 (1995) pp. 3523-3528. American Chemical Society.
Nasal Surgery and Accessories, Jan. 25, 2007; www.technologyforlife.com.au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997). pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.

Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001). vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein. During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at.bhj.org/journal/1999_4104_oct99/sp_659.htm.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer Ltd. Ibaraki, Japan (2004) wwwl.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology.vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp, 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.

(56) References Cited

OTHER PUBLICATIONS

Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1 pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application. No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
Intenational Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application. No. PCT/US2006/029695.

(56) References Cited

OTHER PUBLICATIONS

International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Mar. 31, 2011 for Application No. PCT/US2009/069143.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.

(56) References Cited

OTHER PUBLICATIONS

USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/648,158, filed Dec. 29, 2006.
U.S. Appl. No. 11/789,705, filed Apr. 24, 2007.
U.S. Appl. No. 11/804,308, filed May 16, 2007.
U.S. Appl. No. 11/804,309, filed May 16, 2007.
U.S. Appl. No. 13/840,430, filed Mar. 15, 2013.
English Machine Translation for JP 5-503650, Jun. 17, 2013.
Japanese Office Action, Notification of Reasons for Refusal dated Sep. 18, 2013 for Application No. JP 2011-527942.

* cited by examiner

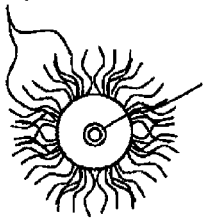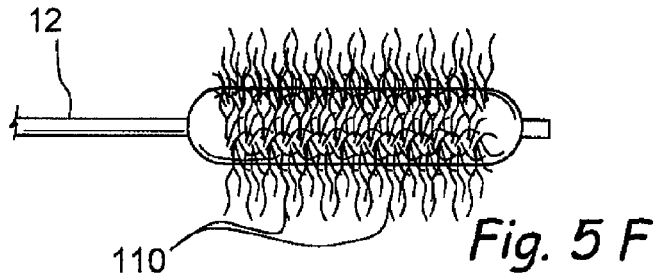
*Fig. 5 F'*     *Fig. 5 F*
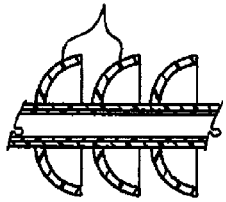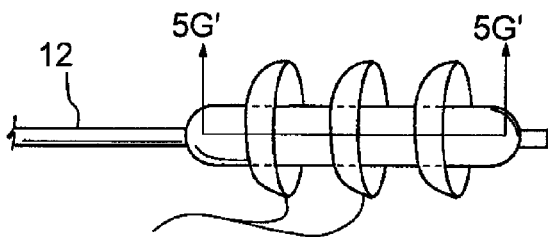
*Fig. 5 G'*     *Fig. 5 G*
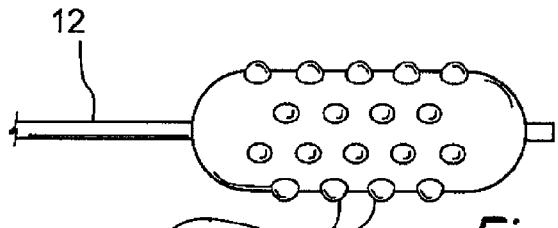
*Fig. 5 H*
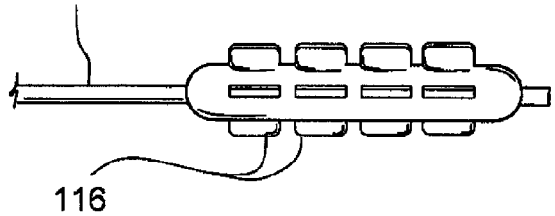
*Fig. 5 I*
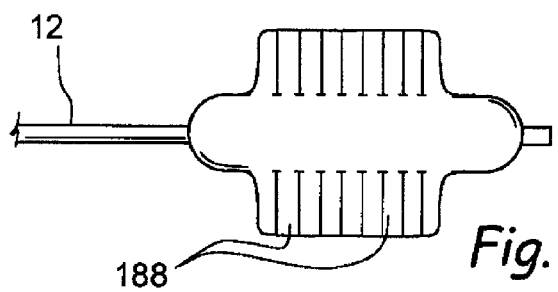
*Fig. 5 J'*     *Fig. 5 J*

IMPLANTABLE DEVICES AND METHODS FOR TREATING SINUSITIS AND OTHER DISORDERS

RELATED APPLICATIONS

This application is a continuation of U.S. patent application Ser. No. 12/202,102 filed Aug. 29, 2008, and now issued as U.S. Pat. No. 8,388,642, which is a continuation of U.S. patent application Ser. No. 11/544,009 filed Oct. 4, 2006 and now issued as U.S. Pat. No. 7,419,497, which is a continuation-in-part of U.S. patent application Ser. No. 11/234,395 filed Sep. 23, 2005 and now issued as U.S. Pat. No. 7,410,480, which is a continuation in part of Ser. No. 11/037,548 filed Jan. 17, 2005 and now issued as U.S. Pat. No. 7,462,175, the entire disclosure of each such patent and patent application being expressly incorporated herein by reference.

FIELD OF THE INVENTION

The present invention relates generally to medical devices and methods and more particularly to substance delivering implants and methods for treating a broad range of disorders including but not limited to sinusitis and other ear, nose and throat disorders.

BACKGROUND

The most common corrective surgery for chronic sinusitis is functional endoscopic sinus surgery (FESS). In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical treatment of diseases of the frontal sinuses presents unique postsurgical management issues due to the potential for formation of scar tissue, synachiae, or osteogenesis in the surgically altered frontal outflow tract. Thus, in order to maintain patency during the postsurgical period, stents are sometimes placed in the frontal outflow tract. Typically, it is intended for stents to remain in the fontal outflow tract for at least 1-8 weeks following FESS for treatment of frontal sinusitis and possibly as long as 6-12 months following surgeries for correction of frontal outflow tract stenosis.

Various types of makeshift stents have been used for this purpose, including segments of silicone drainage catheters, rolled silicone sheeting, segments of Foley catheters and Dacron materials. Also, the Freeman™ Frontal Sinus Stent is commercially available from InHealth Technologies, Inc., Carpinteria, Calif. The Freeman™ stent comprises a silicon tube that has flanges on either end to retain the stent within the frontal outflow tract for a desired period of time following surgery. In some cases, surgeons use gel like materials to form a "stent" in situ. One example of such material is the Mero-Pack™ Bioresorbable Nasal Dressing and Sinus Stent available from Medtronic ENT, Inc., Jacksonville, Fla. The Mero-Pack™ material consists of 80 percent esterified hyaluronic acid and 20 percent collagen. This material is inserted while in its dry state and, upon hydration, swells to 1.0 cm diameter in about six seconds. When in its hydrated state, this material is a biocompatible, muco-adhesive gel.

Some investigators have proposed the use of frontal sinus spacers or sheaths that elute drugs to facilitate healing in addition to performing the usual stenting function. For example, United States Patent Application Publication 2004/0116958A1 (Gopferich et al.), now U.S. Pat. No. 8,740,929, issued Jun. 3, 2014, describes a tubular sheath or "spacer" formed of biodegradable or non-biodegradable polymer that, prior to insertion in the frontal outflow tract, is loaded with a controlled amount of an active substance, such as a corticosteroid or anti-proliferative agent. After surgery to create a fenestration in a frontal sinus as been performed, the sheath (which has been preloaded with the active substance) is inserted into the surgically created fenestration where it a) deters closure of the surgically created fenestration, b) serves as a conduit to facilitate drainage from the sinus and d) delivers the active substance. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir. In some embodiments, the sheath may be anchored by causing the end of the sheath that extends into the sinus to swell or otherwise enlarge.

To date, the use of stents and spacers in relation to nose and sinus surgery has been largely limited to placement in the frontal outflow tract following frontal sinus surgery. However, as new devices and methods become available for the treatment of other types of nasal and sinus disorders, there will likely be a need for intranasal or sinus spacers and stents (with or without drug eluting capabilities) suitable for placement at various locations lot limited to the frontal outflow tract.

For example, the ethmoid air cells are anatomical cavities that do not have native ostia or openings into the nasal cavity. In the prior art, diseased ethmoid air cells have sometimes been treated by a procedure known as an ethmoidectomy wherein a man made passageway is formed between the interiors of the ethmoid air cells and the nasal cavity. Stenting and/or delivery of drugs or other therapeutic substances into these man made ethmoidectomy passageways has been, in at least some cases, been desirable. To accomplish this, strips of gauze soaked with medication may be pushed into the man made opening and later extracted. Also, in this regard, U.S. Pat. No. 6,543,452 (Lavigne) describes a nasal intubation device tha comprises a flexible tube having a flanged distal tip whereon the flanges generally from an arrow shape. The distal tip of this device is capable or penetrating through tissue (e.g., through the ethmoid bulla) to a desired position (e.g., within the ethmoid air cells). Openings are formed in a distal portion of the intubation device so that medication (e.g., a typical steroid) injected through the flexible tube will flow out of the tube into contact with the adjacent area (e.g., the diseased ethmoid air cells). In some cases, a cannula-trocar may be initially inserted and the nasal intubation device may then be advanced through that cannula-trocar. Also, European Patent Publication EP0624349 (Milewski) describes a balloon-tipped catheter having an anatomically shaped balloon which may be inserted through a surgically created opening into a body cavity (e.g., frontal sinus or ethmoid cell) and inflated to create a tamponade by being shaped to suit the anatomical shape of the cavity.

Also, in the future, placement of a drug eluting or non-drug eluting stents or spacer devices may also be desirable in the treatment of otitis media or inflammation of the middle ear. Most cases of otitis media are associated with some degree of Eustachian tube dysfunction. Because air cannot adequately pass through the Eustachian tube into the middle ear, negative pressure can be created within the middle ear. This negative pressure may essentially pull or draw fluid out of the lining of the middle ear/mastoid, thereby resulting in an accumulation of fluid in the middle ear behind the eardrum. In some cases, fluid that accumulates within the middle ear can become infected. Several types of otitis have been identified. Serous otitis typically results from a fairly sudden obstruction of the Eustachian tube and is characterized by the collection of generally thin, clear fluid in the middle ear and mastoid. If this fluid does not clear within a few weeks, it is considered chronic serous otitis. Secretory otitis typically occurs in small children and is characterized by the collection of a thick fluid in the middle ear and mastoid. This thick fluid contains muccoid material that has been secreted by the mucous glands of the middle ear and also contains enzymes that can damage the small bones and other tissues of the middle ear. If left untreated, these enzymes can erode the bones enough to cause permanent hearing loss. Acute otitis media is characterized by the accumulation of pus in the middle ear and typically occurs in patients who have active respiratory infections which result in an abrupt obstruction of the Eustachian tube at the same time as infectious bacteria are present. Without antibiotic treatment, acute otitis of bacterial origin can cause perforation of the eardrum, with drainage of pus from the ear. Although the eardrum may heal after the infection has resolved, permanent damage to the middle ear and/or the inner ear can sometimes result from infections of this severity. Chronic otitis media is typically caused by a form of chronic mastoiditis and results in a chronic infection of the middle ear and mastoid cavity. Because the mastoid bone is involved, treatment with antibiotics administered by traditional routes of administration (i.v., i.m., oral, etc.) sometimes does not remove the infection from the bone and surgical removal of the infected mastoid bone may be necessary. A common complication associated with chronic otitis and mastoiditis is cholesteatoma. A cholesteatoma is a soft tissue sac that emanates from the eardrum and grows back into the middle ear or mastoid, thereby creating a mass of progressively increasing size which can destroy or damage the bones of the middle ear, the inner ear, the facial nerve and/or portions of the brain. Thus, the various forms of otits can be very serious if left untreated. As new interventional or surgical techniques are developed for treatment of Eustachian tube dysfunction and/or otitis media, it may be desirable to place drug eluting or non-drug eluting stents within the Eustachian tube.

Apart from the drug eluting sheath described by Gopferich et al., various other types of implantable drug delivery devices have been proposed for use in the nose and/or paranasal sinuses. For example, U.S. Pat. No. 3,948,254 (Zaffaroni) describes implantable drug delivery reservoirs having microporous walls. The reservoir may be formed of a solid drug carrier that is permeable to passage of the drug and the rate of passage of the drug through the microporous wall may be slower than the rate at which the drug passes through the solid drug carrier that forms the reservoir. Zaffaroni also describes a number of applications for the implantable drug delivery devices including placement in a nasal passage. Specifically, Zaffaroni claims a nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micropores, and (d) wherein the device releases drug when in a nasal environment by passage of drug from the carrier and through the liquid to the exterior of the device to produce a useful result. The entire disclosure of U.S. Pat. No. 3,948,254 (Zaffaroni) is expressly incorporated herein by reference.

Other publications have also reported that introduction of drugs directly into the paranasal sinuses is effective in the treatment of sinusitis. See, Tarasov, D. I., et al., *Application of Drugs Based on Polymers in the Treatment of Acute and Chronic Maxillary Sinusitis*, Vestn Otorinolaringol. Vol. 6, Pages 45-7 (1978). Also, R. Deutschmann, et al., *A Contribution to the Topical Treatment of [Maxillary] Sinusitis Preliminary Communication*, Stomat. DDR 26 (1976), 585-592 describes the placement of a resorbable drug delivery depot within the maxillary sinus for the purposes of eluting drugs, specifically Chloramphenicol. In this clinical series a water soluble gelatin was used as carrier and was mixed with the drug prior to application and introduced as a mass into the sinus. Since the substance had little mechanical integrity and dissolved in a relatively short timeframe, to achieve a therapeutic effect, the author suggested that it must be instilled every 2 to 3 days. An alternative to gelatin could be a sponge loaded with the therapeutic substance as suggested in U.S. Pat. No. 6,398,758 (Jacobsen, et al.). In this patent directed at delivering a sustained release device against the wall of a blood vessel, a hollow cylindrical sponge is loaded with drug and pressed against the wall. This allows the drug to contact the wall while sustaining blood flow within the center of the lumen. Further, a skin is provided to direct the drug into the walls of the blood vessel and prevent drug from flowing into the lumen. While sponges loaded with drug at the time of their application do permit some degree of sustained release, the time required to load them also correlates closely the time over which they will elute substance. Thus, if delivery is required for a longer period of time additional mechanisms must be employed to regulate their release.

There are also several examples in the patent literature where various sustained release mechanisms have generally been proposed using systems with pre-incorporated drugs into matrices or polymers. These include U.S. Pat. No. 3,948,254 (Zafferoni), US 2003/0185872A2 (Kochinke), now U.S. Pat. No. 7,074,426, issued Jul. 11, 2006, WO 92/15286 (Shikani), and U.S. Pat. No. 5,512,055 (Domb, et al.). In general, these references discuss various materials and structures that may be used to construct sustained drug delivery vehicles and provide a good overview of the state of sustained drug delivery art. While helpful in laying out certain materials and schemes for creating sustained release systems for drugs, each of these references, however, do not describe specific methods, means or structures which would permit them to be easily adapted for intended uses that are targeted in this application.

Other examples of implantable drug delivery devices include those described in U.S. Pat. Nos. 3,993,073; 4,217,898; 5,304,123; 6,042,561; 6,183,461; 6,780,168 and 6,783,522, the entire disclosure of each such patent being expressly incorporated herein by reference.

There remains a need in the art for the development of new devices and methods for delivering drugs and other therapeutic or diagnostic substances over a sustained period of time into paranasal sinuses, Eustachian tubes, middle ear and/or other locations within the body for the treatment of sinusitis, otitis or other diseases and disorders.

SUMMARY OF THE INVENTION

Various embodiments of the present invention provide for the low profile delivery of an implantable substance delivery device and/or spacer. In one aspect of the present invention, a small diameter hole is made in a wall to a sinus cavity with a trocar-tipped needle which minimizes trauma to the tissue and underlying bone. A sheath is left in place in the hole to allow for the low profile introduction of an uninflated implantable substance delivery device and/or spacer. The uninflated implantable substance delivery device is passed through the sheath to a location within a sinus or air cell. The sheath is withdrawn and the substance delivery device and/or spacer is expanded in situ by injecting a substance through a fill tube. The substance delivery device and/or spacer is left in the sinus or air cell for sustained delivery of a desired substance.

In accordance with an embodiment of the present invention, there is provided a method for treating ethmoid disease (e.g., infection or inflammation of the ethmoid air cells) in a human or animal subject, wherein a penetrator (e.g., a straight or angled sinus needle) is advanced through the ethmoid bulla to create an opening (e.g., an ethmoidotomy) that leads into at least one ethmoid air cell. In some cases, the opening may extend through 2 or more ethmoid air cells. The penetrator has a sharp trocar tip and relatively small cross-section to minimize fracture or damage to the bulla and bones in the ethmoid air cell (s). Thereafter, an implantable device having an inflatable reservoir is advanced into or through the opening created by the penetrator and the reservoir is inflated. In some embodiments, the implantable device may function as a spacer (e.g. a stent) to maintain patency of the opening for a period of time (e.g., between 1 hour to 90 days, preferably between 7 to 29 days, most preferably about 14 days and in some cases about 7 days) after formation of the opening. Additionally or alternatively, in some embodiments the implantable device may function to deliver (e.g., elute) a diagnostic or therapeutic substance. Additionally or alternatively, in some embodiments the implantable device may function as a conduit to facilitate drainage from or ventilation of the ethmoid air cells. In embodiments were the implantable device is intended to function as a spacer (e.g., a stent), an inflation substance (e.g., saline solution) may be used to inflate the reservoir to a diameter that will provide the desired spacing. In embodiments where the implantable device is intended to deliver a diagnostic or therapeutic substance, the desired diagnostic or therapeutic substance may be introduced into or formed within the reservoir and the reservoir may be constructed such that a diagnostically or therapeutically effective amount of the substance will elute from (e.g., leak, flow or be transported out of) the reservoir while the device is implanted. In embodiments where the implantable device is intended to facilitate drainage and/or ventilation, one or more channels (e.g., lumens, surface grooves, flowpaths, etc.) may be formed on or in the device to allow for such drainage and/or ventilation. Also, in some embodiments, the implantable device may incorporate position maintaining member(s) that abut, engage or attach to an adjacent anatomical structure(s) to maintain at least part of the implantable device (e.g., the reservoir) in a desired position.

Further in accordance with an embodiment of the invention, there is provided an implantable device which may be used to deliver a diagnostic or therapeutic substance to any desired location within the body of a human or animal subject, including but not limited to locations within the nose, throat, paranasal sinus or ear. This device initially has a relatively small cross-sectional profile for delivery to the desired location by utilizing a fillable reservoir and deployable position maintaining member. This device comprises i) an elongate tubular shaft having a proximal end, a distal end and a lumen, ii) an expandable reservoir positioned on the tube at a location closer to its distal end than to its proximal end, said reservoir being in communication with the lumen such that a substance may be introduced through the lumen into the reservoir causing the reservoir to expand; at least a portion of said reservoir being substance-permeable such that the substance will elute from the reservoir in a therapeutically or diagnostically effective amount, and iii) at least one deployable position maintaining member that abuts, engages or attaches to an adjacent anatomical structure after being deployed to substantially maintain the reservoir at said location within the subject's body. In some embodiments, the position maintaining member may comprise a suture receiving member (e.g., a loop, slot, bar, etc.) useable for attaching the device to an adjacent anatomical structure by way of a suture or other connector (e.g, staple, clip, etc.) and/or one or more projections (e.g., arms) that protrude from the device such that they will abut or engage (e.g., frictionally engage or exert pressure upon) an adjacent anatomical structure thereby substantially holding the device at the desired implantation location. In some embodiments, the reservoir may comprise an expandable reservoir such as a sac or balloon. In some embodiments, a plurality of reservoirs may be present. The substance may elute from the reservoir at a discrete location or region, or it may elute from substantially the entire surface of the reservoir depending on the therapeutic or diagnostic aim of the procedure. In some embodiments small holes will be laser cut in the reservoir to allow the substance to pass out of the reservoir through such holes at a desired rate. Also, in some embodiments, the position maintaining member(s) is in a non-deployed (e.g., collapsed or stowed) position during introduction of the device into the body and may subsequently assume a deployed (e.g., extended or protruding) position to hold the device at its desired implantation location. The position maintaining member(s) in a preferred embodiment is small retention wing(s) made of nitinol wire that spring outward inside of an ethmoid air cell, but also have a relatively light spring force so that the device can be pulled through a small opening in the ethmoid bulla safely by reducing or eliminating damage to the bulla or bones of the ethmoid air cell(s). Beneficially, the device can be removed in a physician's office rather than a surgical setting.

Further in accordance with an embodiment of the present invention, there are provided methods for delivering a therapeutic or diagnostic substance to a location within the body of a human or animal subject using an implantable substance delivery device summarized in the immediately preceding paragraph. Such methods generally comprise the steps of i) introducing the implantable device into the subject's body, ii) positioning the reservoir at the desired location within the subject's body and deploying said at least one position maintaining member to abut, engage or attach to an adjacent anatomical structure in a manner that maintains the reservoir at such location, iii) providing a therapeutic or diagnostic substance and iv) introducing the substance, or a component thereof, through the lumen and into the reservoir to thereby cause the reservoir to expand and to contain a quantity of said substance such that said substance elutes from the reservoir.

Still further in accordance with the present invention, there is provided a penetrator (e.g., a sinus needle) that is useable to create an opening (e.g., an ethmoidotomy) through which the above-described substance delivery device may be introduced into a paranasal sinus or air cell (e.g., ethmoid air cell). This sinus needle may be straight or angled. In applications where the needle is to be advanced through the ethmoid bulla to create an opening into one or more ethmoid air cells (e.g., an ethmoidotomy), the needle may be angled and the angle of the needle may be oriented such that the distal tip of the needle advances on a trajectory that is parallel to or diverges away from the adjacent skull base, thereby decreasing the likelihood that the needle will inadvertently enter the cranial vault causing cerebrospinal fluid leakage and/or central nervous system complications. In some embodiments, this sinus needle may include a needle sheath that is initially placed over the needle as it is inserted into the paranasal sinus or air cell. Thereafter, the needle may be removed leaving the sheath in place and another device (e.g., an implantable substance delivery device such as that described above or other device) may then be introduced into the paranasal sinus or air cell through the sheath.

Still further in accordance with the present invention, there is provided an implantable substance delivery device that comprises i) a reservoir that contains the substance, such reservoir being at least partially flexible such that it may be compressed and permeable to allow the substance to elute therefrom, ii) a reservoir compressing member and iii) a pull member attached to the reservoir compressing member, said pull member being attached to the reservoir compressing member such that pulling the pull member will compress the reservoir. The present invention also includes methods for using such device to deliver a diagnostic or therapeutic substance. Such methods generally comprise the steps of i) implanting the device such that substance that elutes from the reservoir will enter the desired location, ii) placing a quantity of the substance in the reservoir such that the substance elutes from the reservoir and iii) pulling the pull member one or more times to compress the reservoir, thereby increasing the pressure of the substance within the reservoir. The invention also includes a method for using this device wherein the device is positioned at a desired location (e.g., within a paranasal sinus or air cell) and the pull member is periodically or continuously pulled, thereby compressing the reservoir and increasing the pressure of substance contained within the reservoir. In this manner, adequate pressure may be maintained within the reservoir to cause the substance to elute from the reservoir at a substantially constant or desired rate despite a decrease in the volume of substance contained within the reservoir.

Still further in accordance with the present invention, there is provided a filling device that may be used to fill or refill implanted substance delivery devices (including but not limited to those of the present invention) or to otherwise introduce fluid into an implanted or indwelling device (e.g., port, catheter, chamber, etc.). In general, such filling device comprises i) a syringe apparatus comprising a syringe barrel having a distal end, a nozzle on the distal end of the syringe barrel and a reservoir compressing member that may be advanced within the barrel to expel fluid from the barrel out of the nozzle, ii) a rod member extending distally from the barrel, iii) a grasper on the rod member useable to grasp the implantable device and iv) a trigger that is useable to cause the rod member to retract toward the nozzle so as to bring the implanted device into fluid connection with the nozzle such that fluid expelled from the nozzle will enter the implantable device. In some embodiments, the filling device may be operable using a single hand, thereby allowing the operator to perform other tasks with the other hand. The present invention includes methods for using such filling device to introduce fluids or substances into implanted devices, such as the implantable substance delivery devices of this invention.

Further still in accordance with the present invention, there is provided another implantable substance delivery device which comprises i) a delivery reservoir that contains the substance and which is permeable to allow the substance to elute therefrom, ii) a driving reservoir that contains an additional amount of the substance, iii) a lumen connecting the delivery reservoir to the driving reservoir and iv) a valve which allows the substance to flow from the driving reservoir, through said lumen and into the delivery reservoir when the pressure within the driving reservoir exceeds the pressure within the delivery reservoir by a predetermined amount. In some embodiments, a fill tube may extend from the driving reservoir and a one way valve may be provided to allow fluid to be infused through the fill tube into the driving reservoir but not allowing substantial leakage of fluid from the driving reservoir back out of the fill tube. The invention also includes methods for using such device by i) implanting the device at a desire location (e.g., such that drug eluting from the delivery reservoir will reach the intended therapeutic or diagnostic location) and ii) placing a quantity of substance in at least the driving reservoir. In some applications, the amount of substance in the driving reservoir may be replenished one or more times while the device remains implanted within the body.

Still further in accordance with the present invention, there is provided a sinus irrigating catheter device comprising i) an elongate tubular shaft having a lumen and a distal end and ii) a penetrating tip on the distal end of the elongate shaft, said penetrating tip being useable to penetrate through mucous membrane and bone into the paranasal sinus or air cell, such penetrating tip having a distal end opening and a plurality of side openings. In some embodiments, the irrigating catheter can be in combination with an introduction device. Such introduction device generally comprises comprising i) a substantially rigid, elongate probe having a distal end and a lumen within which the irrigation catheter is positioned and ii) handpiece graspable by the human hand, said handpiece including a trigger that is useable to advance the irrigation catheter out of the distal end of the elongate probe. The present invention also includes methods for using these devices to irrigate paranasal sinuses or air cells. In some applications, after the irrigation catheter have been used to irrigate a paranasal sinus or air cell, a guidewire may be passed through the irrigation catheter and into the sinus or air cell. Thereafter, the irrigation catheter may be removed leaving the guide wire in place and one or more other device(s) may be advanced over the guidewire.

Still further aspects and details of the present invention will be understood upon reading of the detailed description and examples set forth herebelow.

BRIEF DESCRIPTION OF THE DRAWINGS

FIG. 2C' is an end view of the distal tip of the sinus needle device of FIG. 2B.

FIG. 5A' is a distal end view of the device of FIG. 5A.

FIG. 5B' is a distal end view of the device of FIG. 5B.

FIG. 5F' is a distal end view of the device of FIG. 5F.

FIG. 5G' is a cross-sectional view through line 5G'-5G' of FIG. 5G.

FIG. 5J' is a distal end view of the device of FIG. 5J.

FIG. 5K' is a distal end view of the device of FIG. 5K.

FIG. 5L' is a distal end view of the device of FIG. 5L.

FIG. 5N' is a distal end view of the device of FIG. 5N.

DETAILED DESCRIPTION

Figure 1A:
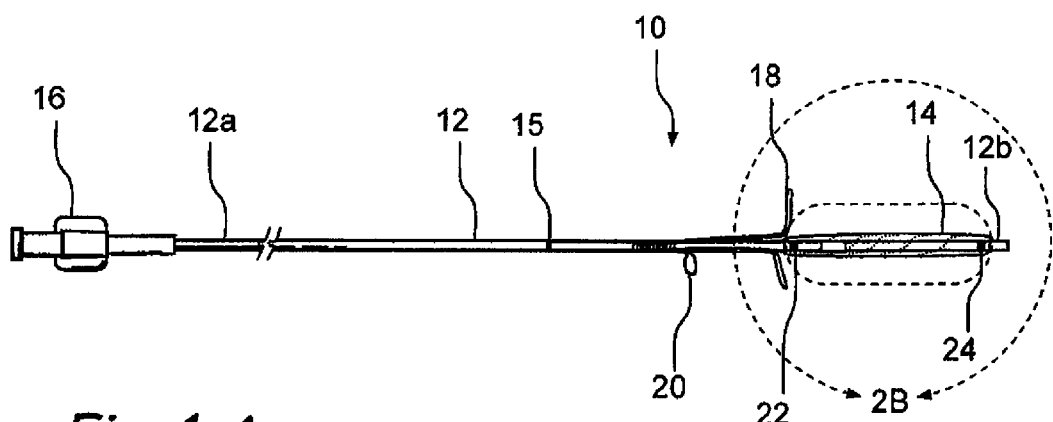
FIG. 1A is a side view of one embodiment of substance delivery device of the present invention.

The following detailed description, the accompanying drawings are intended to describe some, but not necessarily all, examples or embodiments of the invention. The contents of this detailed description do not limit the scope of the invention in any way.

FIGS. 1A-1E show one embodiment of an implantable substance delivery device and/or spacer 10 of the present invention. This device 10 comprises an elongate flexible catheter shaft 12 having a proximal portion 12a and a distal portion 12b which may be severed from one another at separation marker 15. The proximal shaft portion 12a and distal shaft portion 12b may be formed of the same or different materials and may have the same or different dimensions (e.g., diameter, wall thickness, etc.). For example, in some embodiments intended for implantation in paranasal sinuses or other ear, nose or throat locations, the proximal shaft portion 12a may be made of a suitable biocompatible material of sufficient column strength (e.g., pushability) to enable a user to push the substance delivery device 10 into the paranasal anatomy. One such material is polyamide. In some embodiments, the distal shaft portion 12b may be made of a more flexible biocompatible material such as nylon. A lumen 13 extends continuously through the shaft 12 and a plug 23 is mounted in its distal end. The plug may comprise any suitable closure member such as a wall of closed end on the tube, an end cap, a mass within the end of the lumen 13 or any other suitable flow blocking member. In the particular example shown in the drawings, the plug 23 comprises a biocompatible polymeric adhesive disposed within the distal end of lumen 13.

An expandable reservoir 14 is mounted in a collapsed configuration on the distal shaft portion 12b near its distal end. Details of the reservoir 14 are seen in FIGS. 1B and 1C. As shown, in this embodiment, the reservoir 14 comprises a balloon that has a cylindrical side wall wherein openings 31 are formed. The reservoir 14 may also be formed of any suitable biocompatible material and, in some embodiments, may comprise a balloon formed of non-compliant or semi-compliant material such as Nylon 12. The size of the reservoir 14, the number of reservoirs (such as two or more), and the number and size of the openings 31 may vary on the basis of the intended implantation location and/or the potency, viscosity (or particle size) and/or other properties of the substance being delivered. For example, in an embodiment of the device 10 intended to be passed through an ethmoidotomy channel and positioned within an ethmoid air cell to treat ethmoid sinusitis, the reservoir 14 may have a length of from about 0.5 cm to about 3.5 cm and typically approximately 2 cm, a diameter when fully expanded of about 0.1 cm to about 0.5 cm and typically approximately 0.3 cm. Also in such embodiment of the device 10, the openings 31 may comprise between about 50 openings 31 approximately 5 microns in diameter to about 5000 openings 31 approximately 80 microns in diameter, more preferably approximately 2200 laser cut openings 31 approximately 20 microns in diameter formed in the sidewall of the reservoir 14. The openings 31 can be staggered one row to the next along the device 10 and there also can be openings in the angled or tapered portions of the device 10. As seen in FIGS. 3A-3H and described in detail herebelow, this embodiment of the reservoir 14 may be inserted through a typical ethmoidotomy opening, positioned within an ethmoid air cell and filled with approximately 0.10 ml of a suspension containing 40 mg/ml of Triamcinolone Acetonide Injectable Suspension, USP (Kenalog®-40, Bristol-Myers Squibb, Somerville, N.J.). Approximately 100 μg of Triamcinolone will elute from the reservoir per day over a period of 14 days. When used for the treatment of fungal sinusitis or other fungal infections, this reservoir 14 may also be used to deliver an antifungal agent such as liposomal or non-liposomal Amphotericin B of 0.3 to 1.5 mg/kg available from Pfizer as Amphocin® anti-fungal. Systemically administered Amphotericin typically has limited distribution from the bloodstream across the mucus membranes and vice versa. With this substance delivery device 10, Amphotericin may be released locally into the mucus membrane where the offending fungal organisms are present and therapeutic concentrations of the drug may remain in the mucus as it is distributed through the sinuses by ciliary action. However, substantial amounts of the Amphotericin will not be substantially absorbed through the sinus mucosa, thereby avoiding the potential for untoward systemic effects of the Amphotericin such as renal toxicity. Also, this reservoir 14 may be capable of delivering solutions as well as suspensions to the surrounding anatomy. This is especially useful for delivery of steroids since most steroids are available as suspensions.

Also, the reservoir 14 may act as a space occupying device (e.g., a stent) after expansion and may, itself, frictionally engage or contact adjacent anatomical structure(s) to provide a degree of retention at the desired implantation location. This aspect of the reservoir 14 may be further facilitated by the provision of surface projections on the reservoir.

This type of reservoir 14 also has the advantage of being relatively small in diameter when empty or deflated and thus can be introduced or removed easily. In embodiments were this type of reservoir 14 is formed of non-compliant or semi-compliant material, the reservoir 14 will not undergo substantial elastic deformation in the filling process and thus will not exert pressure on its contents in order to expel the desired substance through openings 31. Rather, the substance in the reservoir 14 will be carried out through the openings 31 by gravity or by being in contact with the mucous that is continually moved along by the ciliary action in the sinuses. This non-pressurized delivery allows for the slow release of the desired substance over several days. In some other embodiments, the reservoir 14 may be formed of compliant or elastic material with small openings 31 such that the material of which the balloon 14 is formed will contract as substance passes out of the openings 31, thereby maintaining pressure within the balloon. This reservoir 14 may be 3.0 to 3.5 mm in diameter by 13 mm in length. The reservoir 14 may be made of Nylon 12. In this preferred embodiment as shown in FIGS. 1B and 1C, approximately 768 laser cut openings 31 are formed in the side wall of the reservoir 14. The diameter of each laser cut opening 31 is 30 microns. The distal end of shaft 12 is plugged as shown using Dymax 204CTH adhesive. The distal portion of the shaft 12 is made of Nylon 12 of an outer diameter of 0.028 inches and inner diameter of 0.020 inches and length of 17 mm. Elastomeric sleeve valve 26 is made of a 3 mm long C-flex medical grade TPE tubing. The tubing of inner diameter of 0.022 inches and wall thickness of 0.005 inches. Distal radiopaque marker 24 and proximal radiopaque marker 22 are made of a ring of Pt—Ir alloy of outer diameter 0.034 inches and inner diameter 0.030 inches. The proximal portion of the shaft 12 may be made of polyimide tubing of outer diameter 0.0618 inches and inner diameter 0.052 inches and length 20 cm. Hub 54 is a female Luer hub made of clear polycarbonate made by Qosina (Edgewood, N.Y.) part number 41519. In a preferred embodiment, each retention wing 18 is made of a bent loop of Nitinol wire of diameter 0.0086 inches The retention wings are oriented at 80° to 90° from the longitudinal axis of the device. A heat treatment of 520° C. for 20 minutes of the nitinol wire loop produces an $A_f$ of 20° c. Such a design of substance delivery device delivers 100 μg per day of Kenalog®-40 over a period of 14 days. The constraining sheath 30 is made of a length of 10 cm tubing of an outer diameter of 0.084 inches and an inner diameter of 0.075 inches.

In one embodiment, the exterior of reservoir 14 may be coated with a fracturable coating containing one or more therapeutic substances in a biodegradable matrix. When the reservoir 14 is filled, it expands. This expansion will fracture the fracturable coating such that pieces of the coating will enter the surrounding anatomy and will thereafter release the therapeutic substance(s) into the anatomy. The fracturable coating can be made from gelatin, sodium carboxymethyl cellulose or high molecular weight polyethylene glycol (PEG). The fracturable coating dissolves in the aqueous environment.

An aperture 28 as seen in FIGS. 1B-1C is formed in the catheter shaft 12 to facilitate filling of the reservoir 14. A valve 26 allows the substance (or component(s) of the substance) to flow from the lumen 13 of the catheter shaft 12 into the reservoir 14 (see FIG. 1C) but does not allow substantial backflow from the reservoir 14 into the lumen 13 (see FIG. 1B). The valve 26 may comprise any suitable type of one way valve. In the particular embodiment shown, the valve 28 comprises an elastomeric sleeve valve made of C-flex® thermoplastic elastomer (Manufacturered by Consolidated Polymer Technologies, Inc., Clearwater, Fla.).

Radiopaque markers 22 and 24 are mounted on the distal catheter shaft portion 12b to mark the proximal and distal ends of the reservoir 14. These radiopaque markers are preferably formed of material that is clearly more radiopaque than the adjacent materials and tissues. In this particular non-limiting example these markers 22, 24 are formed of Platinum-Iridium alloy.

Figure 1B:
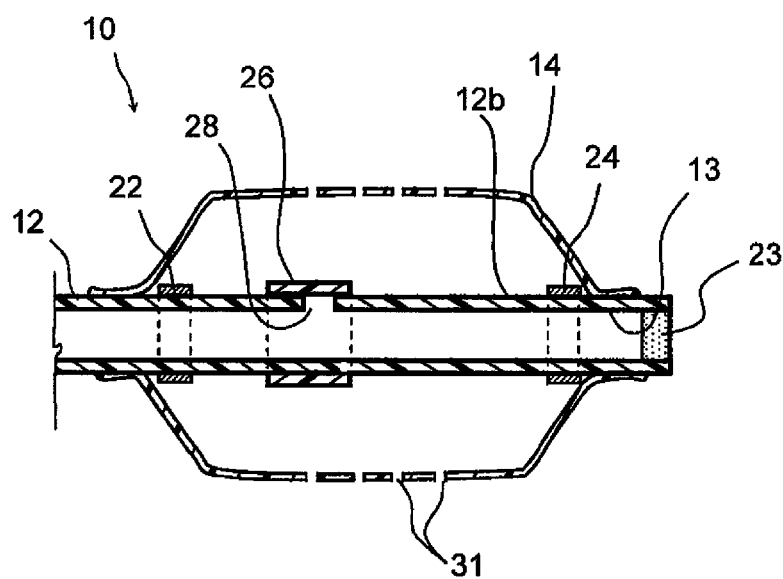
FIG. 1B is a sectional view of the distal end of the device of FIG. 1A during infusion of a substance into the expandable reservoir of the device.
Figure 1C:
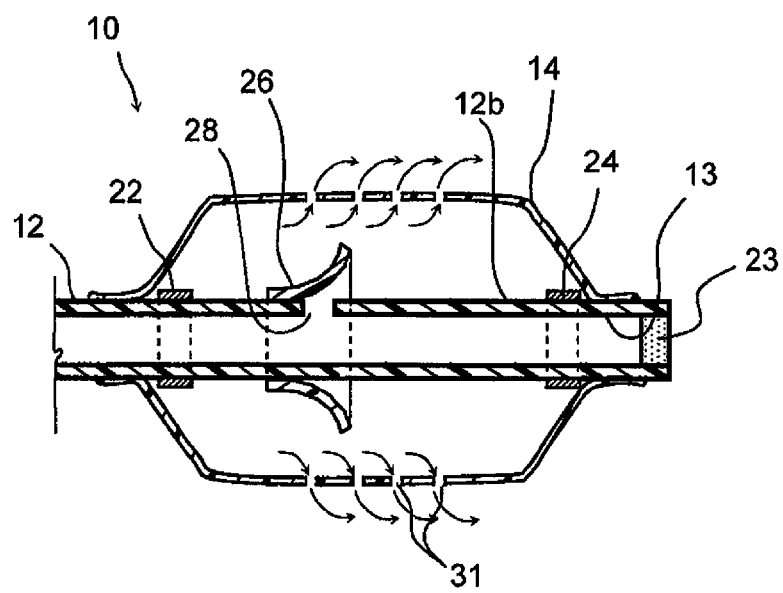
FIG. 1C is a sectional view of the distal end of the device of FIG. 1A after the expandable reservoir of the device has been filled with a substance.

This embodiment of the device 10 shown in FIGS. 1A-1E also incorporates two types of position maintaining members for holding the device at a desired location within a subject's body. In the example shown, these position maintaining members include a suture loop 20 (e.g., an eyelet) and a plurality of projections 18 (e.g., retention wings). The suture loop 20 and projections 18 may be formed of supple, flexible, resilient, elastic or superelastic material such as nickel-titanium alloy (Nitinol) to be able to be collapsed in order to fit inside a constraining sheath. At least the projections 18 may be biased to a deployed (e.g., outwardly protruding) position as seen in FIG. 1A but may sometimes be compressed or bent to a non-deployed (e.g., collapsed) configuration wherein they are substantially parallel and adjacent to the outer surface of the catheter shaft 12. In this manner, as described more fully herebelow, these projections 18 may be constrained in their non-deployed position during insertion and positioning of the device 10 and thereafter the constraint may be removed allowing these projections 18 to spring to or otherwise assume their deployed positions where they will abut or engage (e.g., frictionally engage) adjacent anatomical structure(s). In the particular example shown, the projections 18 are located proximal to reservoir 14 and are in the form of two (2) loops of wire (e.g., nickel-titanium wire) of 0.0086 inch diameter bent to form diametrically opposed retention wings. Projections 18 can also be located distal to the reservoir or both proximal and distal. When the projections 18 are nitinol, cold or warm fluid can be used to transition them to a "softer" state. The length of each projections 18 is determined based on the intended implantation site. For example, in embodiments intended to be implanted in an ethmoid sinus as described herein, each projection 18 may have a length of approximately 5 mm. The length and shape of the projections 18 may also be designed to cause minimal trauma to the anatomy while ensuring the maximum retention of the device 10 at its intended implantation location. In the example shown, the wire loops that form the projections 18 and suture loop 20 may be affixed to the outer surface of shaft 12 by winding the wire around the shaft and securing the wire to the shaft using a suitable adhesive such as cyanoacrylate, epoxy or UV curable adhesive and/or by mounting a polymeric sleeve or heat shrinkable member about the portions of wire that are wound around the shaft 12.

Figure 1D:
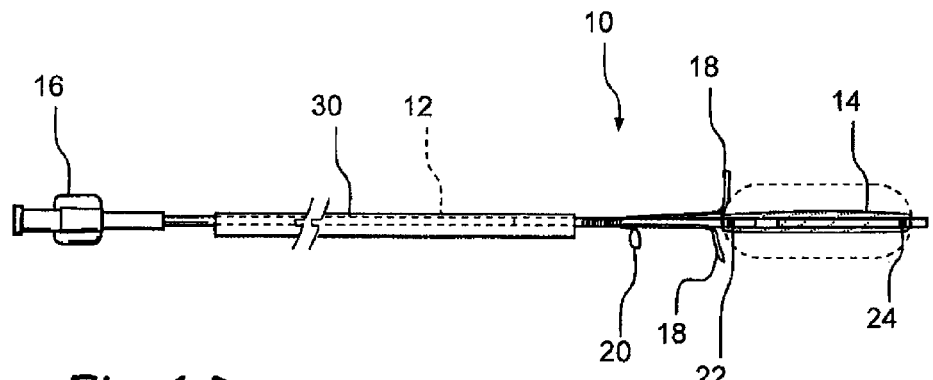
FIG. 1D is a side view of the substance delivery device of FIG. 1A with an optional moveable sheath in its retracted position.
Figure 1E:
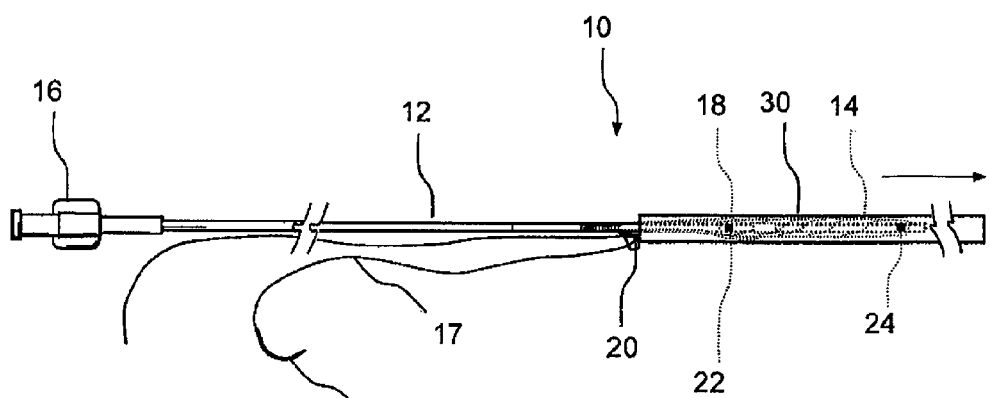
FIG. 1E is a side view of the substance delivery device of FIG. 1A with an optional moveable sheath in its extended position with a suture pre-loaded through an optional suture loop.

As shown in FIGS. 1D and 1E, the device 10 may optionally include a moveable member such as a moveable constraining sheath 30 that is moveable between a first position (FIG. 1E) where it holds the projections 18 in their non-deployed (e.g., collapsed) positions and a second position (FIG. 1D) were it releases the projections 18 allowing them to assume their deployed (e.g., outwardly extended) positions. This moveable constraining sheath 30 may also cover or surround the reservoir 14 when in its first position, thereby holding the reservoir in a compressed or collapsed state, and may leave the reservoir unconstrained when in its second position, thereby allowing the reservoir 14 to be filled with the desired substance.

FIGS. 2A-2D show a sinus needle system comprising a sinus needle 49 and a needle sheath 40. This sinus needle system may be used alone or in combination with the above-described substance delivery device 10.

Figure 2:
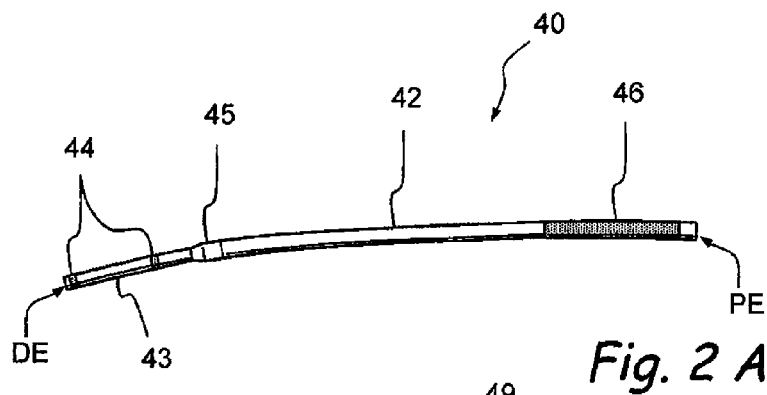
FIG. 2A is a side view of a sinus needle sheath of the present invention.
FIG. 2B is a side view of a sinus needle device of the present invention.
FIG. 2C is an enlarged side view of the distal end of the sinus needle device of FIG. 2B.
FIG. 2D is a side view of a sinus needle/sheath system comprising the needle sheath of FIG. 2A in combination with the sinus needle device of FIG. 2B.
FIG. 2E is a side view of the system of FIG. 2D mounted on an image guidance adapter device.
Figure 2:
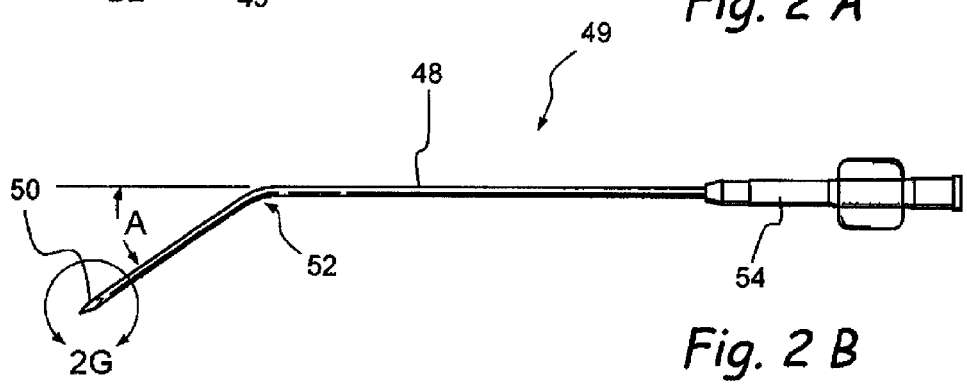
Figure 2:
Figure 2:
Figure 2:
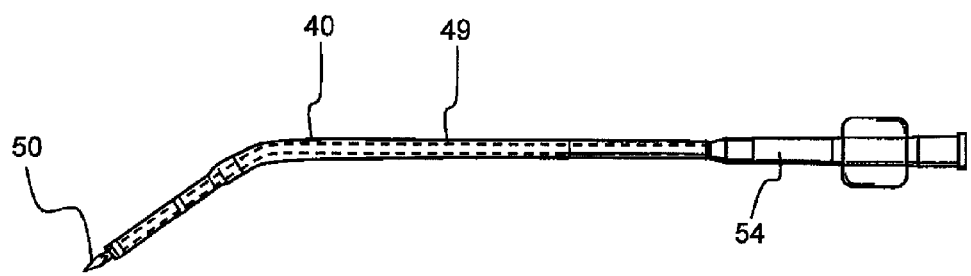
Figure 2:
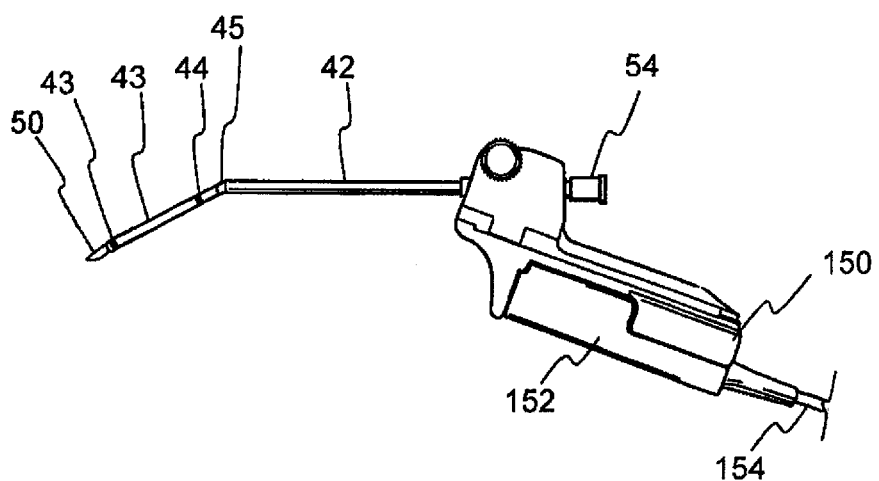

As seen in FIG. 2A, the needle sheath 40 may be formed of a biocompatible polymer such as PEBAX and comprises a proximal sheath body 42 of a first diameter, a distal sheath body 43 of a second diameter (smaller than the first diameter) and a tapered step-down segment 45 or other abutment surface therebetween. A visible marker band 46 is optionally provided on the proximal sheath body 42, near its proximal end PE. Additionally, the tapered step down segment 45 may be colored for easy visualization. Also optionally, radiopaque markers 44 may be provided at spaced apart locations within the distal sheath body 43, near the distal end DE. The use of these optional markers 44 is described herebelow in relation to the procedure shown in FIGS. 3A-3H. The needle sheath can be used to deliver therapeutic or diagnostic substances.

As shown in FIGS. 2B and 2C, the sinus needle 49 comprises an elongate needle body 48 having a beveled distal tip 50 and a female Luer hub 54 on its proximal end. In the embodiment shown in the drawings, the needle body 48 is formed of solid stainless steel wire having an outer diameter of approximately 0.07 inches. It is to be appreciated, however, that in some embodiments, other solid or tubular materials may be used, such as hypotube. Optionally, a curve 52 may be formed in the needle body. Such curve 52 may form an angle A of from about 0 degrees to about 70 degrees. For example, the embodiment shown in the drawings is intended for use in performing a needle ethmoidotomy as described herebelow and has a curve 52 which forms an angle A of about 33 degrees located about 35 mm from the distal tip 50 of the needle. As described more fully herebelow, such curve 52 allows the sinus needle 49 to be used to perform a needle ethmoidotomy with decreased potential for inadvertent penetration of the adjacent skull base and resultant breaching of the cranial vault. Also, as indicated in the enlarged view of FIG. 2C, the distal tip of this embodiment of the needle 49 may comprise a trocar tip having three beveled edges arranged symmetrically around the central axis of needle shaft with each beveled edge being disposed at an angle B of about 20 degrees relative to the longitudinal axis of the needle body 48. This design enables sinus needle 49 to cut soft tissue such as mucosa as well as thin bone such as the ethmoid bulla.

FIG. 2D shows the needle sheath 40 positioned on the needle 49. As shown, the length of the needle sheath 40 is such that when the sheath 40 is fully advanced onto the needle body 48, the proximal end PE of the sheath 49 will abut against the hub 54 of the needle 49 and the distal tip 50 of the needle 49 will protrude out of and beyond the distal end DE of the sheath 40. Needle sheath 40 is flexible enough to allow the curved region of sinus needle 49 to advance through the needle sheath 49.

U.S. Pat. Nos. 5,314,417 entitled "Safety Trocar" and 5,267,965 entitled "Safety Trocar", the entire disclosures of which are incorporated herein by reference, disclose safety mechanisms that may optionally be used in the combination with the sinus needle 49 and needle sheath 40. In another embodiment, sinus needle hub 54 may be configured to register with or nest within the proximal end PE of the needle sheath 40 to limit the advancement of the needle 49 through the sheath 40 such that just the distal tip 50 of the needle 49 can protrude out of the distal end DE of the sheath 40 and thus preventing the distal portion of the sinus needle 49 from being advanced too far out from the distal end DE of the needle sheath 40.

Optionally, for some applications, the sinus needle 49 and needle sheath 40 may be connected to optical or electrical image guidance component(s) (e.g., sensors, reflectors, light sources, etc.) so that an optical or electromagnetic image guidance system may be used, in accordance with techniques well known in the art of ear, nose and throat surgery, to determine and/or guide the positioning of the needle tip 50 within the body of human or animal subject. In some instances, the desired image guidance components may be connected to the sinus needle 49/sheath 40 assembly by way of a image guidance adapter 150 which in turn is connected to the image guidance component, such as an electromagnetic receiver 152 (e.g., GE InstaTrak®3500 Plus, General Electric Company, Fairfield, Conn.) as shown in FIG. 2E. Examples of image guidance adapters 150 that may be useable for this purpose include but are not limited to those described in U.S. patent application Ser. Nos. 11/436,892 (Makower et al.) entitled "Systems and Methods for Performing Image Guided Procedures Within the Ear, Nose, Throat and Paranasal Sinuses," now U.S. Pat. Pub. No. 2007/0208252, published Sep. 6, 2007 and 11/436,897 (Kim et al.) entitled "Adapter for Attaching Electromagnetic Image Guidance Components to a Medical Device," now U.S. Pat. No. 8,190,389, issued May 29, 2012, the entire disclosures of such patent applications being expressly incorporated herein by reference. Image guidance adapter 150 is adapted to grip the hub 54 of needle 49. In a preferred embodiment, electromagnetic receiver 152 is a part of an electromagnetic surgical navigation system such as the GE InstaTrak® system and is connected to such navigation system by an electrical connection 154. In typical usage, the needle 49 having the needle sheath 40 thereon (as seen in FIG. 2D) is rigidly attached to image guidance adapter 150. Thereafter, the location and/or the trajectory of the distal tip 50 of the needle 49 may be monitored as it is advanced within the subject's body using the surgical navigation system. In an alternate technique, the sheath 40 may be provided with a hub on its proximal end PE or otherwise constructed so that it is suitable for connection to the image guidance adapter 150. The sheath 40 alone may then be connected to the image guidance adapter 150 and the distal end DE of the needle sheath 40 may be calibrated to the location and/or the trajectory of image guidance adapter 150. Thereafter, the surgical navigation system is used to navigate needle sheath 40 through the anatomy to a desired location, such as where the distal end DE of the sheath 40 is touching or close to the face of the ethmoid bulla. The sinus needle 49 is then introduced through needle sheath 40 and an access path is created by puncturing one or more anatomical regions such as the face of the ethmoid bulla with the needle tip 130. In another method embodiment, sinus needle 49 is introduced through needle sheath 40 connected to an image guidance adapter 150 which in turn is connected to a component of an optical image guidance system such as a STARLINK™—Universal Instrument Adapter manufactured by BrainLAB.

FIGS. 3A-3K show one example of a method by which a system of devices including the above-described sinus needle 49, needle sheath 40 and substance delivery device 10 may be used to perform a needle ethmoidotomy and to provide for postoperative patency of the ethmoidotomy channel and for sustained delivery of a therapeutic substance to the ethmoid mucosa for a period of time postoperatively.

Figure 3:
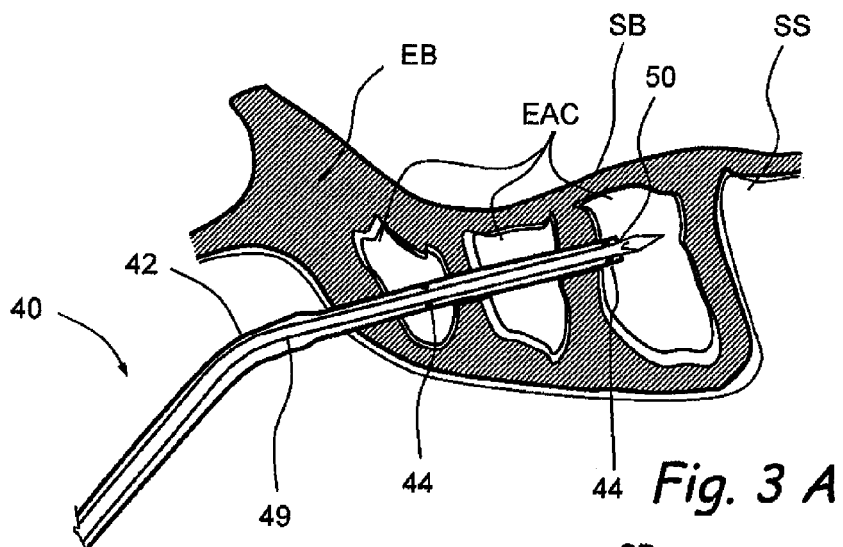
FIGS. 3A-3H and 3J-3L show steps in a method for performing an ethmoidotomy procedure with implantation of the substance delivery device of the present invention.
Figure 3:
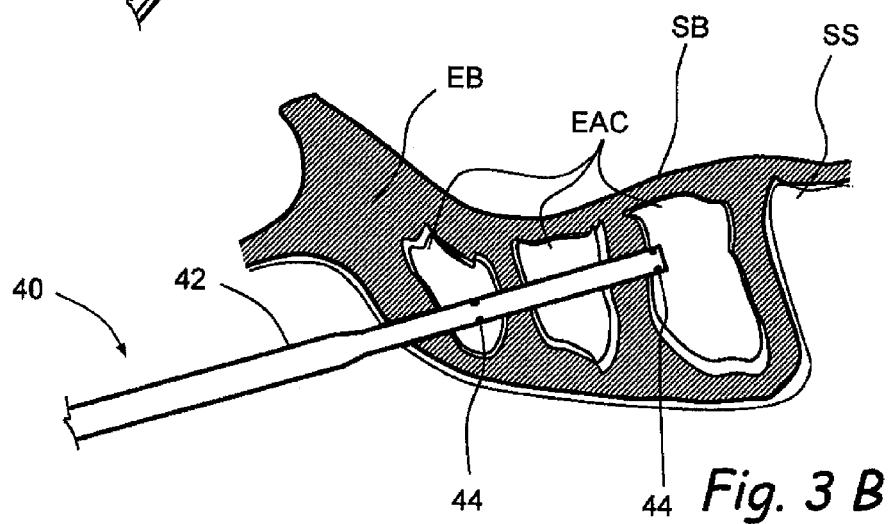
Figure 3:
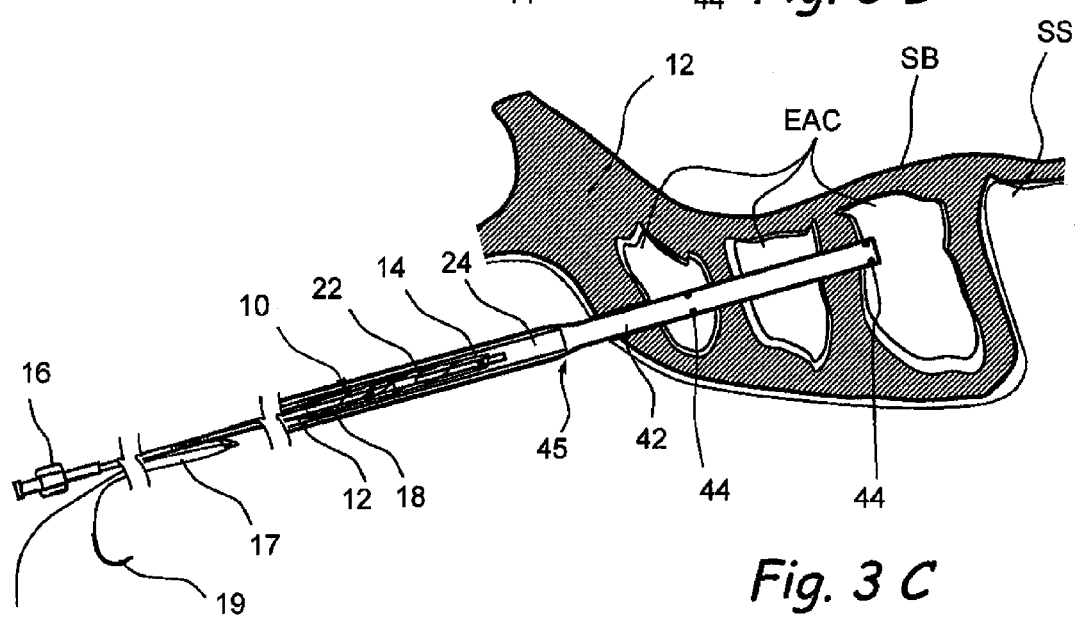
Figure 3:
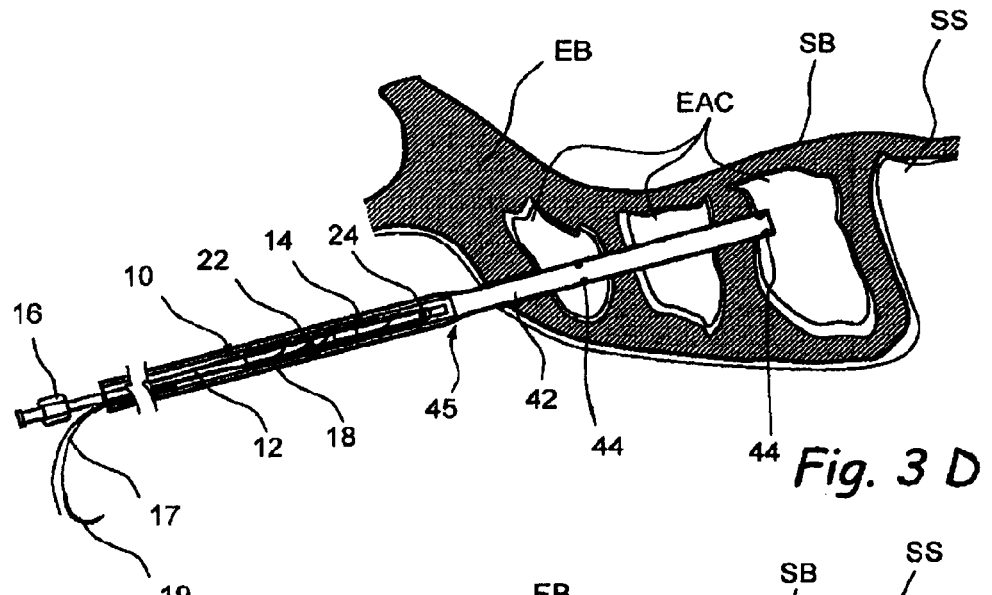
Figure 3:
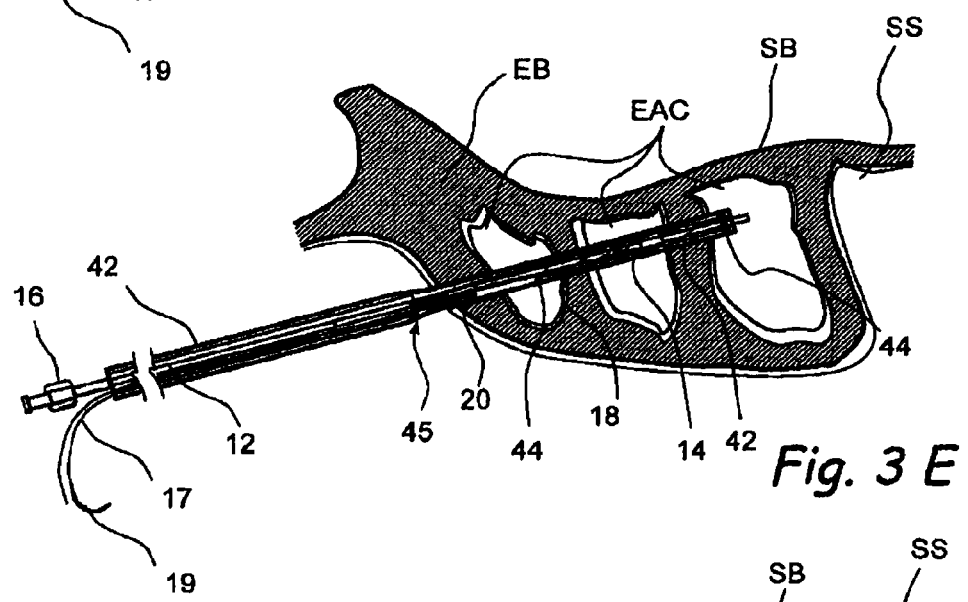
Figure 3:
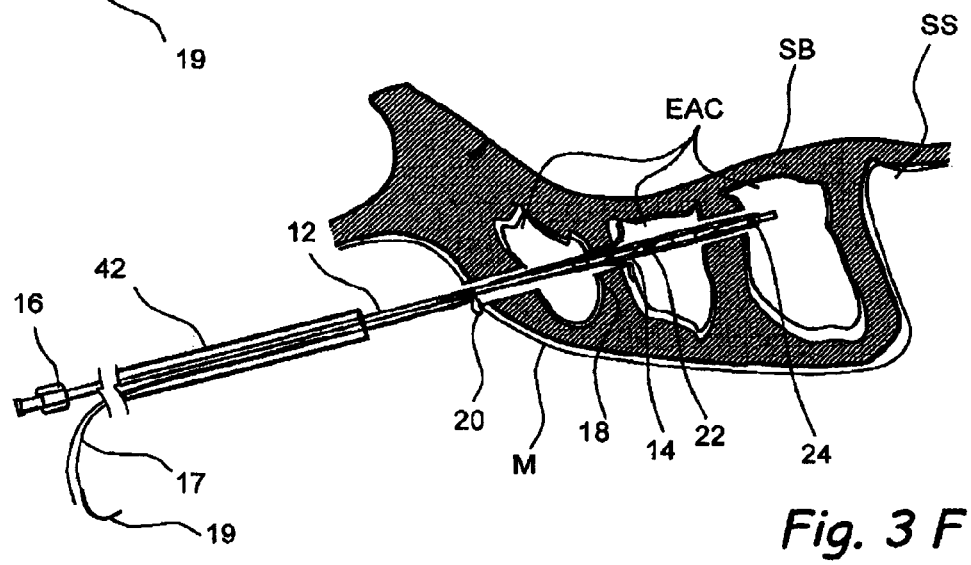
Figure 3:
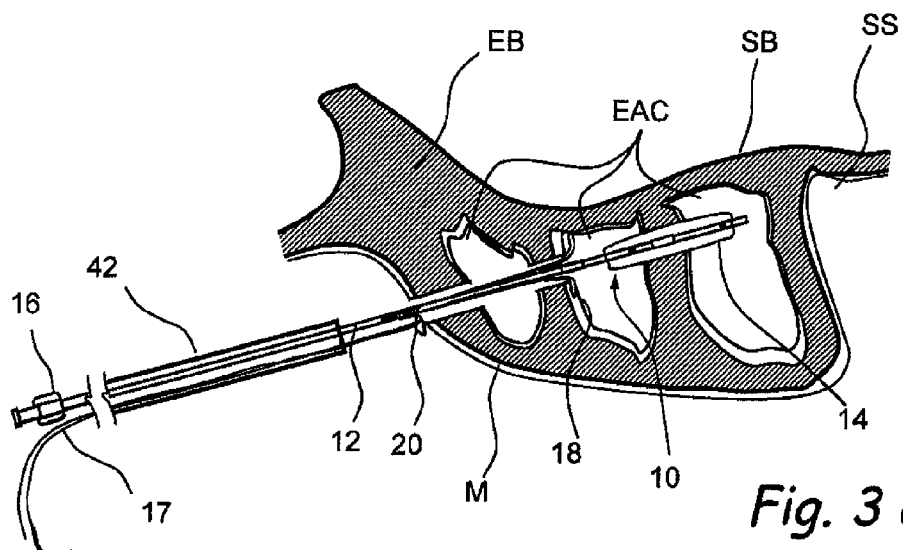
Figure 3:
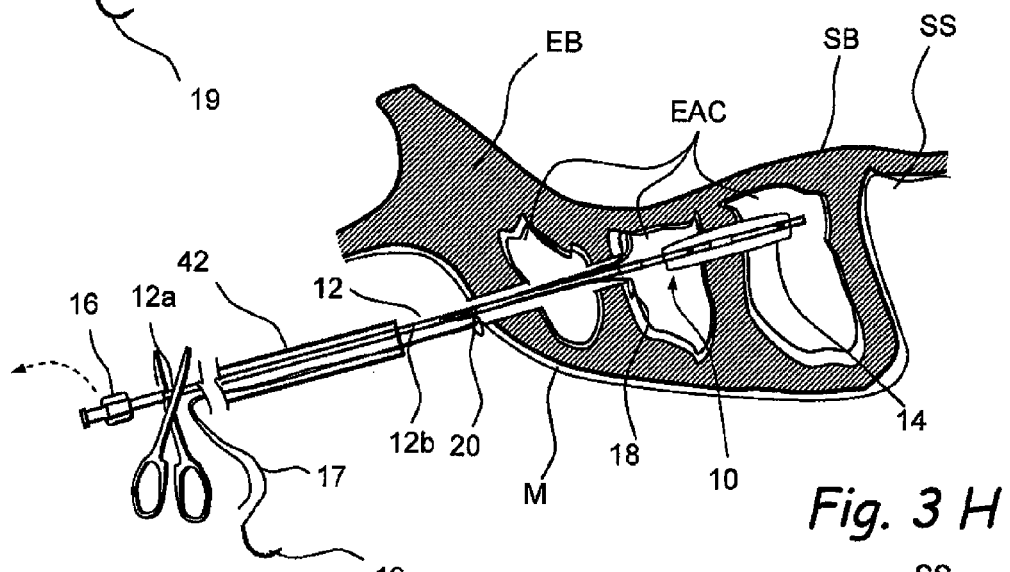
Figure 3:
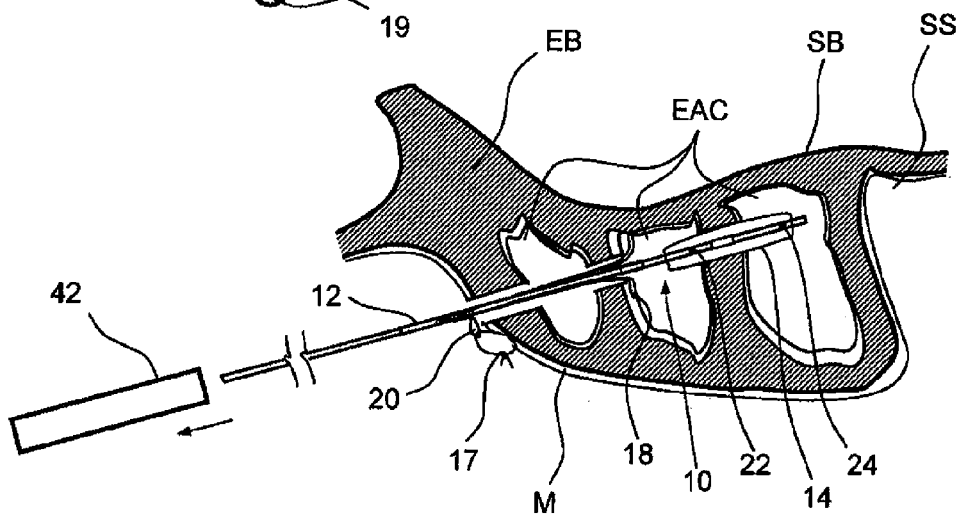
Figure 3:
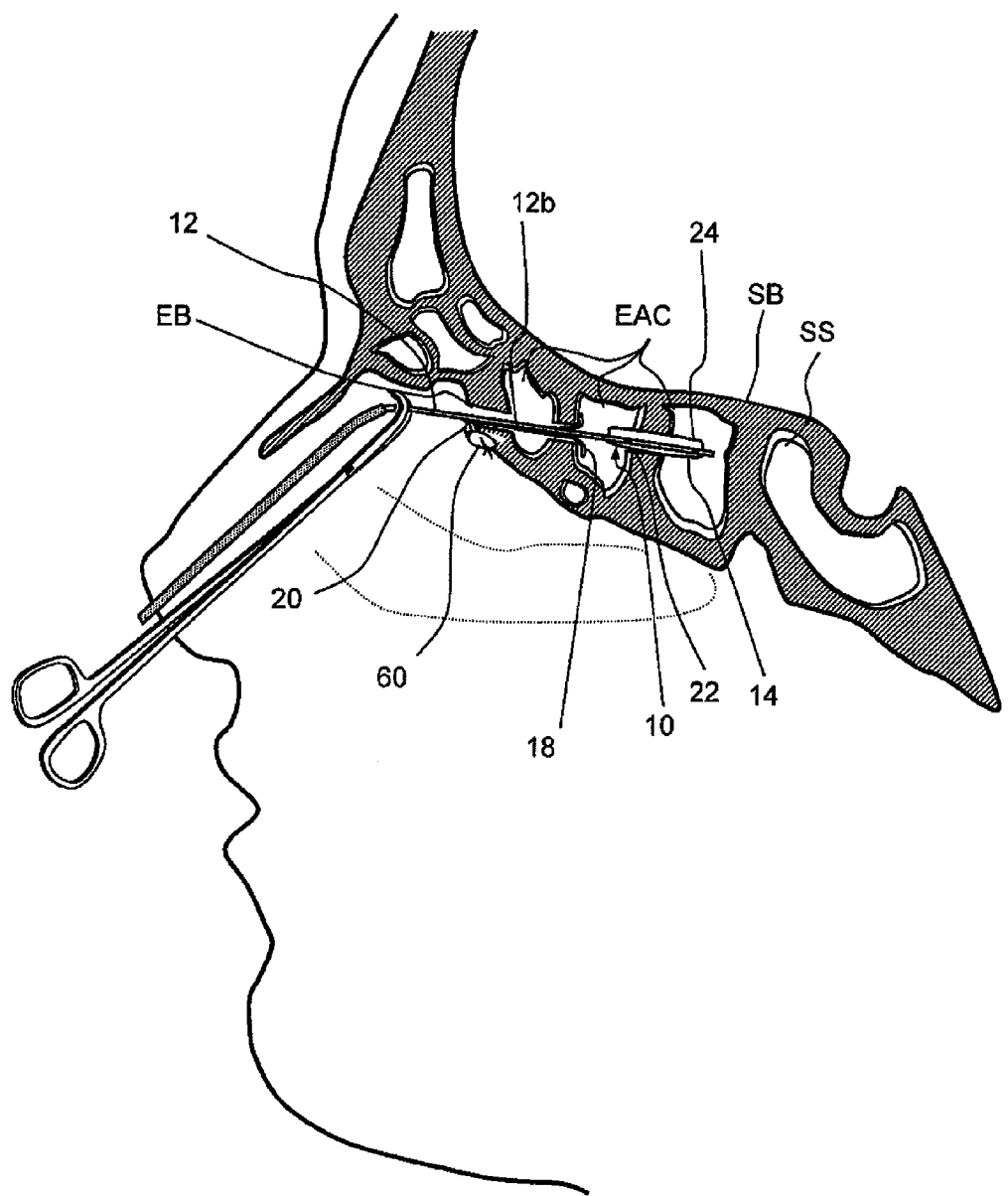
Figure 3:
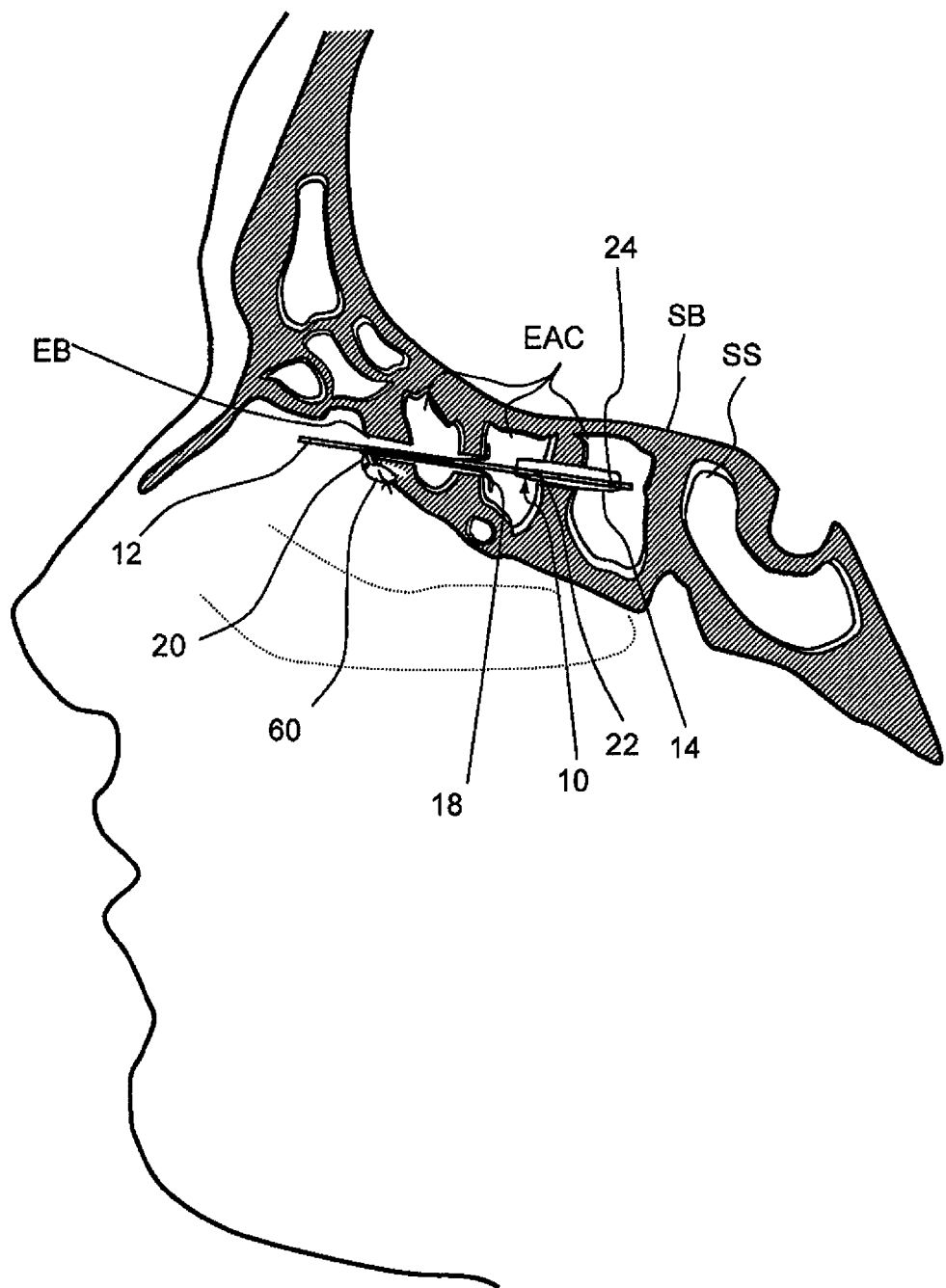

Initially, as seen in FIG. 3A, the needle sheath 40 is located on the needle 49 as shown in FIG. 2D. In this embodiment, the inner diameter of the proximal sheath portion 42 is large enough to allow the moveable sheath 30 of the substance delivery device (shown in FIGS. 1D and 1E) to pass therethrough, whereas the internal diameter of the distal sheath portion 43 is the same or smaller than the outer diameter of the moveable sheath 30 but still sufficiently large in diameter to allow the collapsed reservoir 14 and non-deployed projections 18 to pass thereinto.

The subject is anesthetized or appropriate analgesia/sedation is administered. As shown in FIG. 3A, the needle sheath 40/needle 49 combination is then inserted through the subject's nostril and the needle tip 50 is pushed through the ethmoid bulla EB and into one or more ethmoid air cells EAC. The approximately thirty three degree angle 52 formed in this embodiment of the sinus needle 49 allows the distal tip 50 of the needle 49 to be advanced on a trajectory that is substantially parallel to (or in some cases even divergent from) the adjacent skull base SB and cranial vault CV.

In some cases, the needle sheath 40/needle 49 combination is attached to an image guidance adapter 150 as described above and an optical or electromagnetic image guidance or surgical navigation system may be used to monitor or guide the advancement of the needle tip 50.

Along with or in lieu of such image guidance, an endoscope such as a Hopkins II 4 mm zero degree or thirty degree endoscope from Storz may be inserted into the nostril along side of the sheath 40/needle 49 combination and such endoscope may be used to visualize the placement and advancement of the needle tip 50. The visual marker band 46 (FIG. 2A) on the proximal tube portion 42 of sheath 40 and the colored marker on the tapered step-down segment 45 (FIG. 2A) may also be visualized endoscopically. The distance between the proximal and radiographic markers 44 is substantially the same as the length of the reservoir 14 and such markers 44 may be viewed by fluoroscopy. The surgeon can use such fluoroscopic image to position the markers 44 such that they demarcate the locations where the proximal and distal ends of the reservoir 14 are intended to reside.

As shown in FIG. 3B, after the sheath 40 has been placed in the desired position, the needle 49 is withdrawn leaving the sheath 40 in place with the proximal end of the sheath 40 extending out of the subject's nostril.

Figure 1F:
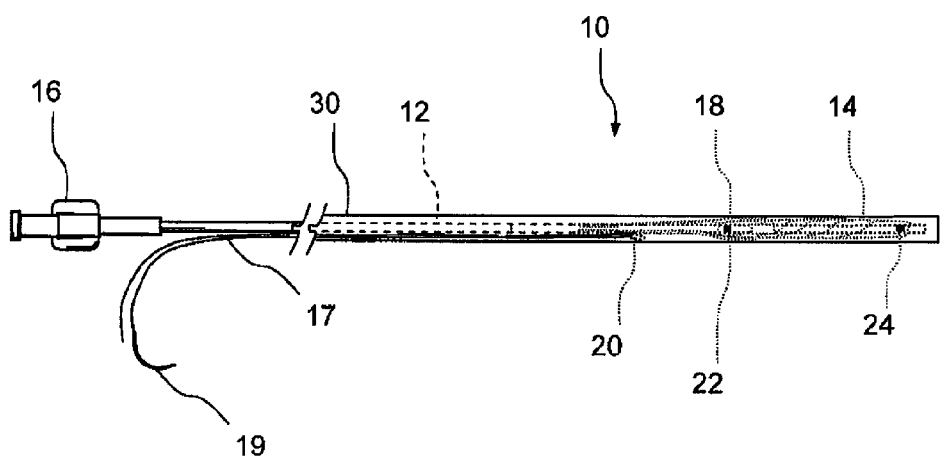
FIG. 1F is a side view of the substance delivery device of FIG. 1A with an optional moveable sheath in its delivery position with a suture pre-loaded through an optional suture loop.

As seen in FIG. 1E, prior to insertion of the substance delivery device 10, the physician will advance the constraining sheath 30 to expose suture loop 20. A length of 2-O or 3-O suture material 17 having a straight or curved needle 19 is then passed through suture loop and doubled over. The constraining sheath 30 is them retracted such that the ends of the suture 17 protrude out of the proximal end of the constraining sheath 30 as shown in FIG. 1F. The uninflated substance delivery device 10 with the optional constraining sheath 30 in its first position (shown in FIG. 1F) is then inserted into the proximal end of the needle sheath 40 (FIG. 3C).

As seen in FIG. 3D, the substance delivery device 10 with the optional constraining sheath 30 in its first position is advanced through the sinus needle sheath 40 to a position where slight resistance to further advancement is felt due to abutment of the distal end of the moveable constraining sheath 30 with an internal surface of the step-down segment 45.

Thereafter, as shown in FIG. 3E, the surgeon will apply sufficient force to overcome the resistance to advancement, causing the moveable constraining sheath 30 to move proximally to its second position (shown in FIG. 1D) and the distal portion of the device 10 including the collapsed reservoir 14 to advance into the distal sheath portion 42. The positioning of the reservoir 14 within the distal sheath portion 42 may then be verified fluoroscopically by viewing the positions of the radiographic marker 24 on the device 10 relative to the positions of the radiographic markers 44 on the distal sheath portion 42. Also, using these markers, the actual positioning of the reservoir 14 relative to the surrounding anatomy may be checked.

Thereafter, as shown in FIG. 3F, the sinus needle sheath 42 with the constraining sheath 30 contained therein may be withdrawn proximally, allowing the projections 18 to spring outwardly so as to engage the adjacent septal walls between ethmoid air cells EAC (or alternatively the internal wall surface of the EB) and also allowing the suture loop 20 to be exposed within the nasal cavity adjacent to the ethmoid bulla EB.

Thereafter, as seen in FIG. 3G, the reservoir 14 is filled with the desired substance, causing the reservoir 14 to assume an expanded configuration. This may be accomplished by attaching a syringe to the proximal Luer connector 16 and infusing the desired substance from that syringe, through the lumen of shaft 12 and into reservoir 14.

Thereafter, as shown in FIG. 3H, the shaft 12 adjacent to proximal Luer connector 16 is cut thereby removing the Luer hub 16. This allows the sinus needle sheath 42 with the constraining sheath 30 contained therein to be removed.

As shown in FIG. 3J, the sinus needle sheath 42 with the constraining sheath contained therein is removed and the suture 17 is used to attach suture loop 20 to adjacent tissue, such as the mucosa M of the intranasal septum or that covering the nasal surface of the ethmoid bulla EB.

Thereafter, as seen in FIG. 3K, the shaft 12 is cut at separation mark 15, and the proximal shaft 12a is removed.

As seen in FIG. 3L, this procedure results in an ethmoidotomy channel or opening extending into one or more ethmoid air cell(s) EAC with the substance eluting reservoir 14 and distal shaft 12b remaining in place for a period of time (e.g., between 1 hour to 90 days, preferably between 7 to 29 days, most preferably about 14 days and in some cases about 7 days) following the performance of the needle ethmoidotomy procedure.

In this ethmoid example, the sinus needle sheath 40 has a distal shaft portion 43 made of Nylon having an outer diameter of 0.087 inches and inner diameter of 0.075 inches and length of 25 mm. Intermediate step down region 45 is made of 5 mm and is tapered from an outer diameter of 0.104 inches and an inner diameter of 0.088 inches at its proximal end, to an outer diameter of 0.092 inches and an inner diameter of 0.075 inches at its distal end. Proximal shaft portion 42 is made of Nylon 12 and has an outer diameter of 0.102 inches and inner diameter of 0.088 inches and length of 3.5 inches. Distal and proximal sheath markers 44 are made of rings of a Pt—Ir alloy with an outer diameter of 0.087 inches and an inner diameter of 0.085 inches. The distal shaft marker 44 is located 1 mm from the distal end DE of needle sheath 134.

Proximal shaft marker 148 is located 18 mm from the distal end of needle sheath 40. The total length of needle sheath 40 is 115 mm.

Although the example of FIGS. 3A-3L is specific to treatment of ethmoid disease, it is to be appreciated that the system of devices shown in the example of FIGS. 3A-3L may be used after various types of sinus surgery, such as functional endoscopic sinus surgery or balloon dilatation of the sinus ostia involving the frontal, maxillary or sphenoid sinuses. Substance delivery device 10 can be used simply as a spacer to maintain a patent opening to various sinus ostia for a desired duration after surgery and/or may also function as a substance delivery device to deliver any diagnostic or therapeutic substance. In the treatment of sinus disease, steroids such as Kenalog®-40 (Triamcinolone Acetonide Injectable Suspension, USP) are delivered to a paranasal region such as the ethmoid sinuses with device 10.

The implantable device 10 can be used to preferably deliver fluids or suspensions with a low surface tension. Fluids with low surface tension easily spread across a surface. This is especially useful to deliver substances over a large surface area, especially in anatomical regions such as ethmoid sinuses that have complicated 3-D geometries. In one embodiment, the low surface tension fluid comprises a surfactant. In one method embodiment, a low surface tension irrigating fluid containing one or more substances is delivered to the ethmoid sinuses. In some embodiments, a substantially inert fluid such as saline solution may be delivered to moisten the surrounding tissues and the device may perform a spacing and/or drainage/ventilation function. In other embodiments, an active substance such as a therapeutic or diagnostic substance may be delivered in addition to the spacing and/or drainage/ventilation function of the implanted device 10.

Figure 4:
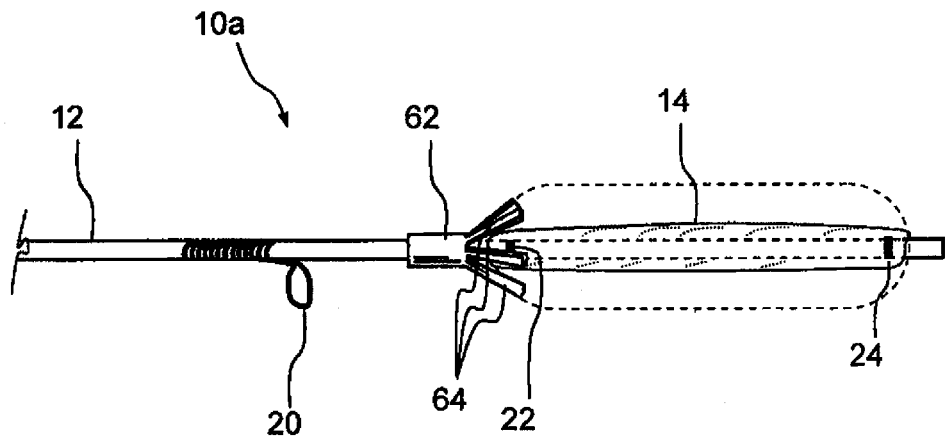
FIG. 4A shows another embodiment of an implantable substance delivery device of the present invention wherein the position maintaining members comprise a suture ring and a splayable tube.
FIG. 4B shows another embodiment of an implantable substance delivery device of the present invention wherein the position maintaining members comprise a plurality of arms extending outwardly from a central hub.
FIG. 4C is a perspective view of the device of FIG. 4B positioned within the nasal cavity of a subject.
FIG. 4D shows another embodiment of an implantable substance delivery device of the present invention wherein the position maintaining member comprises a resilient loop.
FIG. 4E is a schematic showing of the device of FIG. 4D positioned within a subject's body with its reservoir filled with substance and its position maintaining member (i.e., resilient loop) engaging an adjacent anatomical structure.
FIG. 4F is a schematic showing of the device of FIG. 4D being removed from a subject's body with its reservoir substantially empty and its position maintaining member (i.e., resilient loop) being deformed by the pulling force used for removal.
FIG. 4G shows another embodiment of an implantable substance delivery device of the present invention wherein the position maintaining member comprises a tab that may be attached (e.g., sutured) to an adjacent anatomical structure.
FIG. 4H shows another embodiment of an implantable substance delivery device of the present invention wherein the position maintaining member comprises a slotted tube with an outwardly bowed mid-section to facilitate attachment of the device to an adjacent anatomical structure by a suture or other connector.
FIG. 4I shows a slotted tube that may be attached to an implantable substance delivery device of the present invention to facilitate attachment of the substance delivery device to an adjacent anatomical structure by a suture or other connector.
FIG. 4J shows a notched tube that may be attached to an implantable substance delivery device of the present invention to facilitate attachment of the substance delivery device to an adjacent anatomical structure by a suture or other connector.
FIG. 4K shows another embodiment of an implantable substance delivery device of the present invention wherein the position maintaining member comprises a perforated tab.
FIG. 4L is a cross-sectional view through line 4M-4M of FIG. 4K.
FIG. 4M shows another embodiment of a substance delivery device of the present invention during the implantation process, wherein the position maintaining member comprises an expandable sponge.
FIG. 4N shows the device of FIG. 4M in an implanted configuration with its expandable sponge expanded.
FIG. 4O shows another embodiment of a substance delivery device of the present invention during the implantation process, wherein the position maintaining member comprises another expandable sponge.
FIG. 4P shows the device of FIG. 4O in an implanted configuration with its expandable sponge expanded.
Figure 4:
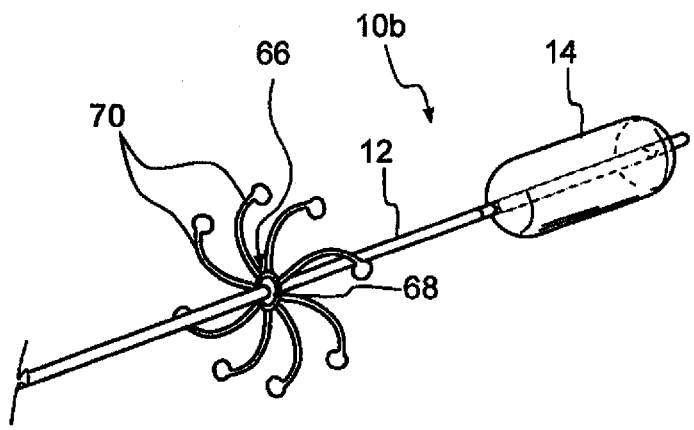
Figure 4:
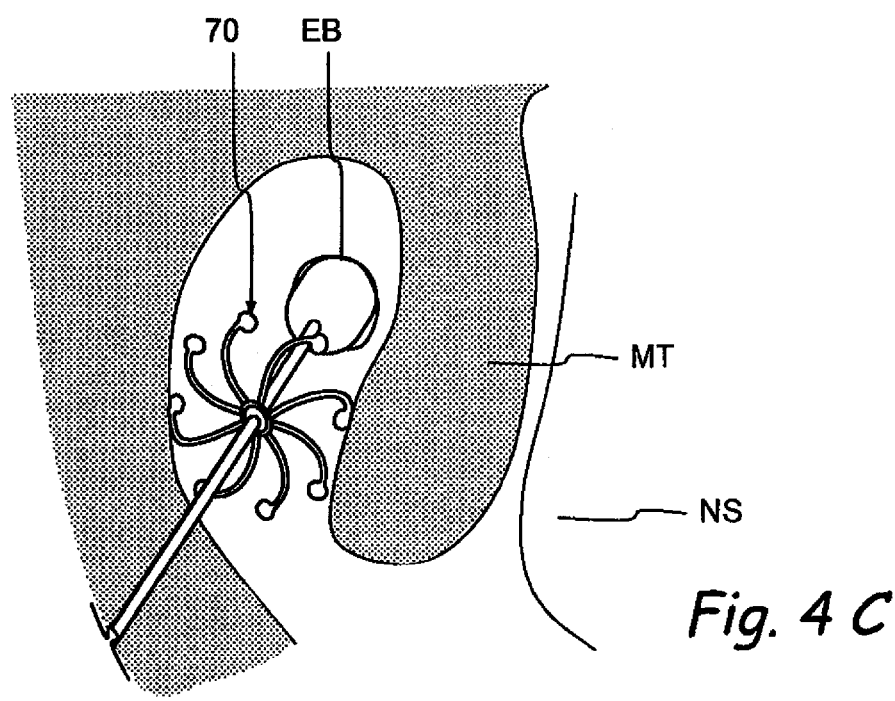
Figure 4:
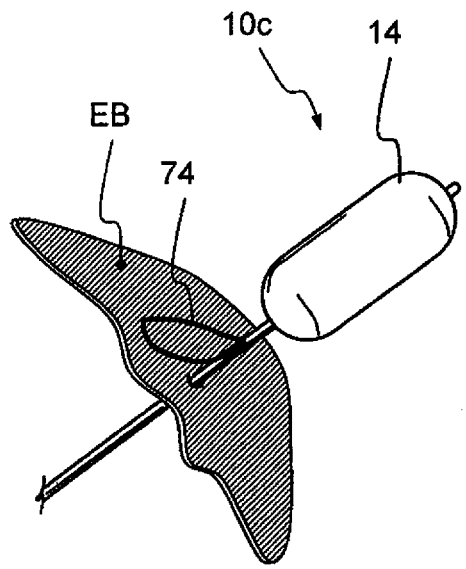
Figure 4:
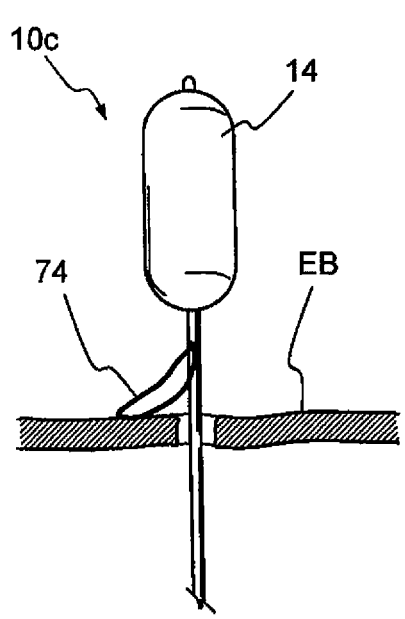
Figure 4:
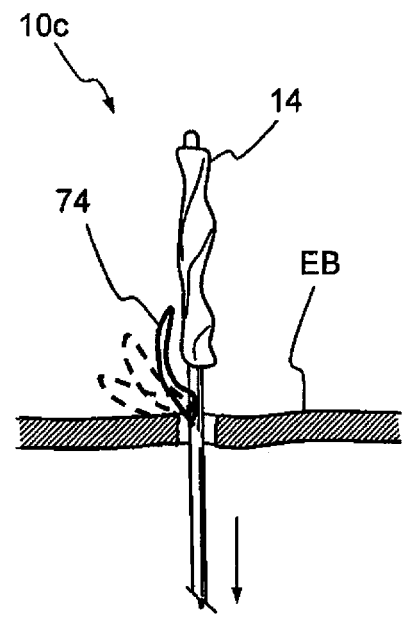
Figure 4:
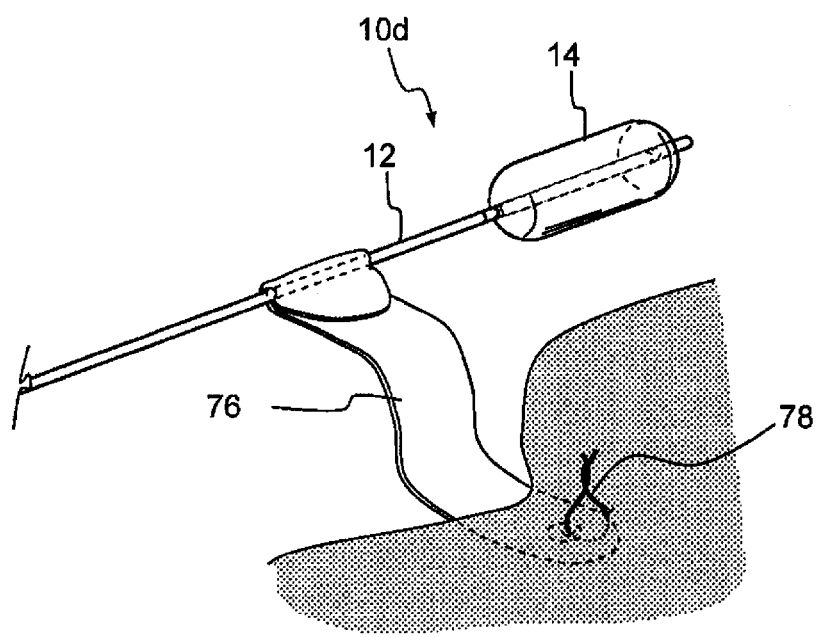
Figure 4:
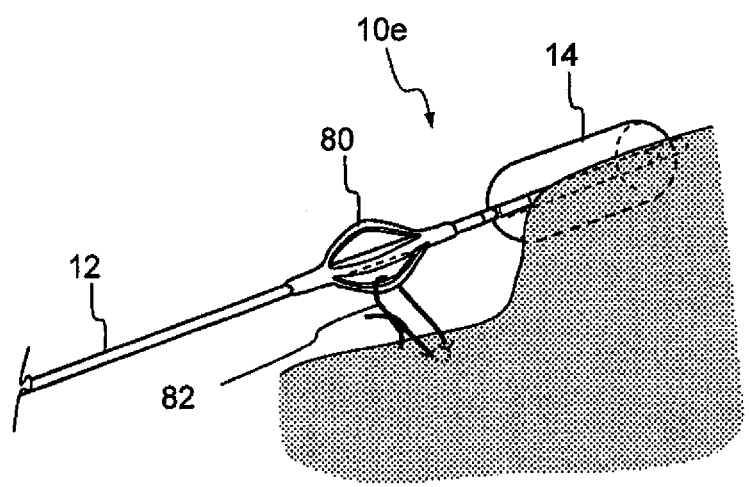
Figure 4:
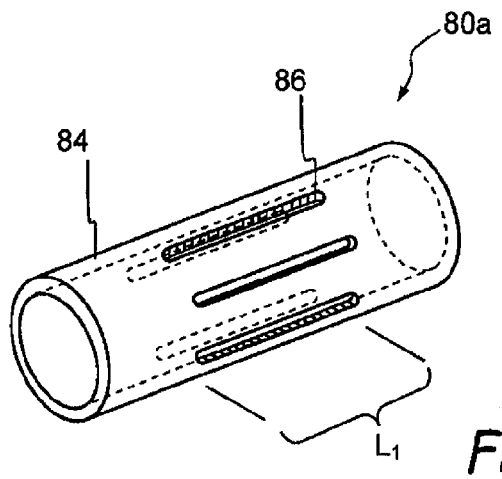
Figure 4:
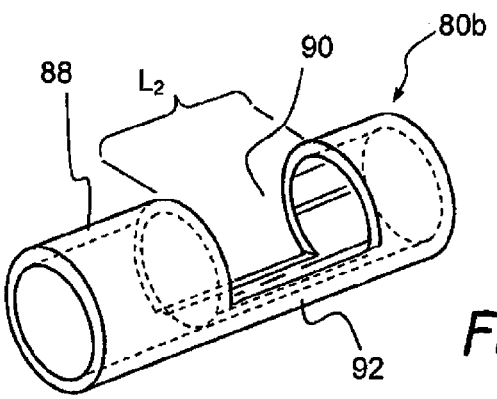
Figure 4:
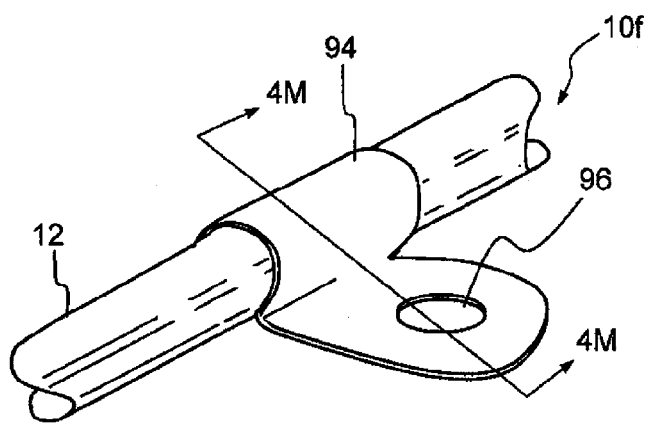
Figure 4:
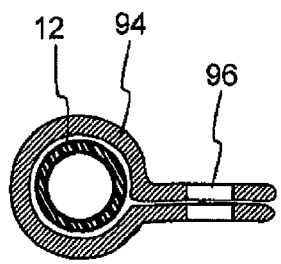
Figure 4:
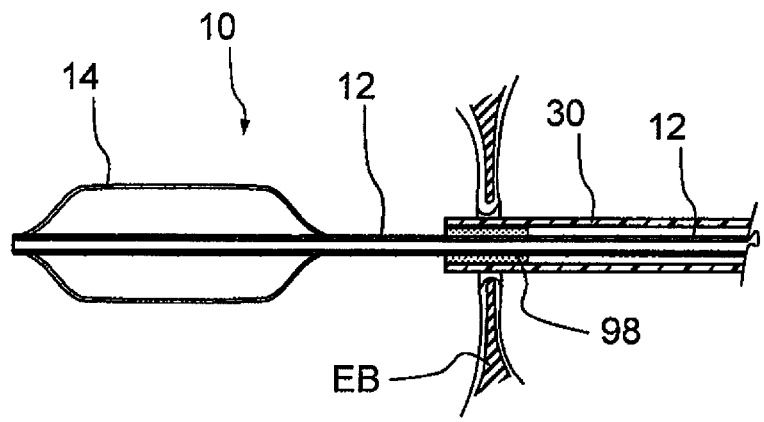
Figure 4:
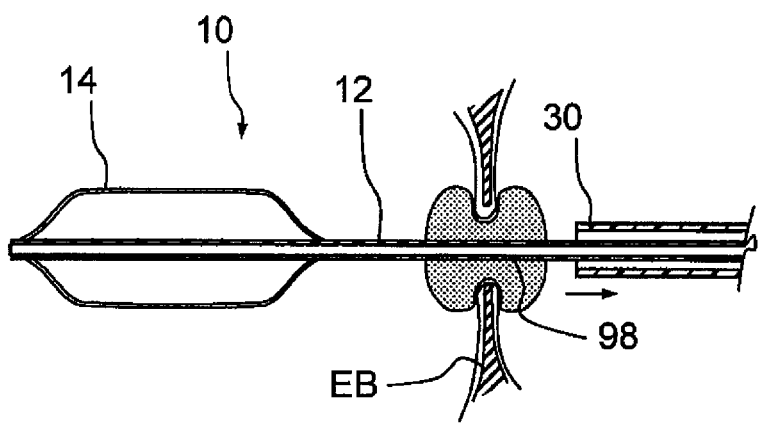
Figure 4:
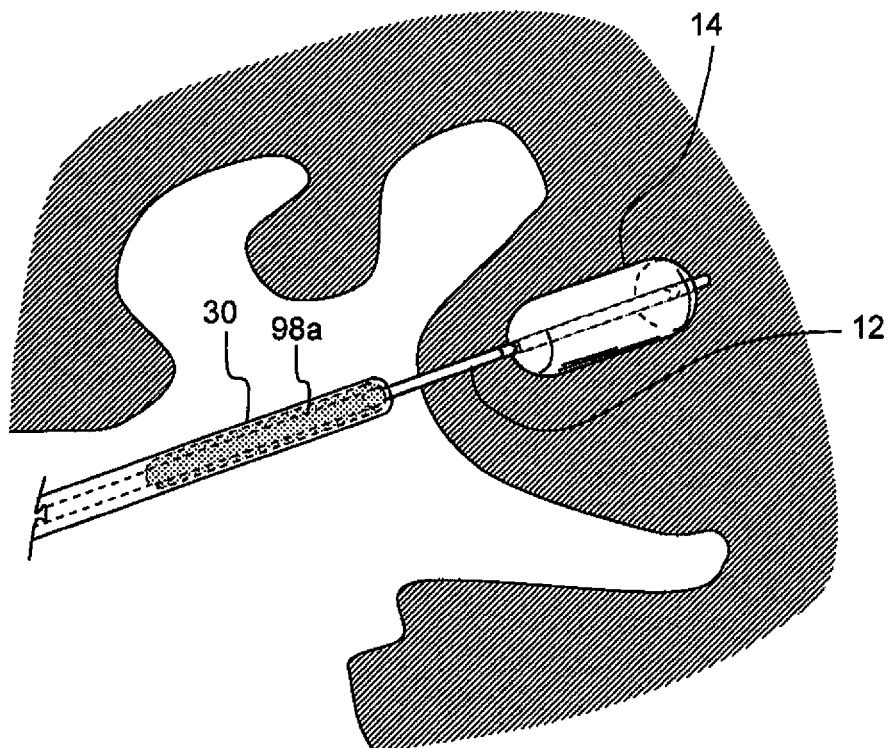
Figure 4:
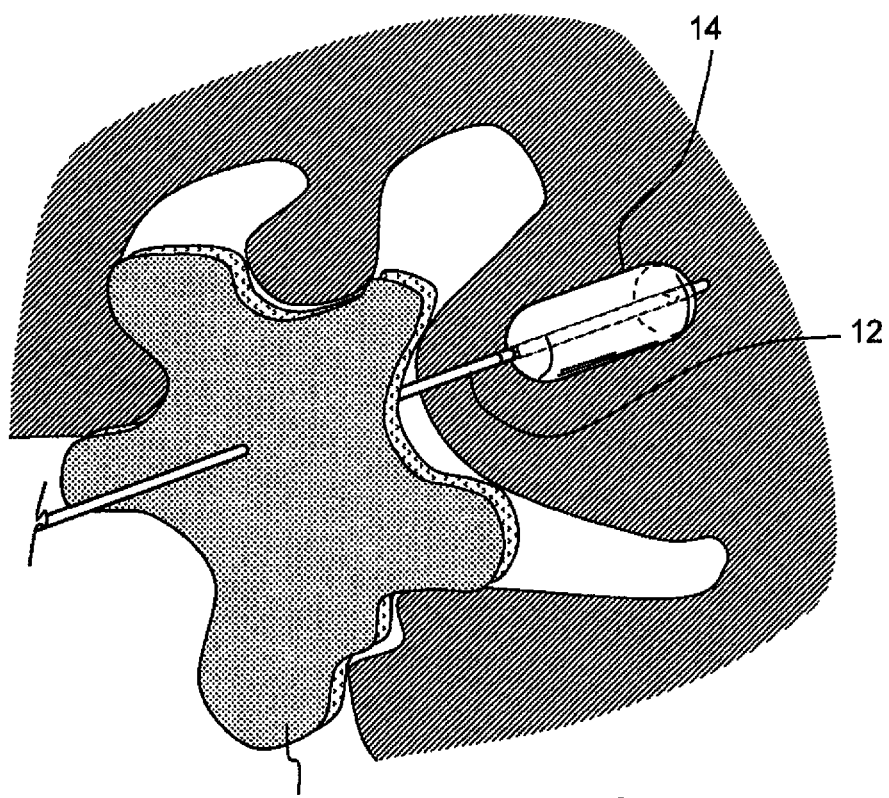

FIGS. 4A-4P show various embodiments of the implantable spacer or substance delivery devices of the present invention having various alternative position maintaining members that engage, abut or attach to adjacent anatomical structure(s) to substantially maintain the device, or a portion of the device (e.g., its reservoir 14), at a desired position within the body.

FIG. 4A shows a side view of a substance delivery device 10a having an anchoring mechanism made of a tube 62 with multiple slots formed therein to create one or more radially projecting arms 64. Other components of this substance delivery device 10a are the same as those described above with respect to the substance delivery device 10 of FIG. 2A. In this device 10a, the radially projecting arms 64 have a sufficient elasticity to allow them to be collapsed or flattened against the collapsed reservoir 14 during the insertion or removal of substance delivery device 10a into the anatomy. Thereafter, radially projecting arms 64 open in a radial direction and increase the overall profile of substance delivery device 10a. This anchors substance delivery device 10a in the anatomy. Distally slotted tube 64 can be made of suitable biocompatible materials including, but not limited to, Nitinol (Nickel-titanium alloy), stainless steel, MPN35 or elgiloy.

FIG. 4B shows a view of a substance delivery device 10b having an anchoring mechanism 66 made of a central hub 68 with multiple radially projecting arms 70. Radially projecting arms 70 may optionally have atraumatic tips such as balls or rounded tips as shown in FIG. 4B. This anchoring mechanism 66 can be slid over shaft 12 to position the anchoring mechanism 66 at a desired location. FIG. 4C shows a view of the nasal cavity showing the substance delivery device 10b of FIG. 4B inserted in an ethmoid sinus. As shown in FIG. 4C, radially projecting arms 70 wedge against two or more surrounding anatomical regions such as nasal septum NS, ethmoid bulla EB, middle turbinate MT, etc. and anchor substance delivery device 10b to the anatomy. Radially projecting arms 70 have a sufficient elasticity to enable a user to flatten them against shaft 12 (e.g., by advancement of optional sheath 30) during the insertion or removal of this delivery device 10b. Radially projecting arms 70 can be made of suitable biocompatible materials including, but not limited to, Nitinol (nickel-titanium alloy), stainless steel, MPN35, or elgiloy.

FIGS. 4D-4F show another embodiment of an implantable substance delivery device 10b wherein the position maintaining member comprises an elastic loop 74 which is biased to an extended position whereby it will frictionally engage an adjacent anatomical structure (e.g., the ethmoid bulla EB (or alternatively an intra-ethmoid septum that has been penetrated) to substantially hold the reservoir 14 at the desired location (e.g., within one or more ethmoid air cell(s) that have been opened by an ethmoidotomy of the present invention or other appropriate procedure known in the art). This elastic loop 74 may be formed of nickel titanium alloy or other suitable elastic or superelastic material. As shown in FIG. 4E, the elastic loop 74 is sufficiently resilient to hold the device 10c in the desired implantation location but, as seen in FIG. 4F, will bend or flatten to allow the device 10c to be extracted or removed. As explained herein, elastic loop 74 may be constructed such that the force required to accomplish such retraction or removal of the device 10c does not cause clinically significant injury or disruption of healing of the surrounding tissues. In applications where the device 10c is implanted in ethmoid air cell(s), a force of less than approximately 0.5 pounds is generally desirable to avoid such clinically significant injury or disruption of healing.

In some embodiments of the invention, the position maintaining member(s) may comprise members that may be sutured or otherwise attached to adjacent anatomical structure(s), such as the optional suture loop 20 of the implantable device 10 shown in FIG. 1. It will be appreciated that various suturable or attachable members, other than a loop 20, may be used for this purpose, including but not limited to the examples shown in FIGS. 4G-4L.

For example, FIG. 4G shows a view of a paranasal region showing a substance delivery device 10d having a flexible suturable strip or tab 76 which may be made of suitable biocompatible material including, but not limited to, woven fabrics such as silicone, PEBAX, nylon, etc. A user can pass suture through flexible suturable strip or tab 76 thereby securing substance delivery device 10d to an adjacent anatomical structure 78. Optionally, as shown in FIG. 4G, a hole through which suture can pass may be formed in the strip or tab 76. Alternatively, the strip or tab 76 may be formed of needle-penetrable material to allow a suture needle to be passed therethrough.

FIG. 4H shows another variation of the device 10e wherein the position maintaining member comprises a slitted tube 80. Slitted tube 80 has a proximal end, a distal end and a series of parallel slits oriented along its longitudinal axis. This slitted tube 80 is advanced over shaft 12 to a desired position. Thereafter, one end of the slitted tube 80 is attached to the shaft 12, by way of adhesive or heat shrinking, for example. Thereafter, the other end of slitted tube 80 may be advanced toward the affixed end of the slitted tube 80 causing the portions of the slitted tube 80 between the slits to bow outwardly, as shown. That end of the slitted tube 80 is then also affixed to the shaft. A suture 82 may then be passed through adjacent slits in the tube 80 and tied to an adjacent anatomical structure as shown in FIG. 4H.

FIG. 4I shows another type of slotted tube position maintaining member 80a that may be used to hold the implantable device 10 in place. In this example, the position maintaining member comprises an elastomeric tube 84 having circumferentially spaced slots 86 of length L1 formed therein. The ends of this tube 84 are affixed to the shaft 12 and the regions of the tube 84 between the slots 86 are sufficiently elastic to be lifted away from the underlying shaft 12 to allow the suture 17 to be passed in one slot 86 and out of an adjacent slot 86.

FIG. 4J shows another type of slotted tube position maintaining member 80a that may be used to hold the implantable device 10 in place. In this example, the position maintaining member comprises a tube 88 having a notch 90 formed in one side thereof. One end of this tube 88 is affixed to the shaft 12 and the region 92 is sufficiently flexible to be lifted away from the underlying shaft and the non-affixed end slides over the shaft to allow the suture 17 to be passed in between region 92 and the underlying shaft portion.

FIG. 4K shows a region of the shaft 12 of implantable device 10 with another embodiment of a position maintaining member 94 attached thereto. This position maintaining member comprises a perforated tab 96 and is made from a strip of heat shrink material. The material is folded around elongate shaft 12. Thereafter, the free ends of the strip are heat fused to each other to form the tab 96 and a hole in punched in the tab 96. FIG. 4L shows a section through line 4L-4L of FIG. 4L. A suture 17 or other connector may be passed through the hole in the tab 96 and secured to an adjacent anatomical structure.

In some embodiments, the position maintaining member can comprise a space occupying member that swells, expands, deploys or moves in order to frictionally engage (e.g., contact, abut, press against, etc.) the adjacent anatomical structure(s). Examples of such are shown in FIGS. 4M-4P. For example, in FIGS. 4M and 4N, a self-expanding member 98 that will conform to a surrounding shape, such as a mass of resilient polymer foam, is attached to the shaft 12 of the implantable device 10. Initially, as seen in FIG. 4M, the constraining sheath 30 is advanced over this self-expanding member 98 to hold it in a compressed state that is small enough to be positioned within an opening in the ethmoid bulla EB or other anatomical location (e.g., a natural or man made sinus opening, ostium, etc.). Thereafter, as seen in FIG. 4N, the constraining sheath 30 is retracted thereby releasing constraint from the self-expanding member 98 and allowing the self-expanding member 98 to expand into contact and conformity with the surrounding anatomy. In this example, the self-expanding member 98 conforms to the surrounding portion of the ethmoid bulla EB thereby maintaining the reservoir 14 within a channel that has been created in one or more diseased ethmoid air cells. FIGS. 4O and 4P show a similar example where the self expanding member 98a comprises a foam or other swellable material that absorbs endogenous fluid (e.g., blood) or introduced fluid (e.g., saline) causing it to swell to fill a body cavity and to frictionally engage the adjacent wall(s) of that body cavity.

Figure 5:
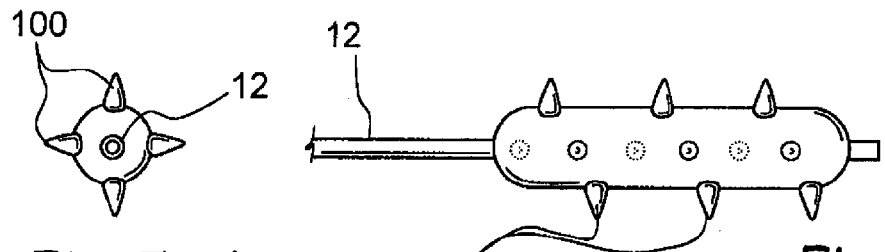
FIG. 5A is a partial side view of another embodiment of an implantable substance delivery device of the present invention wherein the position maintaining members comprise conical spikes on the outer surface of the reservoir.
FIG. 5B is a partial side view of another embodiment of an implantable substance delivery device of the present invention wherein the position maintaining members comprise arcuate fins on the outer surface of the reservoir.
FIG. 5C is a partial side view of another embodiment of an implantable substance delivery device of the present invention wherein the position maintaining members comprise circumferential fins on the outer surface of the reservoir.
FIG. 5D is a partial side view of another embodiment of an implantable substance delivery device of the present invention wherein the position maintaining members comprise circumferential fins of varied diameter on the outer surface of the reservoir.
FIG. 5E is a partial side view of another embodiment of an implantable substance delivery device of the present invention wherein the position maintaining member comprises a tapered outer wall of the reservoir.
FIG. 5F is a partial side view of another embodiment of an implantable substance delivery device of the present invention wherein the position maintaining members comprise filaments on the outer surface of the reservoir.
FIG. 5G is a partial side view of another embodiment of an implantable substance delivery device of the present invention wherein the position maintaining members comprise cupped flanges on the outer surface of the reservoir.
FIG. 5H is a partial side view of another embodiment of an implantable substance delivery device of the present invention wherein the position maintaining members comprise bumps on the outer surface of the reservoir.
FIG. 5I is a partial side view of another embodiment of an implantable substance delivery device of the present invention wherein the position maintaining members comprise linear arrays of rectangular fins on the outer surface of the reservoir.
FIG. 5J is a partial side view of another embodiment of an implantable substance delivery device of the present invention wherein the position maintaining members comprise slit fins on the outer surface of the reservoir.
FIG. 5K is a partial side view of another embodiment of an implantable substance delivery device of the present invention wherein the position maintaining members comprise perpendicular projections on the outer surface of the reservoir.
FIG. 5L is a partial side view of another embodiment of an implantable substance delivery device of the present invention wherein the position maintaining members comprise oblique projections on the outer surface of the reservoir.
FIG. 5M is a partial side view of another embodiment of an implantable substance delivery device of the present invention wherein the position maintaining member comprises a helical fin on the outer surface of the reservoir.
FIG. 5N is a partial side view of another embodiment of an implantable substance delivery device of the present invention wherein the position maintaining member comprises a sponge on the outer surface of the reservoir.
Figure 5:
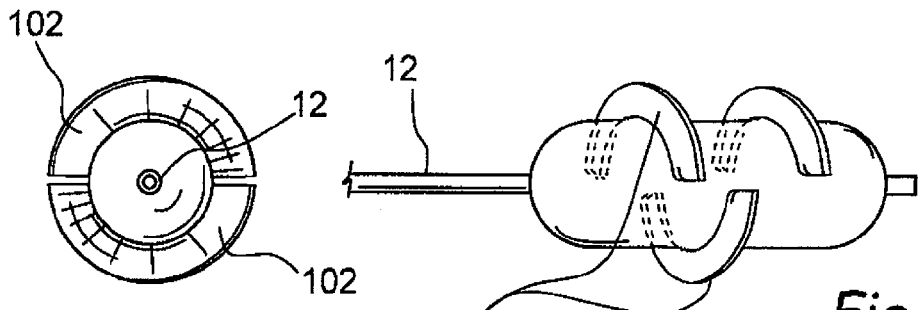
Figure 5:
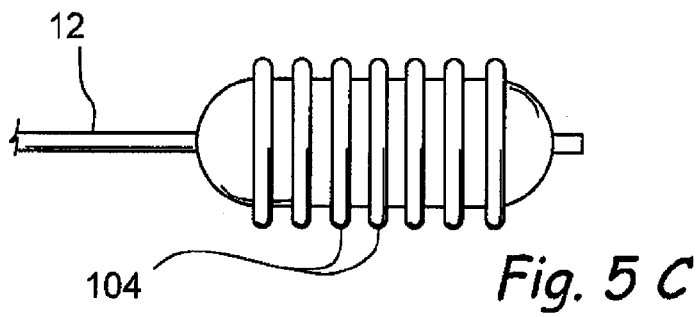
Figure 5:
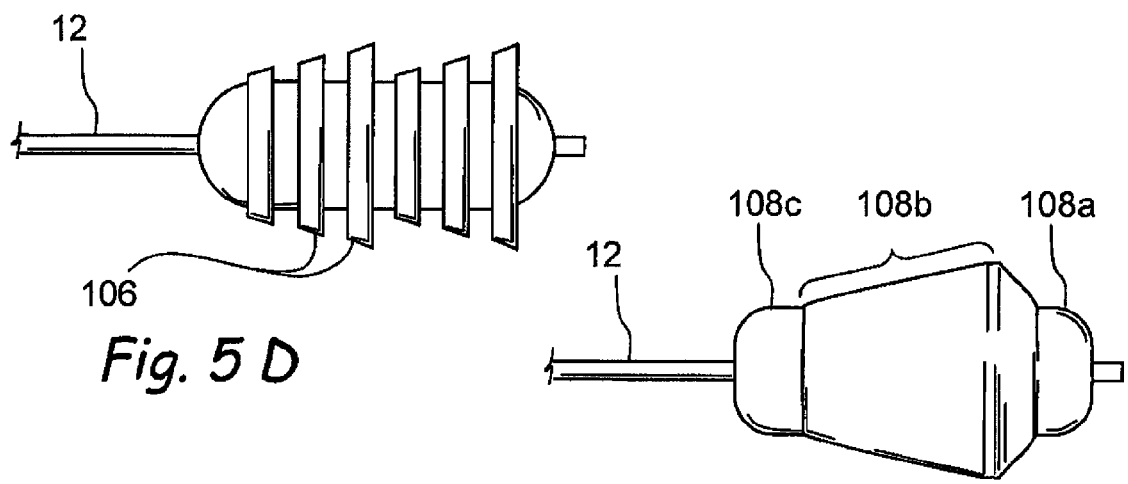
Figure 5:
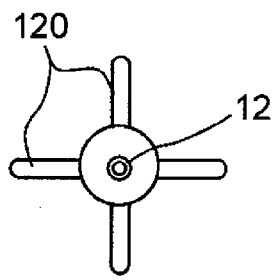
Figure 5:
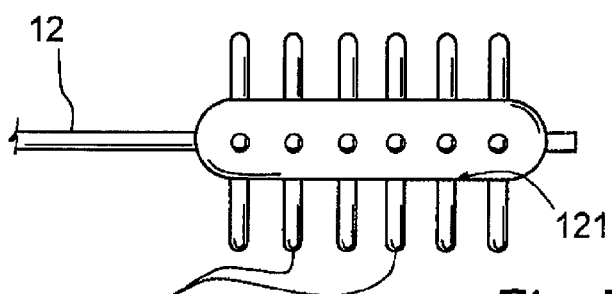
Figure 5:
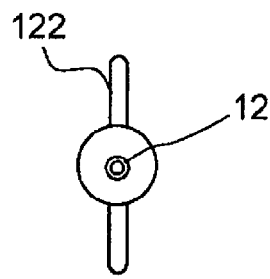
Figure 5:
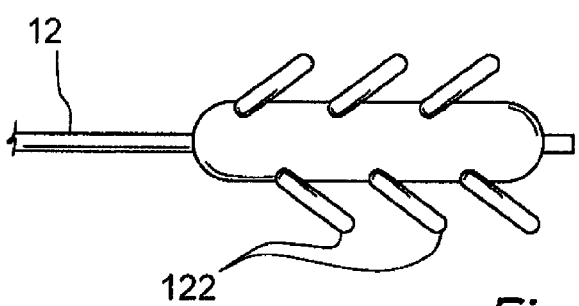
Figure 5:
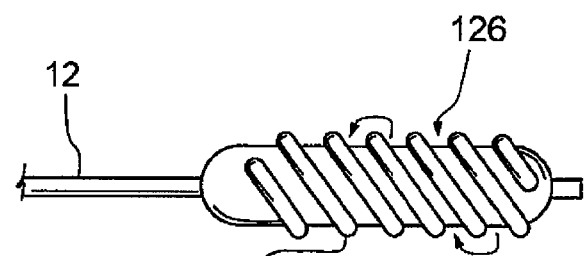
Figure 5:
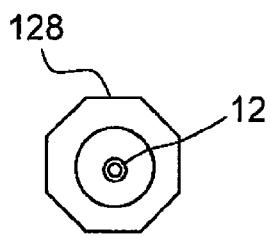
Figure 5:
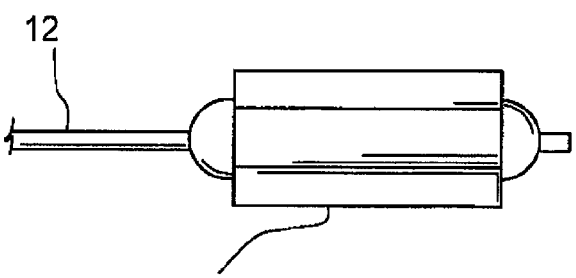

In some embodiments, the position maintaining member may comprise surface features or projections that are formed on the shaft 12, on an enlarged region of the shaft 12, or on the expandable reservoir examples of which are shown in FIGS. 5A through 5N.

Specifically, FIGS. 5A and 5A' show radial projections 100 arranged on an enlarged region of the shaft 12 in a desired pattern such as a helical or staggered pattern FIGS. 5B and 5B' show multiple arcuate ridges 102 forming a broken helical pattern on an enlarged diameter region of the shaft 12.

FIG. 5C shows an embodiment where a series of spaced-apart circumferential ribs 104 or equivalent are formed on an enlarged diameter region of the shaft 12.

FIG. 5D shows an embodiment where a series of spaced-apart circumferential ribs 106 of varying diameter are formed on an enlarged diameter region of the shaft 12.

FIG. 5E shown an embodiment wherein a position maintaining member comprises a tapered plug formed on the shaft 12, such tapered plug comprising end portions 108a and 108c having generally cylindrical side walls and a midportion 108b having a tapered side wall that is configured to seat within or engage an anatomical opening or structure.

FIGS. 5F and 5F' show an embodiment having multiple hair like projections such as filaments or wires extending outwardly from an enlarged diameter region 141 of shaft 12 so as to frictionally engage a surrounding surface or structure.

FIGS. 5G and 5G' show an embodiment having a plurality of anchoring cups 112 extending about an enlarged region of the shaft 12. Each anchoring cup 112 is stiff enough to enable anchoring of the device in a desired anatomical region, but flexible enough to bend while introducing and advancing the device to the desired position or when subsequently removing the device.

FIG. 5H shows a device where multiple bumps 114 are formed on the outer surface of an enlarged diameter region of the shaft 12 to engage the surrounding anatomy.

FIG. 5I shows an embodiment having multiple longitudinally oriented ridges 116 formed on and extending outwardly from an enlarged diameter region of the shaft 12.

FIGS. 5J and 5J' show an embodiment wherein diametrically opposed, longitudinally oriented slitted ridges 188 extend outwardly from an enlarged diameter region of the shaft 12. Each of these ridges 188 is oriented parallel to the longitudinal axis of elongate shaft 112. and has a series of radial slits or cuts formed therein.

FIGS. 5K and 5K' show another embodiment wherein multiple rows of flexible or bendable protrusions 120 extend radially outward from an enlarged region of the shaft. In this particular embodiment, four rows of projections are arranged at 3, 6, 9 and 12 o'clock positions about the circumference of the shaft, as seen in the cross sectional view of FIG. 5K' but, as those of skill in the art will appreciate, many other arrangements of these protrusions are possible.

FIGS. 5L and 5L' show another embodiment wherein multiple diametrically opposed rows of slanted flexible or bendable protrusions 122 extend outwardly from an enlarged region of the shaft. In this particular embodiment, two rows of slanted projections 122 are arranged at 12 o'clock and 6 o'clock positions about the circumference of the shaft 12, as seen in the cross sectional view of FIG. 5L' but, as those of skill in the art will appreciate, many other arrangements of these protrusions are possible.

FIG. 5M shows an embodiment where the position maintaining member comprises a helical ridge 126 that extends about the outer surface of an enlarged diameter region of the shaft 12 to engage surrounding tissues or structures thereby holding, or helping the device in place. In this embodiment, as in various other embodiments of the device, fluids can drain around the shaft 12. In this regard, it will be appreciated that this helical ridge 126 also forms a helical trough or channel through which mucous or other fluids may flow.

FIGS. 5N and 5N' show an embodiment wherein the position maintaining member comprises an octagonal sponge 128 mounted about an enlarged region of shaft 12. Such sponge may self expand or may swell in response to fluid absorption so as to engage adjacent or surrounding anatomy. It will be appreciated that, although the sponge 128 shown in this example is octagonal, various other shapes may alternatively be employed.

FIGS. 5A-5N' show various examples of positioning maintaining members that are formed on enlarged regions of the shaft 12. Such enlarged region may comprise a generally cylindrical body that is either formed integrally of or attached to the shaft 12 in accordance with molding, extrusion and/or fabrication techniques known in the art of medical catheter construction. Also, it will be appreciated that these same position maintaining members could be located on the outer surface of the reservoir 14 as an alternative to, or in addition to, their position on the shaft 12.

Figure 6:
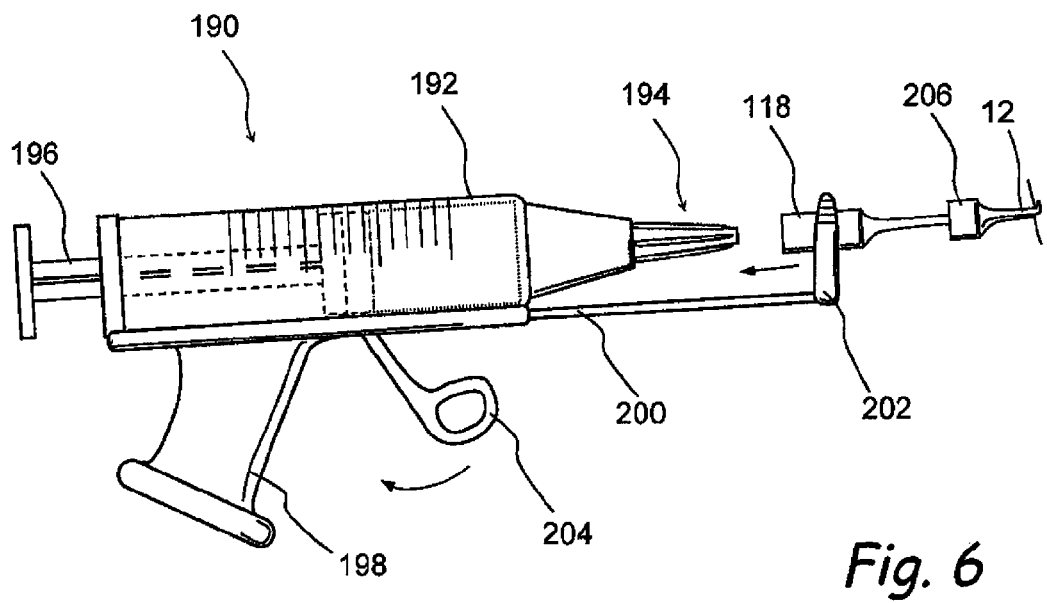
FIG. 6 is a side view of a filling device of the present invention that may be used for in situ filling of the substance delivery and/or spacer devices of this invention.

The substance delivery devices 10 disclosed herein can comprise one or more mechanisms to ensure a fairly uniform delivery of therapeutic substances to the target anatomical regions over a period of time. In some embodiments, the reservoir 14 of the implantable 10 may be initially filled and/or refilled one or more times after it has been inserted into the subjects body and advanced to the desired position. In this manner, the reservoir 14 may be in a substantially collapsed configuration during introduction and positioning in the body and may thereafter assume its expanded or inflated condition as the desired fluid of substance is introduced thereinto. Refilling of the reservoir 14 in situ may present challenges if the shaft 12 has previously been cut off in the manner described above and shown in FIG. 3L such that the free proximal end of the distal shaft 12b resides within the nasal cavity and does not protrude out of the nose where it can be easily accessed. FIG. 6 shows an example of a filling device 190 that may be used to accomplish such in situ refilling. The filling device 190 comprises a syringe body 192 that stores the substance to be filled into substance delivery device 10. Syringe body 192 terminates distally into a syringe nozzle 194. Syringe nozzle 194 is designed to fit into hub 118 of substance delivery device 10. The substance stored in syringe body 192 is delivered to substance delivery device 10 by pressing a plunger 196 connected to syringe body 192. Syringe body 192 is further connected to a handle 198 that enables a user to hold filling device 190 in a hand. Filling device 190 also comprises a grasping arrangement to grasp the proximal region of substance delivery device 10 and align hub 118 in a suitable alignment to insert syringe nozzle 194 into hub 118. In the embodiment shown in FIG. 6, the grasping arrangement comprises a grasping rod 200 that terminates distally in a hook 202. Hook 202 engages the distal region of hub 118 and pulls hub 118 towards syringe nozzle 194. Filling device 190 can be advanced or retracted by a trigger 204 connected to handle 198 along rod 200. Thus, filling device 190 can be operated by a user using a single hand. In a preferred embodiment, elongate shaft 12 of substance delivery device 10 comprises a stopper 206. In a method of refilling substance delivery device 10, the distal region of filling device 190 is inserted into the anatomy such that it lies adjacent to hub 118 of substance delivery device. Thereafter, hub 118 of substance delivery device 100 is engaged by hook 202. Thereafter, trigger 204 is pulled to engage the proximal end of hub 118 with syringe nozzle 194. The user then pushes reservoir compressing member 198 to fill substance delivery device 10 with the substance from syringe body 192. Thereafter, trigger 204 is pushed to disengage the proximal end of hub 118 from syringe nozzle 194. Filling device 190 is then removed from the anatomy. In a preferred embodiment, filling device 190 is designed to enable a user to operate trigger 204 with a forefinger of a hand and operate reservoir compressing member 196 with the thumb of the same hand.

Figure 7A:
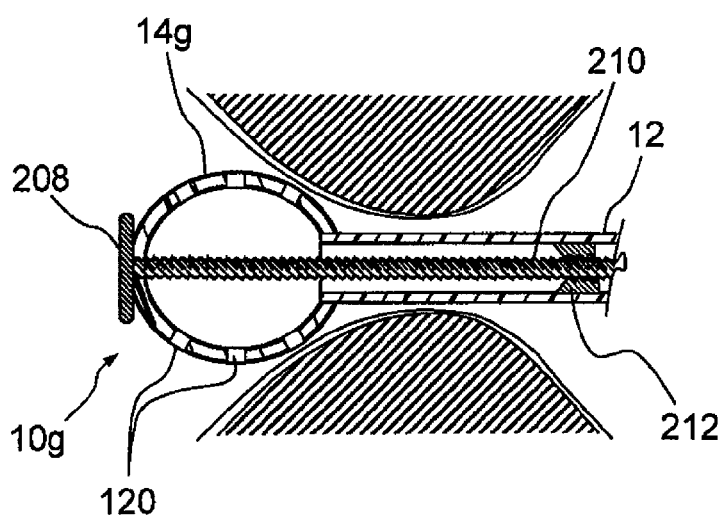
FIGS. 7A and 7B are partial sectional views of another embodiment of an implantable substance delivery device of the present invention.
Figure 7B:
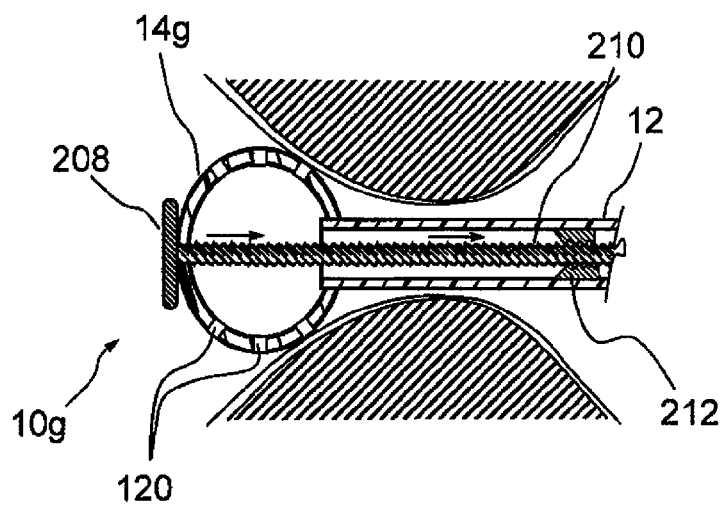

Also, in some instances where it is desired to accomplish sustained release or elution of a substance from an implanted reservoir over a period of time, it is desirable to maintain the reservoir under a substantially constant or at least minimal pressure in order to ensure continual release of the substance. in this regard, FIGS. 7A and 7B show an embodiment of an implantable substance delivery device 10q having a compressible reservoir 14q, a reservoir compressing member 208 and a pull member 210. The pull member 210 may be used to pull the compressing member 208 in a direction that causes compression of the reservoir 14q as the quantity of matter inside the reservoir 14q diminishes. Reservoir compressing member 208 is connected to pull member 210 (e.g., a cord or filament). In the embodiment shown, pull member 210 passes through substance reservoir 14q and through elongate shaft 12. In an alternate embodiment, pull member 210 may lie exterior to substance reservoir 14q and thus will not come into contact with matter contained inside of the reservoir 14q. In FIG. 7B, pull member 210 passes through a unidirectional mechanism 212 such as a ratchet or frictional grasper that allows the pull member 210 to be retracted in the proximal direction but prevents the pull member 210 from moving or slipping substantially in the distal direction. In a preferred embodiment, unidirectional mechanism 212 is a ratchet mechanism. Pull member 210 may further pass through a valve (not shown) to prevent the leakage of the substance stored in substance reservoir 14q through the proximal end of elongate shaft 12. A proximal end of the pull member 210 may be grasped and pulled by the physician or other care giver. This step can be performed for example, in a physician's office during a follow-up visit. This can be done by pulling member pull member 210 in the proximal direction by hand or by a device such as a pair of pincers or tweezers. Reservoir compressing member pull member 210 will in turn pull reservoir compressing member 208 to compress substance reservoir 14q thereby increasing the pressure inside the reservoir 14 to increase, or to maintain consistency of, the rate at which the substance passes outwardly through openings formed in the wall of the reservoir 14q.

Figure 8:
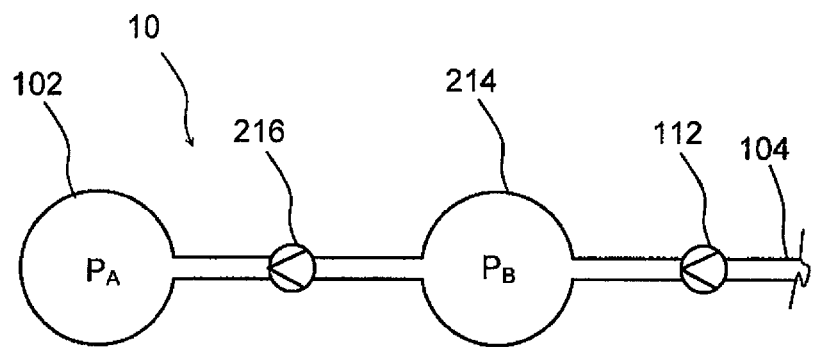
FIG. 8A is a schematic diagram of another embodiment of a substance delivery device of the present invention having a delivery reservoir and a driving reservoir.
FIG. 8B is a graph of pressure versus time, showing the relative changes in pressure within the delivery reservoir and driving reservoir of the device shown in FIG. 8A.
Figure 8:
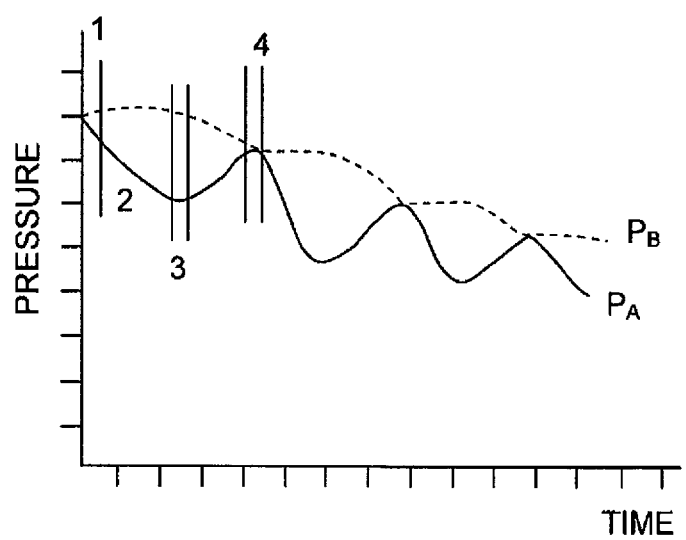

FIG. 8A shows an embodiment of a dual balloon substance eluting device 10r that comprises a substance reservoir 102 that has multiple openings. A substance stored in substance reservoir 102 is delivered to the surrounding anatomy through the multiple openings. Substance reservoir 102 is connected by elongate shaft 104 to a driving reservoir 214. A region of elongate shaft between substance reservoir 102 and driving reservoir 214 has a control valve 216. Control valve 216 prevents the passage of a fluid from substance reservoir 102 to driving reservoir 214. Control valve 216 is designed to open when the pressure $P_B$ in driving reservoir 214 exceeds the pressure $P_A$ in substance reservoir 102 by a certain amount. When this happens, control valve 216 allows the passage of a fluid from driving reservoir 214 to substance reservoir 102 until the pressure $P_B$ in driving reservoir 214 equilibrates with the pressure $P_A$ in substance reservoir 102. In one embodiment, control valve 216 is a duck-bill valve. Other types of valves that can be used as control valve 216 include, but are not limited to, ball valves and flapper valves. Driving reservoir 214 is filled through the proximal end of shaft 104. A region of elongate shaft between substance reservoir 102 and the proximal end of elongate shaft 104 has a valve 112 such as an elastomeric sleeve valve 112 to deter leakage of substance from the open end of the elongate shaft 104.

FIG. 8B is a graph showing the changes in the pressure $P_A$ within substance reservoir 102 and the pressure $P_B$ within driving reservoir 214 after substance delivery device of FIG. 8A has been filled with a suitable substance. At region 1, substance delivery device 100 is filled with a suitable substance through the proximal end of elongate shaft 104. The substance is used to fill both driving reservoir 214 and substance reservoir 102. The substance stored in substance reservoir 102 is delivered to the surrounding anatomy through the multiple openings in substance reservoir 102. After some time, the substance stored in substance reservoir 102 is depleted. This reduces the pressure $P_A$ inside substance reservoir 102 as shown in region 2 on FIG. 8B. This in turn reduces the rate of delivery of the substance into the surrounding anatomy. The pressure $P_A$ inside substance reservoir 102 reduces until the difference between $P_A$ and $P_B$ 102 causes control valve 216 to open, as indicated at region 3 on FIG. 8B. This causes the substance inside driving reservoir 214 to flow into substance reservoir 102 till the pressure $P_B$ in driving reservoir 214 equilibrates with the pressure $P_A$ in substance reservoir 102, which is seen to occur in region 4 on FIG. 9B. Thus the pressure inside substance reservoir 102 is increased. This in turn increases the rate of delivery of the substance into the surrounding anatomy from substance reservoir 102. The steps shown in regions 1 through 4 of FIG. 8B repeat automatically until the substance in driving reservoir 214 is exhausted. Thus the rate of delivery of the substance into the surrounding anatomy is maintained resulting in a more uniform rate of delivery over time. One or both of driving reservoir 214 and substance reservoir 102 may also be used to anchor substance delivery device 100 in the anatomy.

Separately from or in addition to means for controlling or maintaining the pressure within a substance reservoir 14, 102, the rate at which a particular substance elutes from the reservoir 14, 102 and/or the relative efficacy of the eluted substance on adjacent tissues may be controlled or modified in various other ways, including but not limited to a) varying the number and/or size of apertures 31 formed in the reservoir 14, 102 and/or b) using iontophoresis to enhance outflow of substance from the reservoir 14, 102 and passage of the eluted substance (or an active component of the substance) into or through the adjacent mucosa.

Figure 10:
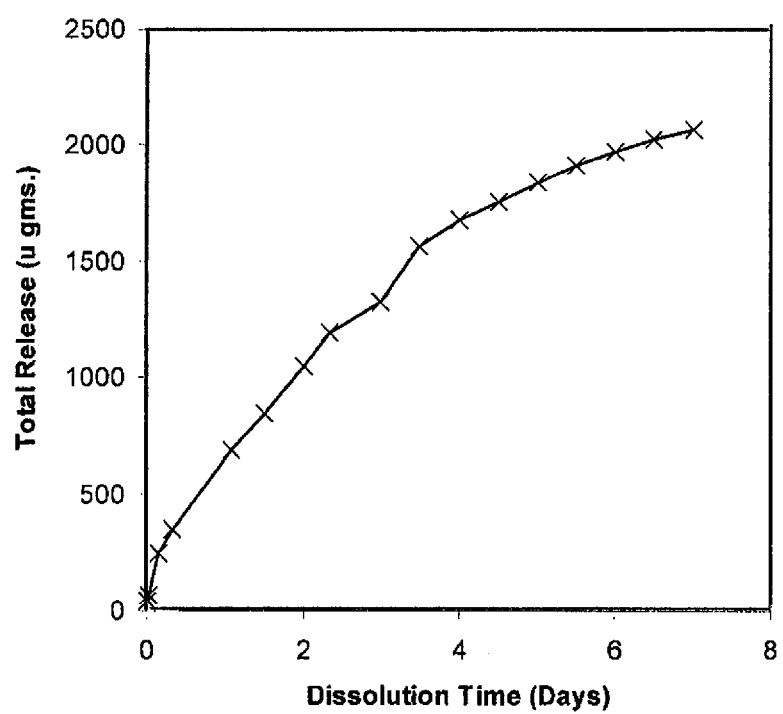
FIG. 10A is a graph showing the total release of Triamcinolone Acetonide from an implantable substance delivery device of the present invention over seven (7) days.
FIG. 10B is a graph comparing the cumulative total release of Triamcinolone Acetonide over a thirty (30) hour period from a) an implantable substance delivery device of the present invention having 768 holes of 30 micron diameter holes formed in its reservoir and b) an implantable substance delivery device of the present invention having 1610 holes of 22 micron diameter holes formed in its reservoir.
FIG. 10C is a graph comparing the cumulative percent of Triamcinolone Acetonide released over a thirty (30) hour period from a) an implantable substance delivery device of the present invention having 768 holes of 30 micron diameter formed in its reservoir and b) an implantable substance delivery device of the present invention having 1610 holes of 22 micron diameter formed in its reservoir.
Figure 10:
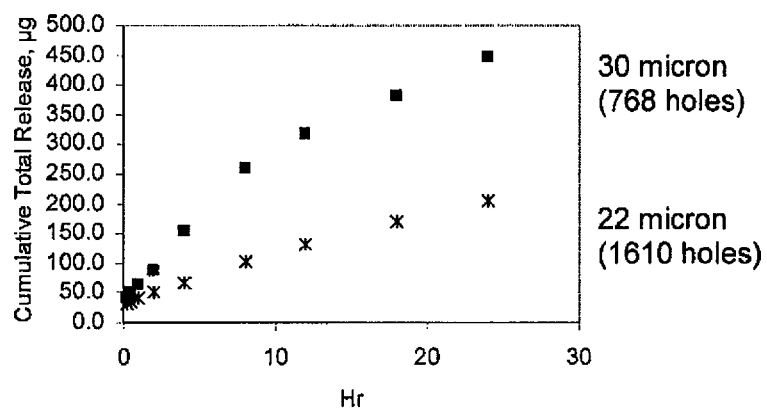
Figure 10:
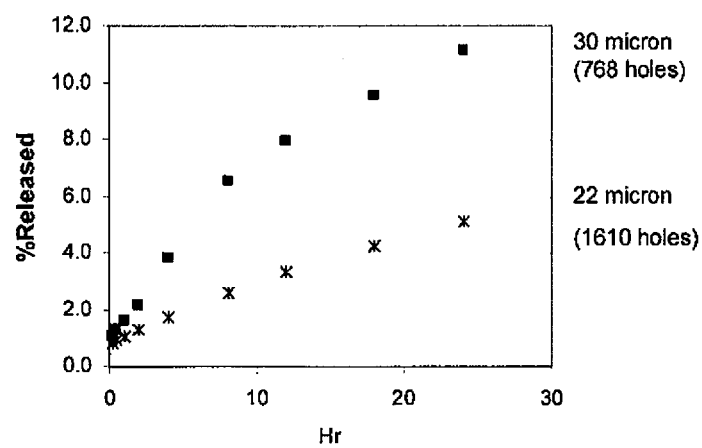

The graphs of FIGS. 10A through 10C show examples of how the number and/or size of apertures 31 formed in a substance eluting reservoir 14, 102 may control or affect the rate at which the substance actually elutes from the reservoir 14, 102. These graphs are based on in vitro experiments using a device 10 of the type shown in FIG. 1A. One milliliter of Triamcinolone Acetonide Injectable Suspension, USP (Kenalog®-40, Bristol-Myers Squibb, Somerville, N.J.) was injected by syringe through Luer hub 16 and into reservoir 14. The Luer hub 16 and proximal shaft 12a were then cut away in the manner described above and shown in FIG. 3K and the cut proximal end of the remaining distal shaft 12 b was sealed and wiped clean. The cut-away Luer hub 16 and proximal shaft 12a were retained and the amount of residual Triamcinolone Acetonide contained therein was determined. The filled substance delivery device 10 was then attached to a sinker and dropped into a revolving paddle-type dissolution test vessel containing 500 milliliters of 0.3% sodium dodecyl sulfate media at 37 degrees C. A standard USP paddle was revolved at 50 rpm and the amount of Triamcinolone Acetonide dissolved in the media was determined at various time points by High Performance Liquid Chromatography (HPLC).

Related to FIG. 10A, a substance delivery device 10 has a 3.5 mm×13 mm reservoir 14 with a total of 2254 laser-cut 16 micron apertures 31 formed therein in a staggered configuration. The cumulative total release of Triamcinolone Acetonide from the device 10 was determined over a period of seven days and is shown graphically in FIG. 10A as an cumulative total release vs. time (i.e., an elution curve). As seen in the graph of FIG. 10A, more than 2000 µg of Triamcinolone Acetonide was released from the device 10 over seven days, with more than half of that amount being released within the first two days. An initial portion (e.g., from 0 to about day 3) of this elution curve is steeper than a later portion (e.g., from about day 3 to about day 7) of this elution curve, indicating that the incremental amount of Triamcinolone Acetonide released each day began to taper off or decrease at around day 3. The total and incremental release of Triamcinolone Acetonide over seven days in this example is consistent with dosages of Triamcinolone Acetonide known to be effective when administered topically to nasal mucosa.

In FIGS. 10B and 10C, the cumulative total amount (µg) of Triamcinolone Acetonide released (FIG. 10B) and the percent (%) of available Triamcinolone Acetonide released were determined over a 24 hour period for a device 10 having a total of 768 laser cut 30 micron apertures 31 formed in its reservoir 14 and in another device 10 having a total of 1610 laser cut 22 micron apertures 31 formed in its reservoir 14. As shown in the graphs of FIGS. 10B and 10C, the device 10 having 1610×22 micron apertures delivered a lower percentage of the available Triamcinolone Acetonide (i.e., about 5% in 24 hours) and achieved a lower cumulative total release of Triamcinolone Acetonide (i.e., approximately 150 µg in 24 hours) than the device having 768×30 micron apertures (i.e., about 110% and about 450 µg, respectively). This demonstrates the manner in which the total number and size of the apertures 31 formed in the reservoir 14 may be varied to achieve a prescribed rate of release of a particular agent over a desired period of time. For applications where the device 10 is to be implanted within a paranasal sinus, air cell, Eustachian tube, naso-lacrimal duct or elsewhere within the ear, nose or throat, delivery of effective amounts of the substance may be accomplished for time periods ranging from less than 1 hour to 90 days or more. For treatment of paranasal sinusitis, delivery of therapeutic agents for up to 7 to 14 days may typically be desirable, but such time period may vary depending on the particular agent to be delivered and the severity of the condition being treated.

Figure 11:
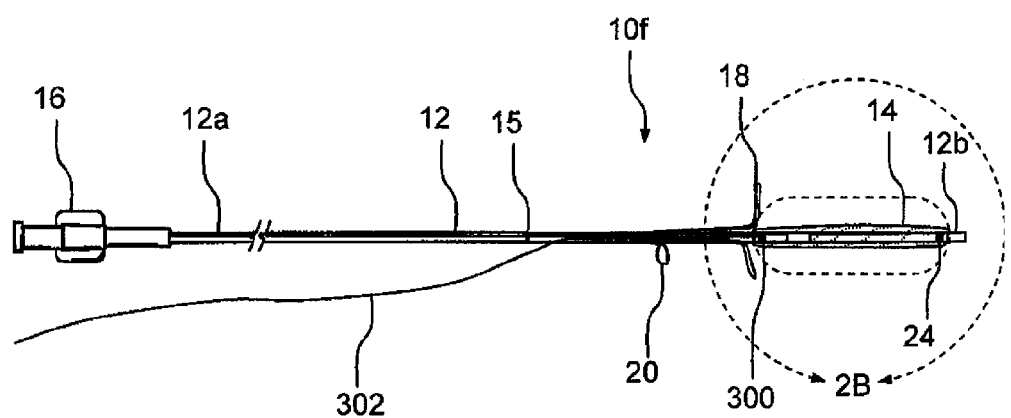
FIG. 11A is a side view of one embodiment of substance delivery device of the present invention equipped for iontophoretic delivery of a substance.
FIG. 11B is an enlarged view of a distal portion of the device of FIG. 11A.
FIG. 11C is a diagram of the device of FIG. 11A implanted within the ethmoid air cells of a human subject and operatively connected to apparatus for iontophoretic delivery of a substance from the reservoir of the device to mucosal tissues lining the ethmoid air cells.
Figure 11:
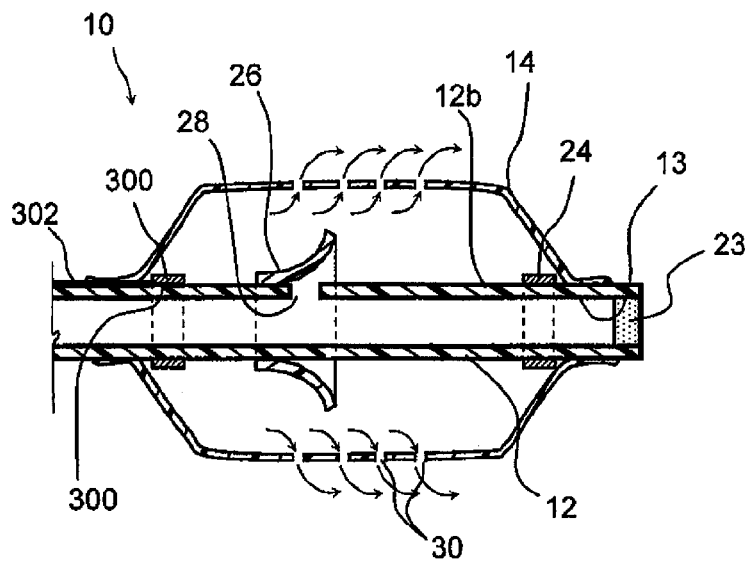
Figure 11C:
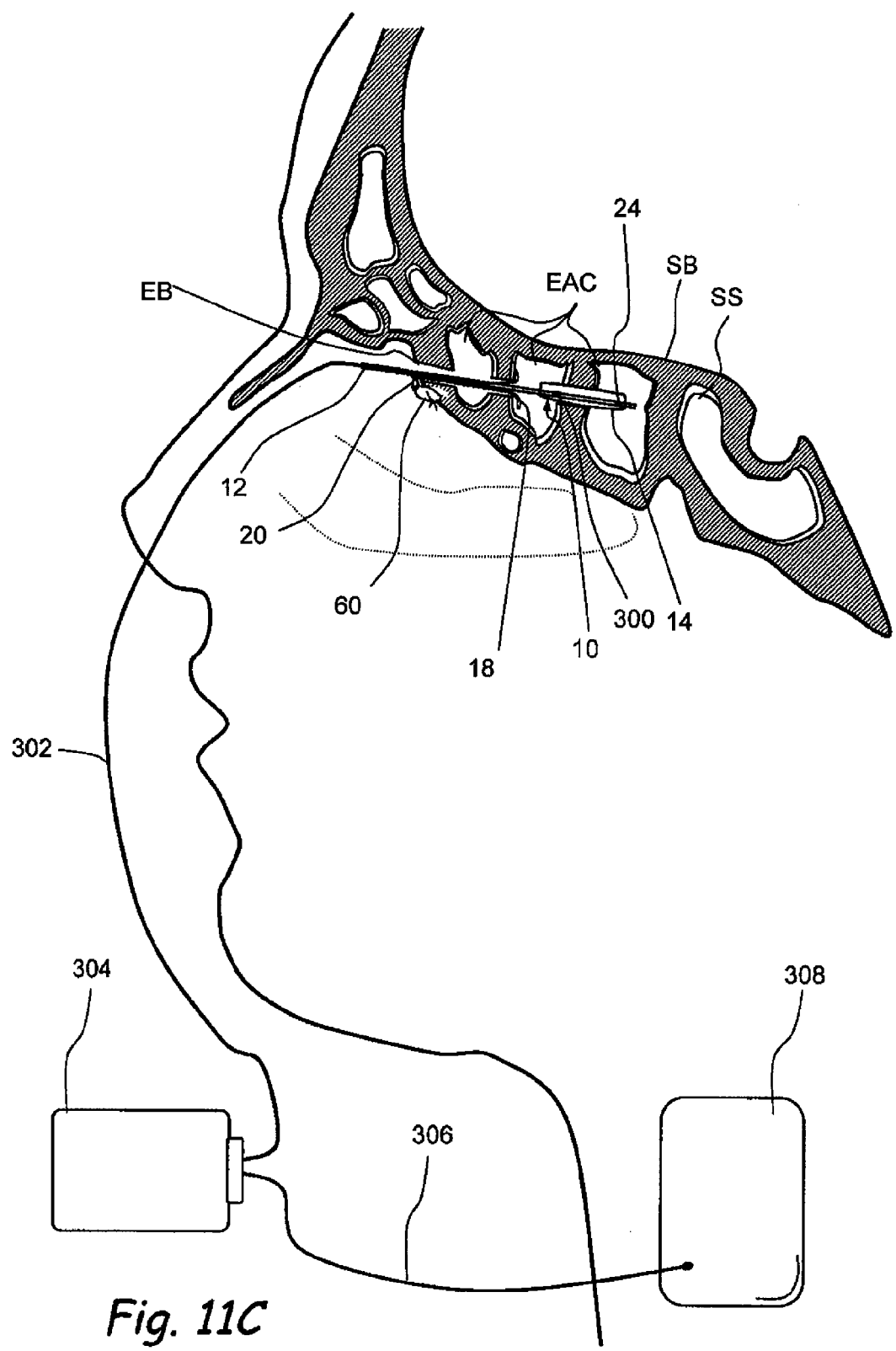

FIGS. 11A through 11C show another embodiment of a device 10f which is equipped for iontophoretic delivery of a diagnostic or therapeutic substance. Iontophoresis may be used to propel a charged medication or bioactive-agent through or into skin or mucous membrane by repulsive electromotive force. The device 10f seen in FIGS. 11A-11C may be of essentially the same construction as the devices 10-10e described above, but will include an electrode for delivering a small electrical charge to a similarly charged active agent contained in the reservoir 14. In the particular example of FIG. 11A, the device 10f has all of the same components as the device 10 shown in FIG. 1A, except that the proximal radiopaque marker 22 of the device 10 of FIG. 1A is replaced by a proximal radiopaque electrode 300 which functions both as a radiographic marker and an iontophoresis electrode. Of course, it is to be understood that, alternatively. a separate electrode that does not necessarily function as a radiographic marker may be used. A wire 302 extends from the proximal radiopaque electrode 300 and is connectable to an iontophoresis power source 304. As may be appreciated from FIG. 11B, this wire 302 may extend out of the proximal end of reservoir 14 outside of the catheter shaft 12. A ground electrode 308 (e.g., a patch electrode) is also attached to the subject's body and to the iontophoresis power source 304, as seen in FIG. 11C. Examples of iontophoresis power sources, systems, voltages and current levels that may be used to deliver substances into or through mucosal tissue are known by those of skill in the art of iontophoretic drug delivery and include those described in U.S. Pat. No. 6,006,130, which is expressly incorporated herein by reference. Typically, the currents used to deliver chemical agents by iontophoresis range from 0.1 mA to 5 mA and are often in the range of 0.5 mA to 3 mA. Duration can range from 1 min to 30 mins and is often between 5 and 15 minutes. Obviously many factors impact the current and time applied and those variables themselves are often used to determine total delivery dose. Current form, constant or pulsed, may also be varied depending on the delivery profile desired. Anti-inflammatory medications as well as antibiotics, antipoliferatives, anti fungal, vasoregulators, anti virals and antihistamines are examples of types of agents that may be delivered using this device 10f and method. By way of example only, lidocaine, epinephrine, 5 fluorourocil, Antiproliferative factor, heparin, diamine silver fluoride (AgF); sodium fluoride (NaF), iodine zinc iodide (JJZ), 5-iodo-2-deoxyuridine and calciumchlorate are types of agents that could be delivered. The advantages of employing iontophoresis include, accelerated delivery of the substance, higher tissue concentration(s) of the substance, maintenance of ionic balance, local delivery and atraumatic delivery.

In some applications, the device 10f may be implanted and connected to the iontophoresis power source 304 for an initial period of time (e.g., 1-3 hours) and, thereafter, the wire 302 may be disconnected from the power source 304 and trimmed or cut of, allowing the device 10f to remain implanted within the subject's body for ongoing non-iontophoretic substance delivery as described herein. This initial period of iontophoretic substance delivery may accelerate or hasten the accrual of therapeutically effective levels of the substance within the mucosa or other affected tissue, thereby facilitating greater overall efficacy and shorter recovery time.

Figure 9:
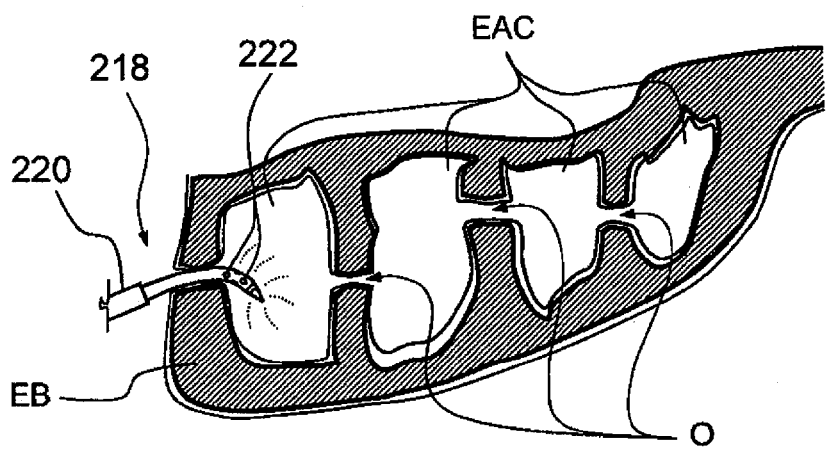
FIG. 9A shows a diagram of surgically modified ethmoid air cells having an irrigation device of the present invention inserted therein.
FIG. 9B is an enlarged view of the distal end of the irrigation device seen in FIG. 9A.
FIG. 9C is a cross sectional view through the distal end of the irrigation device seen in FIG. 9B.
FIGS. 9D-9F show a filling device of the present invention in various stages of operation.
Figure 9:
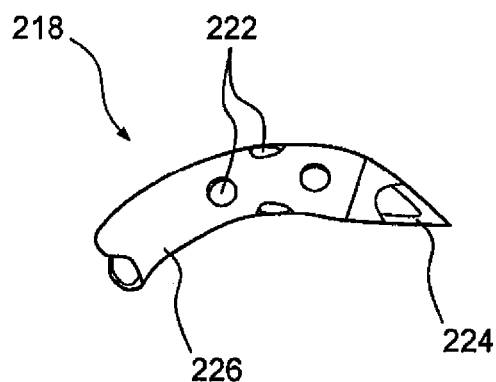
Figure 9:
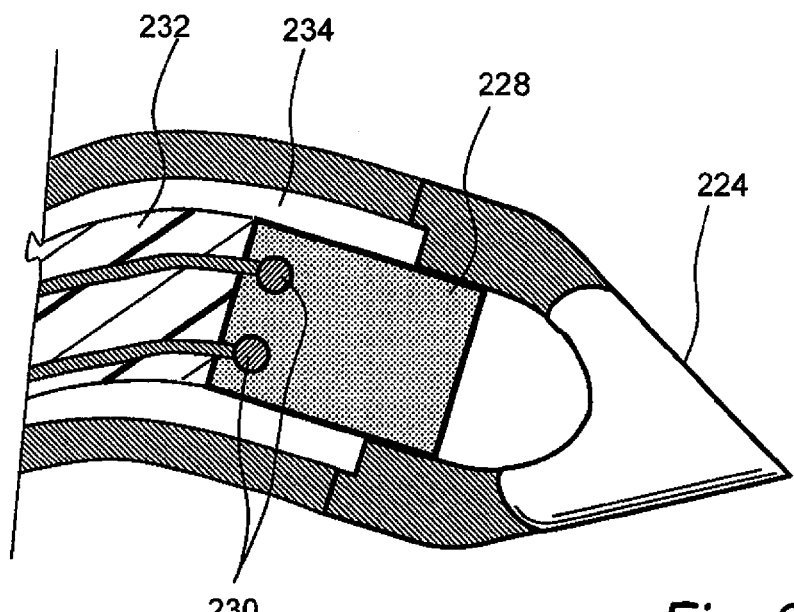
Figure 9:
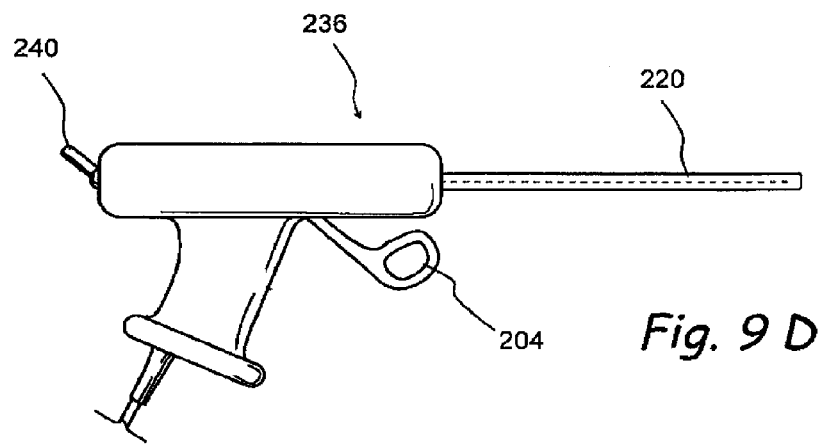
Figure 9:
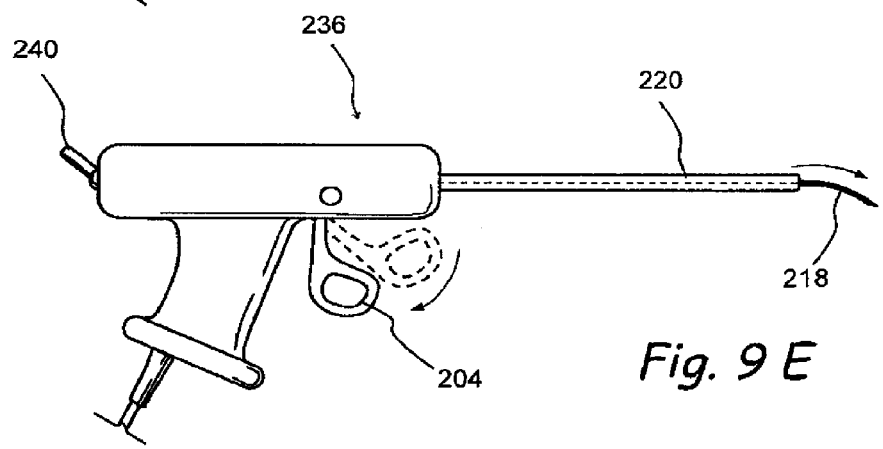
Figure 9:
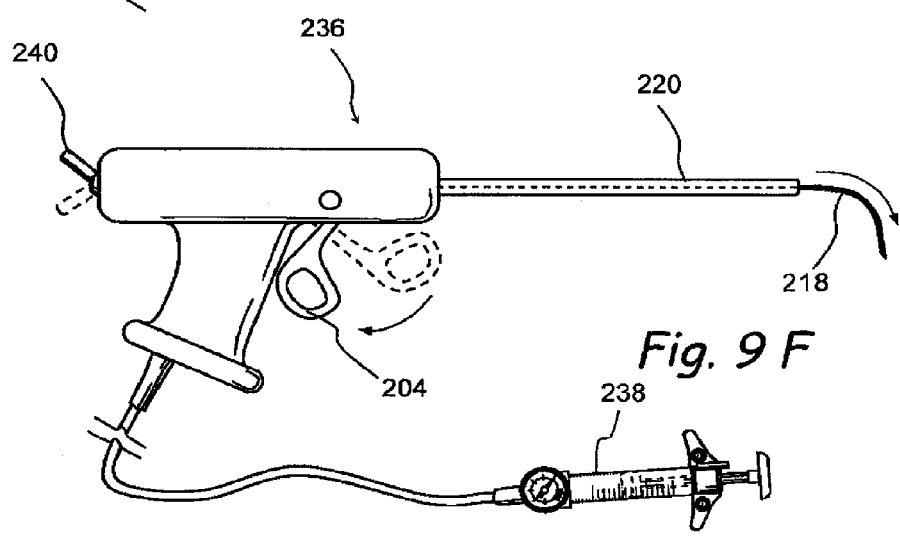

One or more anatomical regions can be irrigated with a suitable irrigating solution to deliver one or more substances to the anatomical regions. The anatomical regions to be irrigated may be accessed through natural openings or passages or through artificially created openings. FIGS. 9A to 9C show an irrigation catheter useable to irrigate the ethmoid sinuses as well and various other anatomical regions including, but not limited to other paranasal sinuses and cavities or passageways in the ear, nose or throat. FIG. 9A shows the general working environment of an irrigating device being used to irrigate multiple ethmoid air cells. The irrigation catheter 218 is introduced into an ethmoid air cell through an irrigation sheath 220. In one method embodiment, this is done by introducing irrigation catheter 218 enclosed in irrigation sheath 220 into a nostril. Thereafter, irrigation catheter 218 is advanced through the nasal cavity such that the distal tip of irrigation catheter 218 is adjacent to the ethmoid bulla. Thereafter irrigation catheter 218 is further advanced such that the distal tip of irrigation catheter 218 penetrates through a region of the ethmoid bulla and enters an ethmoid air cell. Irrigation catheter 218 comprises an irrigation lumen that terminates in one or more irrigation holes 222 through which an irrigating fluid is delivered. In the embodiment shown, the distal end of irrigation catheter 218 is sharp. In FIG. 9A, the distal tip of irrigation catheter 218 is located within an ethmoid air cell. Irrigation catheter 218 is used to deliver the irrigating fluid at high pressure to the ethmoid air cell. The irrigating fluid then spreads to adjacent anatomical structures such as adjacent ethmoid air cells through natural anatomical channels connecting the adjacent ethmoid air cells. Thus a fluid can be delivered to multiple anatomical structures such as ethmoid air cells without visualizing or physically accessing each individual ethmoid air cell. Another advantage of this method is the ability to deliver an irrigating fluid even to ethmoid air cells that cannot be visualized. This is particularly useful to treat ethmoid air cells since it is difficult to visualize and map the complicated anatomy of the ethmoid air cells. The irrigating fluid can be used to flush out pus, mucus or other biological or pathological materials from the ethmoid air cells. In a particular embodiment, the irrigating fluid is saline. In another embodiment, the irrigating fluid has one or more therapeutic substances to be delivered to the lining of the ethmoid air cells. Multiple ethmoid air cells can be accessed by the tip of irrigation catheter and the irrigating fluid can be delivered under pressure in each accessed ethmoid air cell to deliver the irrigating fluid to substantially all ethmoid air cells. Irrigation catheter 218 may be curved or substantially straight. In a preferred embodiment, the distal region of irrigation catheter 218 is bent at an angle to the proximal region. This is useful to introduce irrigation catheter 218 into the nasal cavity such that the distal sharp end of irrigation catheter 218 passes parallel to the skull base. This minimizes the risk of penetrating the skull base. In another embodiment, irrigation catheter 218 has two components: a removable component and an implantable component. The removable component is removed from the anatomy after performing a procedure. The implantable component is retained in the anatomy for a period ranging from one hour to ninety days, more preferably seven to twenty-nine days, most preferably about fourteen days. The implantable component can be used as a substance eluting device. The implantable component can also be used as a spacer or stent to maintain patency of a natural or artificially created opening or region.

As seen in FIG. 9B, the distal end of the irrigation catheter 218 has multiple irrigation holes 222 through which an irrigating fluid may be introduced. The distal end of this irrigation catheter 218 is a conical penetrating tip 224 designed to penetrate through anatomical regions such as the ethmoid bulla. Conical penetrating tip 224 is preferably made of metal including, but not limited to stainless steel or Nitinol. The proximal end of conical penetrating tip 224 is attached to irrigation catheter shaft 226. Irrigation catheter shaft 226 can be straight or curved or bent. Irrigation catheter shaft 226 can be metallic or polymeric. The outer diameter of irrigation catheter shaft 226 is preferably between about 0.028 inches and about 0.036 inches.

One or more devices may be introduced over irrigation catheter 218 into anatomical regions. In one method embodiment, a guidewire in introduced into an anatomical region through one of irrigation holes 222. Irrigation catheter 218 is then removed from the anatomy leaving behind the guidewire. The guidewire is then used to introduce one or more devices.

The method illustrated in FIG. 9A may be performed with fluoroscopic or endoscopic visualization or with the use of an optical or electromagnetic surgical navigation modality. In an embodiment of a method of using irrigation catheter 218 with an electromagnetic surgical navigation modality, irrigation catheter 218 is substantially rigid. An electromagnetic image guidance sensor is attached to irrigation catheter 218. The location and/or the trajectory of the distal region of irrigation catheter 218 is then tracked in the anatomy using an electromagnetic surgical navigation modality. In an embodiment of a method of using irrigation catheter 218 with an optical surgical navigation modality, irrigation catheter 218 is substantially rigid. An optical image guidance sensor is attached to irrigation catheter 218. The location and/or the trajectory of the distal region of irrigation catheter 218 is then tracked in the anatomy using an optical surgical navigation modality. In a particular embodiment, irrigation catheter 218 comprises an electromagnetic sensor. FIG. 9C shows a section through a distal region of the irrigation catheter in FIG. 9B showing an electromagnetic surgical navigation sensor enclosed within the irrigation catheter. In FIG. 9C, irrigation catheter 218 comprises conical penetrating tip 224 attached to irrigation catheter shaft 226. Enclosed within conical penetrating tip 224 and irrigation catheter shaft 226 is an electromagnetic surgical navigation sensor 228. Electromagnetic surgical navigation sensor 228 is electrically connected to an electromagnetic surgical navigation system through two low profile electrical leads 230. Electrical leads 230 are enclosed in a layer of electrical insulation 232 that electrically isolates electrical leads 230 from an irrigation lumen 234 of irrigation catheter 218. The location and/or the trajectory of the distal region of irrigation catheter 218 is then tracked with the electromagnetic surgical navigation system.

The viscosity and/or the surface tension of the irrigating fluid delivered by irrigation catheter 218 can be optimized to obtain desired characteristics of the irrigating fluid. For example, a viscous irrigating fluid can be used to prolong the residence time of the irrigating fluid in an anatomical region. This is especially suitable for delivery of substances to the anatomical region. A less viscous fluid can be used to flush the anatomical region of pus, mucus or other materials. An irrigating fluid with a low surface tension can be used to cover a large surface area of the anatomical region. The low surface tension allows the irrigating fluid to form a thin layer or microfilm of the irrigating fluid that covers a large surface area of the anatomical region. In one embodiment, the low surface tension irrigating fluid is obtained by adding a surfactant to an irrigating fluid. This is especially useful to deliver substances over a large surface area or to flush a large surface area, especially in anatomical regions such as ethmoid sinuses that have complicated 3-D geometries. In a particular embodiment, a low surface tension irrigating fluid containing one or more substances is delivered to the ethmoid sinuses. The low surface tension irrigating fluid spreads over the mucosal surface of the ethmoid sinuses. Thus the irrigating fluid delivers the one or more substances to a large surface area of the ethmoid sinuses.

FIGS. 9D-9F show a handheld introducing device useable for introducing an irrigation catheter such as catheter 218 described above to a desired location within the body. Introducing device 236 comprises irrigation sheath 220 attached to the body of the introducing device 236. Irrigation catheter 218 can be introduced through irrigation sheath 220 into the anatomy. Irrigation catheter 218 and/or irrigation sheath 220 can be bent or curved or substantially straight. Introducing device 236 is connected to an inflation device 238 (FIG. 9F). Inflation device 238 is a source of high pressure irrigating fluid to be delivered through irrigation catheter 218. In the embodiment shown in FIGS. 9D-9F, inflation device 238 is a syringe with a pressure gauge. Introducing device 236 also comprises a trigger 204. Trigger 204 is used to move irrigation catheter 218 relative to irrigation sheath 220. In a preferred embodiment, trigger 204 is connected to a ratchet mechanism that advances or retracts irrigation catheter 218. Introducing device 236 also comprises a thumb trigger 240. Thumb trigger 240 controls a valve which controls the flow of fluid between inflation device 238 and irrigation catheter 218. In FIG. 9D, the distal end of irrigation sheath 220 is inserted into the nasal cavity. The distal sharp tip of irrigation catheter 218 is located within irrigation sheath 220 to prevent undesired damage to the surrounding anatomy as the sheath 220 is inserted and maneuvered into position. Thereafter, as seen in FIG. 9E, trigger 204 is moved by a user causing the irrigation catheter 218 to advance distally such that its distal end emerges from the irrigation sheath 220. Irrigation catheter 218 then penetrates through the anatomical region and enters an anatomical cavity. In FIG. 9F, the position of irrigation catheter 218 is adjusted using trigger 204. Thumb trigger 240 is flipped to create fluid flow from the inflation device 238 through irrigation catheter 218. Inflation device 238 is used to deliver a high pressure irrigating fluid to irrigation catheter 218 to irrigate the anatomical cavity. In a particular method embodiment, the distal tip of irrigation catheter 218 penetrates through the ethmoid bulla and enters an ethmoid air cell. Thereafter, irrigation catheter 218 is used to irrigate multiple ethmoid air cells. The irrigating fluid spreads to adjacent ethmoid air cells through natural passageways connecting the ethmoid air cells. The irrigating fluid may be saline or may comprise one or more therapeutic agents. Introducing device 236 of FIGS. 9D-9F is designed to be operated by a user with a single hand. This design has the advantage of keeping the other hand of the user free. The user can then hold an endoscope with the other hand and use the endoscope to visualize the anatomy.

The abovementioned embodiments may be used as spacing devices after an open surgical, endoscopic, or an interventional procedure. The outside of reservoir 14 and shaft 12 can be coated with a steroid, anti-scar agent, etc., in a relatively high concentration and a lower concentration agent in the reservoir 14. Further, these devices may be further coated with an anti-infective agent or may be constructed of a substance which is naturally bacteriostatic to reduce the likelihood of toxic-shock syndrome or other device related infections. Such a naturally bacteriostatic material would be a biodegradable substance which, through the process of biodegradation, undergoes hydrolysis, releasing bacteriostatic substances such as hydrogen peroxide.

In some applications, the devices 10, 104 of this invention may be implanted within openings (e.g., natural ostia, surgically altered ostia, other man-made openings) of paranasal sinuses to facilitate the treatment of a disease or disorder affecting the paranasal sinus. In such applications, the opening of the paranasal sinus may be enlarged (e.g., dilated) before or after placement of a device 10, 104 of the present invention within such opening. One such procedure is balloon dilation of sinus cavity ostia. In such procedure, a guide catheter having a substantially fixed shape is inserted through the nose and advanced to a position where the distal end of the guide catheter is adjacent to the ostium of a paranasal sinus. A guidewire is then advanced through the guide catheter (e.g., Relieva™ Guide Catheter, Acclarent, Inc., Menlo Park, Calif.) and into the paranasal sinus. Thereafter, a balloon catheter (e.g., Relieva™ Balloon Catheter, Acclarent, Inc., Menlo Park, Calif.) is advanced over the guidewire and is used to dilate the ostium of the paranasal sinus, thereby improving drainage from and/or ventilation of that paranasal sinus. Examples of such devices and procedures for balloon dilation of a paranasal sinus ostium are described in U.S. patent application Ser. Nos. 10/829,917 entitled "Devices, Systems and Methods for Diagnosing and Treating Sinusitis and Other Disorders of the Ears, Nose and/or Throat," now U.S. Pat. No. 7,654,997, issued Apr. 21, 2004; Ser. No. 10/944,270 entitled "Apparatus and Methods for Dilating and Modifying Ostia of Paranasal Sinuses and Other Intranasal or Paranasal Structures," now U.S. Pat. Pub. No. 2006/0004323, published Jan. 5, 2006, Ser. No. 11/116,118 entitled "Methods and Devices for Performing Procedures Within the Ear, Nose, Throat and Paranasal Sinuses," now U.S. Pat. No. 7,720,521, issued May 18, 2010, Ser. No. 11/150,847 entitled "Devices, Systems And Methods Useable For Treating Sinusitis," now U.S. Pat. No. 7,803,150, issued Sep. 28, 2010 and Ser. No. 11/234,395 entitled Devices and Methods for Delivering Therapeutic Substances for the Treatment of Sinusitis and Other Disorders," now U.S. Pat. No. 7,410,480, issued Aug. 12, 2008, the entire disclosure of each such patent application being expressly incorporated herein by reference.

The term substance as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or non-fluid. For example, in some applications where it is desired to treat or prevent a microbial infection, the substance delivered may comprise a pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an anesthetic agent with or without a vasoconstriction agents (e.g. Xylocalne with or without Epinephrine), an analgesic agent, an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations, viral vectors carrying proteins or nucleic acids such as DNA or mRNA coding for important therapeutic functions or substances, cauterizing agents e.g. silver nitrate, etc.

Some nonlimiting examples of antimicrobial agents that may be used in this invention include acyclovir, amantadine, rimantadine, oseltamivir, zanamivir, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillins including penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813 (Lin et al.) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDs), analgesic agents or antipyretic agents. For example, corticosteroids that have previously administered by intranasal administration may be used, such as beclomethasone (Vancenase® or Beconase®), flunisolide (Nasalide®), fluticasone proprionate (Flonase®), triamcinolone acetonide (Nasacort®), budesonide (Rhinocort Aquae), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor).

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (Mucomyst™, Mucosil™) and guaifenesin.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrome®) and nedocromil.

Additionally or alternatively, in some applications such as those where it is desired to prevent or inhibit the effect of histamine, the substances delivered in this invention may include various antihistamines such as azelastine (e.g., Astylin®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin/EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired.

Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, antianxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's disease, Huntington's disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

The devices and methods disclosed herein may be used to deliver several combinations of two or more substances disclosed herein to a suitable target anatomical region. In one particular embodiment, the devices and methods disclosed herein are used to deliver a combination of an anti-inflammatory agent (e.g. a steroid or an NSAID) and a mucolytic agent.

The devices and methods disclosed herein may be used to deliver gels or viscous liquids comprising one or more substances to anatomical regions such as paranasal sinuses. Such gels or viscous liquids may coat and adhere to a mucous membrane and thus provide sustained delivery of one or more substances to the mucous membrane. In one embodiment, a plasticized hydrocarbon gel comprising gelatin, pectin and sodium carboxymethylcellulose and a suitable substance may be delivered to a mucous membrane such as the mucous membrane of a paranasal sinus. Such gels can be used for sustained delivery of the suitable substance to the mucous membrane.

One or more of the substance reservoirs disclosed herein may comprise multiple compartments such that each compartment stores a particular substance formulation. The multiple compartments prevent mixing of multiple substance formulations before substance formulations are delivered to the anatomy.

One or more of the substance reservoirs comprising holes or pores may be filled with a suitable substance at a sufficiently high pressure to cause a portion of the substance to squirt out of the holes or pores. This process may be used to deliver an initial bolus of the substance to the surrounding anatomy.

One or more of the substance reservoirs disclosed herein may be filled with a suitable substance after the substance reservoir is introduced in an anatomical region. Alternatively, one or more of the substance reservoirs disclosed herein may be filled with a suitable substance before the substance reservoir is introduced in an anatomical region. Alternatively, one or more of the substance reservoirs disclosed herein may be pre-filled with a solid, lyophilized or concentrated substance. The solid, lyophilized or concentrated substance is converted to an active form by introducing a solvent into the substance reservoir. This may be done just before or after the substance reservoir is introduced in an anatomical region. Alternatively, one or more of the substance reservoirs disclosed herein may be pre-filled with an inactive form of a substance. The inactive form of the substance is converted to an active form by introducing an activating agent into the substance reservoir. This may be done just before or after the substance reservoir is introduced in an anatomical region.

The devices and methods disclosed herein may be used to treat middle ear or inner ear pathologies. This may be done by accessing the middle ear through the Eustachian tube or through the tympanum. For example, the devices and methods disclosed herein may be used to treat Meniere's disease by delivering gentamicin to the inner ear through the round window membrane. The devices and methods disclosed herein may be used to treat a variety of diseases or disorders by a variety of substances including, but not limited to the substances and diseases or disorders disclosed in Table 1.

TABLE 1

| ANATOMICAL LOCATION OF THE DISEASE/ DISORDER | DISEASE/ DISORDER TO BE TREATED | EXAMPLES OF SUBSTANCES THAT MAY BE DELIVERED |
|---|---|---|
| Inner ear | Meniere's disease, Vertigo | Gentamicin, Vestibular suppressants (e.g. anticholinergics, antihistamines, and benzodiazepines), antiemetic drugs, diuretics, etc. |
| Inner ear | Autoimmune inner ear disease | Corticosteroids, etc. |
| Inner ear | Free radical induced damage | Glutamate antagonists(e.g. memantine, caroverine and magnesium), Calpain inhibitor (e.g. Leupeptin), Antioxidants (e.g. glutathione, Methionine), etc. |
| Inner ear | Hearing loss and tinnitus | Neurotrophic factors (e.g. NeuroTrophin-3), Genes for Neurotrophic factors such as BDNF (brain-derived neurotropic factor), etc. |
| Middle ear | Otitis media | Amoxicillin, ampicillin, azithromycin, cefaclor, cefdinir, ceftibuten, ceftriaxone, erythomycin, clarithromycin, combination of trimethoprim/sulfamethoxazole, ofloxacin, etc. |
| Inner ear | Degeneration of inner ear cells, especially sensory hair cells and associated neurons, | Grafted neural stem cells, embryonic stem cells, dorsal ganglion cells and cell lines derived from fetal inner ear cells, autologous bone marrow stromal cells, etc. |

It is to be further appreciated that, as described herein, the implantable portion of a substance delivery device 10 may include a through lumen that may function as a vent and/or drain when such implantable portion device is in the Eustachian tube or through an opening formed in the tympanum.

The devices and methods disclosed herein may be used to mark an anatomical region with a suitable imageable marker. For example, the devices and methods disclosed herein may be used to deliver a radio opaque marker such as a radio opaque contrast agent to an ostium of a paranasal sinus. This enables a user to image the ostium of the paranasal sinus using X-rays or fluoroscopy.

One or more of the substance delivery devices disclosed herein may comprise a curved, bent or angled region to enable the drug delivery devices to navigate through the anatomy.

The distal-most regions of one or more substance delivery devices disclosed herein may comprise an atraumatic tip. The atraumatic tip is used to prevent or reduce damage to the anatomy by the distal-most regions of the one or more substance delivery devices.

The outer surface of one of more substance delivery devices disclosed herein may comprise a coating that reduces or eliminates the risk of encrusting of the outer surface by a biological material. In one embodiment, the coating comprises a material that absorbs water to form a gel. Examples of such materials include, but are not limited to hyaluronic acid, etc.

One or more of the substance delivery devices disclosed herein may be designed to be easily removable from the anatomy after completion of a treatment.

One or more of the substance delivery devices disclosed herein may be refilled after a significant volume of substance filled in a substance reservoir has been delivered to the anatomy.

One or more of the substance delivery devices disclosed herein may comprise one or more markers to enable a user to locate and/or navigate the substance delivery devices through the anatomy. For example, the substance delivery devices may comprise visual markers to enable the user to determine the depth of insertion of the substance delivery devices into the anatomy. In another example, the substance delivery devices may comprise imaging markers to enable the user to locate and/or navigate the substance delivery devices using imaging modalities such as X-rays, MRI, etc.

As used herein, the term "opening or a paranasal sinus" shall include any transnasally accessible opening in a paranasal sinus or air cell such as natural ostia, surgically altered natural ostia, surgically created openings, antrostomy openings, ostiotomy openings, burr holes, drilled holes, ethmoidotomy openings, ethmoidectomy openings, natural or man made passageways, etc.

As used herein, the term "implantable" shall include any device that is maintained in the body of a human or animal for a period ranging from 30 minutes to 60 days.

As used herein, the term "porous" shall include any element that comprises one or more pores or apertures.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method for treating a human or animal subject, said method comprising the steps of:
   (a) forming an opening into at least one ethmoid air cell;
   (b) providing or obtaining an implantable device, wherein the implantable device comprises:
      (i) a self-expanding member,
      (ii) a connector,
      (iii) a shaft connecting the self-expanding member and the connector, and
      (iv) a delivery sheath having a lumen and a distal end, wherein the shaft is positioned within the lumen of the delivery sheath
   (c) advancing the distal end of the delivery sheath into a nose of the subject to a location adjacent to the opening formed in at least one ethmoid air cell, wherein the self-expanding member is in a constrained configuration within the lumen of the delivery sheath during the act of advancing the distal end of the delivery sheath;
   (d) separating the delivery sheath from the self-expanding member, thereby releasing the self-expanding member from the delivery sheath such that the self-expanding member expands to an expanded configuration wherein the self-expanding member contacts with anatomy surrounding the opening formed in the at least one ethmoid air cell;
   (e) separating a distal portion of the shaft from a proximal portion of the shaft at a point between the self-expanding member and the connector;
   (f) removing the delivery sheath from the shaft; and
   (g) allowing the implantable device to remain implanted within the opening formed in the at least one ethmoid air cell.

2. The method according to claim 1 wherein the opening formed in at least one ethmoid air cell the comprises an opening formed in an ethmoid bulla.

3. The method according to claim 1 wherein the opening formed in at least one ethmoid air cell the comprises a channel that has been created in the at least one diseased ethmoid air cell.

4. The method according to claim 1 wherein the step of forming the opening into at least one the ethmoid air cell comprises surgically forming the opening into at least one the ethmoid air cell.

5. The method according to claim 1 wherein the step of forming the opening into at least one the ethmoid air cell comprises performing a needle ethmoidotomy.

6. The method according to claim 5 wherein the step of performing the needle ethmoidotomy comprises:
   (i) obtaining an ethmoidotomy needle having a distal tip;
   (ii) inserting the ethmoidotomy needle into the subject's nose and advancing the ethmoidotomy needle to a position where the distal tip is aligned with an ethmoid bulla;
   (iii) pushing the ethmoidotomy needle through at least the ethmoid bulla to form the opening into at least one the ethmoid air cell.

7. The method according to claim 6 wherein the ethmoidotomy needle is pushed through the ethmoid bulla and through a plurality of ethmoid air cells thereby forming a channel that extends through the plurality of ethmoid air cells.

8. The method according to claim 1 wherein the self-expanding member expands to conform to the size and shape of the opening formed into at least the one ethmoid air cell.

9. The method according to claim 1 wherein the self-expanding member comprises material that absorbs endogenous or introduced fluid causing the self-expanding member to swell to the expanded configuration.

10. The method according to claim 1 wherein the implantable device also delivers a therapeutic substance to treat the ethmoid disease.

11. The method according to claim 10 wherein the substance comprises a steroid.

12. The method according to claim 11 wherein the steroid is selected from the group consisting of: beclomethasone; flunisolide; fluticasone; triamcinolone; budesonide; loterednol, mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone, methylprednisolone and salts thereof.

13. The method according to any of claim 10, 11 or 12 wherein the implantable device remains implanted and delivers the substance for at least 7 days.

14. The method according to claim 13 wherein, within the first two days of implantation, the implantable device delivers at least half of the total amount of substance that the implantable device delivers over the 7 days of implantation.

15. The method according to claim 13 wherein the substance comprises mometasone.

* * * * *